(12) United States Patent
Mesgarani et al.

(10) Patent No.: US 11,373,672 B2
(45) Date of Patent: Jun. 28, 2022

(54) SYSTEMS AND METHODS FOR SPEECH SEPARATION AND NEURAL DECODING OF ATTENTIONAL SELECTION IN MULTI-SPEAKER ENVIRONMENTS

(71) Applicant: The Trustees of Columbia University in the City of New York, New York, NY (US)

(72) Inventors: Nima Mesgarani, New York, NY (US); Yi Luo, New York, NY (US); James O'Sullivan, New York, NY (US); Zhuo Chen, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 16/169,194

(22) Filed: Oct. 24, 2018

(65) Prior Publication Data

US 2019/0066713 A1 Feb. 28, 2019

Related U.S. Application Data

(63) Continuation-in-part of application No. PCT/US2017/037186, filed on Jun. 13, 2017.
(Continued)

(51) Int. Cl.
*G10L 25/30* (2013.01)
*A61B 5/318* (2021.01)
(Continued)

(52) U.S. Cl.
CPC .............. *G10L 25/30* (2013.01); *A61B 5/318* (2021.01); *G10L 17/26* (2013.01); *A61B 5/12* (2013.01); *G10L 21/0272* (2013.01); *G10L 25/66* (2013.01)

(58) Field of Classification Search
CPC ..... G10L 25/30; G10L 17/26; G10L 21/0272; G10L 25/66; A61B 5/318; A61B 5/12
See application file for complete search history.

(56) References Cited

U.S. PATENT DOCUMENTS

| 5,150,323 A | 9/1992 | Castelaz |
| 6,330,339 B1 | 12/2001 | Ishige et al. |

(Continued)

FOREIGN PATENT DOCUMENTS

| CN | 102222508 A | * | 10/2011 | |
| EP | 1752969 A1 | * | 2/2007 | ........... G06K 9/6245 |

(Continued)

OTHER PUBLICATIONS

Bell et al, An Information-Maximization Approach to Blind Separation and Blind Deconvolution, Neural Computation 7, Massachusetts Institute of Technology, 1995, pp. 1129-1159 (Year: 1995).*

(Continued)

*Primary Examiner* — Linda Wong
(74) *Attorney, Agent, or Firm* — Occhiuti & Rohlicek LLP

(57) ABSTRACT

Disclosed are devices, systems, apparatus, methods, products, and other implementations, including a method comprising obtaining, by a device, a combined sound signal for signals combined from multiple sound sources in an area in which a person is located, and applying, by the device, speech-separation processing (e.g., deep attractor network (DAN) processing, online DAN processing, LSTM-TasNet processing, Conv-TasNet processing), to the combined sound signal from the multiple sound sources to derive a plurality of separated signals that each contains signals corresponding to different groups of the multiple sound sources. The method further includes obtaining, by the device, neural signals for the person, the neural signals being indicative of one or more of the multiple sound sources the (Continued)

person is attentive to, and selecting one of the plurality of separated signals based on the obtained neural signals. The selected signal may then be processed (amplified, attenuated).

39 Claims, 37 Drawing Sheets

Related U.S. Application Data

(60) Provisional application No. 62/733,215, filed on Sep. 19, 2018, provisional application No. 62/635,203, filed on Feb. 26, 2018, provisional application No. 62/578,324, filed on Oct. 27, 2017, provisional application No. 62/480,005, filed on Mar. 31, 2017, provisional application No. 62/429,549, filed on Dec. 2, 2016, provisional application No. 62/349,976, filed on Jun. 14, 2016.

(51) Int. Cl.
*G10L 25/66* (2013.01)
*G10L 21/0272* (2013.01)
*A61B 5/12* (2006.01)
*G10L 17/26* (2013.01)

(56) References Cited

U.S. PATENT DOCUMENTS

| | | | |
|---|---|---|---|
| 7,464,029 B2 | 12/2008 | Visser et al. | |
| 7,809,146 B2 | 10/2010 | Hiroe et al. | |
| 7,860,134 B2 | 12/2010 | Spence et al. | |
| 8,139,788 B2 | 3/2012 | Hiroe et al. | |
| 8,392,185 B2 * | 3/2013 | Nakadai | G10L 21/0272 704/235 |
| 8,694,306 B1 | 4/2014 | Short et al. | |
| 8,712,069 B1 | 4/2014 | Murgia et al. | |
| 8,831,936 B2 | 9/2014 | Toman et al. | |
| 8,971,558 B2 | 3/2015 | Lunner | |
| 9,025,800 B2 | 5/2015 | Kidmose et al. | |
| 9,210,517 B2 | 12/2015 | Pontoppidan et al. | |
| 9,215,527 B1 | 12/2015 | Saric et al. | |
| 9,313,585 B2 | 4/2016 | Lunner | |
| 9,390,712 B2 | 7/2016 | Yu et al. | |
| 9,432,777 B2 | 8/2016 | Lunner et al. | |
| 9,818,431 B2 * | 11/2017 | Yu | G10L 15/26 |
| 9,842,609 B2 | 12/2017 | Koretzky et al. | |
| 10,014,002 B2 | 7/2018 | Koretzky et al. | |
| 10,341,785 B2 * | 7/2019 | Barker | H04R 25/505 |
| 10,362,414 B2 | 7/2019 | Lunner et al. | |
| 10,839,822 B2 * | 11/2020 | Chen | G10L 21/0216 |
| 10,957,337 B2 * | 3/2021 | Chen | G06N 3/08 |
| 2001/0018652 A1 | 8/2001 | Mclaughlin et al. | |
| 2007/0083365 A1 | 4/2007 | Shmunk | |
| 2009/0116652 A1 | 5/2009 | Kirkeby et al. | |
| 2009/0279715 A1 | 11/2009 | Jeong et al. | |
| 2014/0098981 A1 * | 4/2014 | Lunner | H04R 25/50 381/320 |
| 2015/0269933 A1 | 9/2015 | Yu et al. | |
| 2016/0071526 A1 | 3/2016 | Wingate et al. | |
| 2016/0173047 A1 | 6/2016 | Hui et al. | |
| 2017/0178664 A1 | 6/2017 | Wingate et al. | |
| 2018/0122403 A1 | 5/2018 | Koretzky et al. | |
| 2018/0254040 A1 | 9/2018 | Droppo et al. | |
| 2019/0066713 A1 | 2/2019 | Mesgarani et al. | |
| 2019/0327570 A1 | 10/2019 | Pontoppidan et al. | |

FOREIGN PATENT DOCUMENTS

| | | | | |
|---|---|---|---|---|
| EP | 2200342 B1 | | 9/2013 | |
| EP | 2571289 B1 | | 2/2015 | |
| JP | 4406428 B2 * | 1/2010 | | G06K 9/6245 |
| JP | 6059072 B2 * | 1/2017 | | |
| JP | 6807029 B2 * | 1/2021 | | G10L 21/0272 |

OTHER PUBLICATIONS

Sawada et al, A Robust and Precise method of solving the permutation problem of Frequency-Domain Blind Source Separation, IEEE Transactions on Speech and Audio Processing, vol. 12, No. 5, Sep. 2004, pp. 530-538 (Year: 2004).*
Zhan et al, Improvement of Mask Based Speech Source Separation Using DNN, 2016 10th International Symposium on Chinese Spoken Language Processing, Oct. 17-20, 2016, pp. 1-5 (Year: 2016).*
Yilmaz et al, Blind Separation of Speech Mixtures via Time-Frequency Masking, IEEE Transactions on Signal Processing, vol. 52, No. 7, Jul. 7, 2004, pp. 1830-1847 (Year: 2004).*
Hyvrinen, et al. "Survey on Independent Component Analysis", Neural Computing Surveys, vol. 2, No. 4, pp. 94-128, 1999.
Lee, et al. "Blind Source Separation of More Sources then Mixtures Using Overcomplete Representations", IEEE Signal Processing Letters, vol. 6, No. 4, pp. 87-90, 1999.
Jang, et al. "Single-Channel Signal Separation Using Time-Domain Basis Functions", IEEE Signal Processing Letters, vol. 10, No. 6. pp. 168-171, 2003.
Kim, et al. "Independent Vector Analysis: An Extension of Ica to Multivariate Components", in International Conference on Independent Component Analysis and Signal Separation. Springer, pp. 165-172, 2006.
Koldovsky, et al. "Time-Domain Blind Audio Source Separation Using Advanced Ica Methods", in Eighth Annual Conference of the International Speech Communication Association, 2007.
Koldovsky et al. "Time-Domain Blind Separation of Audio Sources on the Basis of a Complete ica Decomposition of an Observation Space", IEEE Transactions on Audio, Speech, and Language Processing, vol. 19, No. 2, pp. 406-416, 2011.
Fu, et al. "End-to-End Waveform Utterance Enhancement for Direct Evaluation Metrics Optimization by Fully Convolutional Neural Networks", IEEE/ACM Transactions on Audio, Speech and Language Processing (TASLP), vol. 26, No. 9. pp. 1570-1584, 2018.
Ronneberger, et al. "U-Net: Convolutional Networks for Biomedical Image Segmentation", in International Conference on Medical Image Computing and Computer-Assisted Intervention, Springer, pp. 234-241, 2015.
Kaiser, et al. "Depthwise Separable Convolutions for Neural Machine Translation", arXiv Preprint arXiv: 1706.03059, 2017.
Sandler, et al. "Mobilenetv2: Inverted Residuals and Linear Bottlenecks", in Proceedings of the IEEE Conference on Computer Vision and Pattern Recognition, pp. 4510-4520, 2018.
He, et al. "Delving Deep into Rectifiers: Surpassing Human-Level Performance on Imagenet Classification", in Proceedings of the IEEE International Conference on Computer Vision, p. 1026-1034, 2015.
"Deep residual learning for image recognition," in Proceedings of the IEEE Conference on Computer Vision and Pattern Recognition, 2016, pp. 770-778.
Ioffe, et al. "Batch Normalization: Accelerating Deep Network Training by Reducing Internal Covariate Shift", in International Conference and Machine Learning, pp. 448-456, 2015.
Hershey, et al. "Deep Clustering: Discriminative Embeddings for Segmentation and Separation", in Acoustics, Speech and Signal Processing (ICASSP), IEEE International Conference on IEEE, pp. 31-35, 2016.
"Single-Channel Multi-Speaker Separation using Deep Clustering," Script to generate the multi-speaker dataset using wsj0, <https://www.merl.com/demos/deep-clustering>, Oct. 14, 2020.
Rix, et al. "Perceptual Evaluation of Speech Quality (pesq)—a New Method for Speech Quality Assessment of Telephone Networks and Codecs", in Acoustics, Speech, and Signal Processing, Proceedings (ICASSP'01), IEEE International Conference on, vol. 2, IEEE, pp. 749-752, 2001.
Peterson, et al. "K-Nearest Neighbor", Scholarpedia, vol. 4, No. 2, p. 1883, 2009.

(56) References Cited

OTHER PUBLICATIONS

Luo, et al. "Real-Time Single-Channel Dereverberation and Separation with Time-Domain Audio Separation Network", Proc. Interspeech, pp. 342-346, 2018.
Xu, et al. "Single Channel Speech Separation with Constrained Utterance Level Permutation Invariant Training Using Grid Lstm" in Acoustics, Speech and Signal Processing (ICASSP).
Zibulevsky, et al. "Blind Source Separation by sparse Decompsition in a Signal Dictionary", Neural Computation, vol. 13, No. 4, pp. 863-882, 2001.
Imai, et al. "Cepstral Analysis Synthesis on the Mel Frequency Scale", in Acoustics, Speech and Signal Processing, IEEE International Conference on ICASSP' 83, vol. 8, IEEE, pp. 93-96, 1983.
Romani, et al. "Tonotopic Organization of the Auditory Cortex; Pitch Versus Frequency Representation", Science, vol. 216, No. 4552, pp. 1339-1340, 1982.
Pantev, et al. "Tonotopic Organization of the Auditory Cortex: Pitch Versus Frequency Representation", Science, vol. 246, No. 4929, pp. 486-488, 1989.
Darwin, et al. "Effects of Fundamental Frequency and Vocal-Tract Length Changes on Attention to One of Two Simultaneous Talkers", The Journal of the Acoustical Society of America, vol. 114, No. 5, pp. 2913-2922, 2003.
Hershey, et al. "Super-Human Multi-Talker Speech Recognition: A Graphical Modeling Approach", Compter Speech & Language, vol. 24, No. 1, pp. 45-66, 2010.
Weng, et al. "Deep Neural Networks for Single-Channel Multi-Talker Speech Recognition", IEEE/ACM Transactions on Audio, Speech and Language Processing (TASLP), vol. 23, No. 10, pp. 1670-1679, 2015.
Qian, et al. "Single-Channel Multi-Talker Speech Recognition with Permutation Invariant Training", arXiv Preprint arXiv: 1707, 06527, 2017.
Ochi, et al. "Multi-Talker Speech Recognition Based on Blind Source Separation with Ad Hoc Microphone Array Using Smartphones and Cloud Storage", in INTERSPEECH, pp. 3369-3373, 2016.
Lei, et al. "A Novel Scheme for Speaker Recognition Using a Phonetically-Aware Deep Neural Network", in Acoustics, Speech and Signal Processing (ICASSP), IEEE International Conference on IEEE, pp. 1695-1699, 2014.
McLaren, et al. "Advances in Deep Neural Network Approaches to Speaker Recognition", In Acoustics, Speech and Signal Processing (ICASSP), IEEE International Conference on IEEE, pp. 4814-4818, 2015.
Gannot, et al. "A Consolidated Perspective on Multimicrophone Speech Enhancement and Source Separation", IEEE/ACM Transactions on Audio, Speech and Language Processing (TASLP), vol. 25, No. 4, pp. 692-730, 2017.
Chen, et al. "Cracking the Cocktail Party Problem by Multi-Beam Deep Attractor Network", in Automatic Speech Recognition and Understanding Workshop (ASRU), IEEE, pp. 437-444, 2017.
Wang, et al. "Multi-Channel Deep Clustering: Discriminative Spectral and Spatial Embeddings for Speaker-Independent Speech Separation", in Acoustics, Speech and Signal Processing (ICASSP), IEEE International Conference on. IEEE, 2018.
Mackersie, et al. "Talker Separation and Sequential Stream Segregation in Listeners with Hearing Loss Patterns Associated with Talker Gender", Journal of Speech, Language, and Hearing Research, vol. 46, pp. 912-918, 2003.
Alain, et al. "Aging and the Perceptual Organization of Sounds: A Change of Scene", Handbook of Models for Human Aging, pp. 759-769, 2006.
W.H. Organization, "Millions of People in the World have Hearing Loss That Can be Treated or Prevented", Geneva: WHO, pp. 1-17-, 2013.
Humes, et al. "Speech-Recognition Difficulties of the Hearing-Impaired Elderly The Contributions of Audibility", Journal of Speech, Language, and Hearing Research, vol. 33, pp. 726-735, 1990.
Abel, et al. "The Role of High-Frequency Hearing in Age-Related Speech Understanding Deficits", Scandinavian Audiology, vol. 29, pp. 131-138, 2000.
Middelweerd, et al. "Difficulties with Speech Intelligibility in Noise in Spite of a Normal Pure-Tone Audiogram" Original Papers. International Journal of Audiology, vol. 29, pp. 1-7, 1990.
Chmiel, et al. "Hearing Aid Use, Central Auditory Disorder, and Hearing Handicap in Elderly Persons", Journal of the American Academy of Audiology, vol. 7, pp. 190-202, 1996.
Divenyi, et al. "Audiological Correlates of Speech Understanding Deficits in Elderly Listeners with Mild-to-Moderate Hearing Loss", III. Factor Representation, Ear Hear, vol. 18, pp. 189-201, 1997.
Gordon-Salant, et al. "Effects of Stimulus and Noise Rate Variability on Speech Perception by Younger and Older Adults", The Journal of the Acoustical Society of America, vol. 115, pp. 1808-1817, 2004.
Clark, et al. "Technology for Hearing Loss—As We Know It, and As We Dream It", Disability and Rehabilitation: Assistive Technology, vol. 9, pp. 408-413, 2014.
Moria, A. "Four Transformative Patient Demands: Convenience, Size, Simplicity, and Flexibility", Hearing Review, vol. 18, pp. 36-42, 2011.
Mesgarani, et al. "Selective Cortical Representation of Attended Speaker in Multi-Talker Speech Perception", Nature vol. 485, pp. 233-U118, doi:10.1038/Nature11020, 2012.
O'Sullivan, et al. Attentional Selection in a Cocktail Party Environment Can Be Decoded from Single-Trial EEG. Cerebral Cortex, vol. 25, pp. 1697-1706, doi:10.1093/cercor/bht355, 2015.
Van Eyndhoven, et al. "EEG-Informed Attended Speaker Extraction from Recorded Speech Mixtures with Application in Neuro-Steered Hearing Prostheses", arXiv Preprint arXiv: 1602.05702, (2016).
Ekin, et al. "An Alternative Approach for Auditory Attention Tracking Using Sigle-Trial EEG", IEEE International Conference on Acoustics, Speech and Signal Processing, (ICASSP), p. 729-733, 2016.
Aroudi, et al. "Auditory Attention Decoding with EEG Recordings Using Noisy Acoustic Reference Signal", IEEE International Conference on Acoustics, Speech and Signal Processing (ICASSP), pp. 694-698, 2016.
Mirkovic, et al. "Decoding the Attended Speech Stream with Multi-Channel EEG: Implications for Online, Daily-Life Applications", Journal of Neural Engineering, vol. 12, 046007, 2015.
Biesmans, et al. "Auditory-Inspired Speech Envelope Extraction Methods for Improved EEG-Based Auditory Attention Detection in a Cocktail Party Scenario", 2015.
Cognitive Control of a Hearing Aid, <https://cocoha.org/the-need/>, 2016.
Bach, et al. "Learning Spectral Clustering, with Application to Speech Separation", The Journal of Machine Learning Research, vol. 7. Pages 1963-2001, 2006.
Krishnan, et al. "Segregating Complex Sound Sources Through Temporal Coherence", Plos Comput Biol, vol. 10, e1003985, 2014.
Schmidt, et al. "Single-Channel Speech Separation Using Sparse Non-Negative Matrix Factorization", Spoken Language Processing, ISCA International Conference on (INTERSPEECH), 2016.
Weninger, et al. "Speech Enhancement with LSTM Recurrent Neural DNNs and its Application to Noise-Robust ASR", Latent Variable Analysis and Signal Separation, Springer, pp. 91-99, 2015.
Weninger, et al. Discriminatively Trained Recurrent Neural DNNs for Single-Channel Speech Separation", Signal and Information Processing", IEEE Global Conference on, pp. 577-581, 2014.
Mesgarani, et al. "Influence of Context and Behavior on Stimulus Reconstruction From Neural Activity in Primary Auditory Cortex", Journal of Neurophysiology, vol. 102, pp. 3329-3339, doi: 10.1152/jn.91128.2008, 2009.
Pasley, et al. Reconstructing Speech from Human Auditory Cortex. PLoS. Biol. vol. 10, doi: 10.1371/journal.pbio.1001251, 2012.
G.tec <http://www.gtec.at/Products/Hardware-and-Accessories/g.Hlamp-Specs-Features>; Web page with description of g.Hlamp multi-channel amplifier by g.tec, Oct. 14, 2020.
Buzsàki, et al. "The Origin of Extracellular Fields and Currents—EEG, ECoG, LFP and Spikes", Nat. Rev. Neurosci. vol. 13, pp. 407-420, 2012.

(56) References Cited

OTHER PUBLICATIONS

Akram, et al. "A State-Space Model for Decoding Auditory Attentional Modulation from MEG in a Competing Speaker Environment", Advances in Neural Information Processing Systems, pp. 460,468.
Bregman, A. "Auditory Scene Analysis: The Perceptual Organization of Sound", ed: MIT Press, Cambridge, MA 1990.
Peelle, et al. "The Neural Consequences of Age-Related Hearing Loss", Trends in Neurosciences, 2016.
Ding, et al. "Neural Coding of Continuous Speech in Auditory Cortex During Monaural and Dichotic Listening", Journal of Neurophysiology, vol. 107, pp. 78-89, 2012.
Ding, et al. "Emergence of Neural Encoding of Auditory Objects While Listening to Competing Speakers", Proceedings of the National Academy of Sciences of the United States of America, vol. 109, pp. 11854-11859, 2012.
Horton, et al. "Suppression of Competing Speech Through Entrainment of Cortical Oscillations", Journal of Neurophysiology, vol. 109, pp. 3082-3093, 2013.
Power, et al. "At What Time is the Cocktail Party? A Late Locus of Selective Attention to Natural Speech", European Journal of Neuroscience, vol. 35, pp. 1497-1503, 2012.
Golumbic, et al. "Mechanisms Underlying Selective Neuronal Tracking of Attended Speech at a Cocktail Party", Neuron, vol. 77, pp. 980-991, 2013.
Horton, et al. "Envelope Responses in Single-Trial EEG Indicate Attended Speaker in a cocktail party", J. Neural Eng, vol. 11, p. 046015, 2014.
O'Sullivan, et al. "Improved Decoding of Attentional Selection in a Cocktail Party Environment with EEG via Automatic Selection Independent Components", in Engineering in Medicine and Biology Society (EMBC), 37th Annual International Conference of the IEEE, pp. 5740-5743, 2015.
Dijkstra, et al. "Identifying the Attended Speaker Using Electrocorticographic (ECoG) Signals", Brain-Computer Interfaces, vol. 2, pp. 161-173, 2015.
Das, et al. "The Effect of Head-Related Filtering and Ear-Specific Decoding Bias on Auditory Attention Detection", 2016.
Bleichner, et al. "Identifying Auditory Attention with ear-EEG: cEEGrid Versus High-Density Cap-EEG Comparison", Journal of Neural Engineering, vol. 13, p. 066004, 2016.
Haghighi, et al. "Toward a Brain Interface for Tracking Attended Auditory Sources", in Machine Learning for Signal Processing (MLSP), IEEE 26th International Workshop, pp. 1-5, 2016.
Fiedler, et al. "Ear-EEG Allows Extraction of Neural Responses in Challenging Listening Scenarios—A Future Technology for Hearing Aids?", in Engineering in Medicine and Biology Society (EMBC), IEEE 38th Annual International Conference, pp. 5697-5700, 2016.
Paul, et al. "The Design for the Wall Street Journal-Based CSR Corpus", in Proceedings of the Workshop on Speech and Natural Language, pp. 357-362, 1992.
Lotia, et al. "A Review of Various Score Normalization Techniques for Speaker Identification System", International Journal of Advances in Engineering & Technology, vol. 3, p. 650, 2012.
Loizou, P.C. "Speech Quality Assessment", in Multimedia Analysis, Processing and Communications, ed: Springer, pp. 623-654, 2011.
Ma, et al. "Objective Measures for Predicting Speech Intelligibility in Noisy Conditions based on New Band-Importance Functions", The Journal of the Acoustical Society of America, vol. 125, pp. 3387-3405, 2009.
Rothauser, et al. "IEEE Recommended Practice for Speech Quality Measurements", IEEE Trans. Audio Electroacoust, vol. 17, pp. 225-246, 1969.
Loizou et al. "Reasons Why Current Speech-Enhancement Algorithms Do Not Improve Speech Intelligibility and Suggested Solutions", IEEE Transactions on Audio, Speech, and Language Processing, vol. 19, pp. 47-56, 2011.
Deng, et al. "An Overview of Noise-Robust Automatic Speech Recognition", IEEE/ACM Transactions on Audio, Speech, and Language Processing, vol. 22, pp. 745-777, 2014.

Brumm, et al. "The Evolution of the Lombard Effect: 100 Years of Psychoacoustic Research", Behaviour, vol. 148, pp. 1173-1198, 2011.
Brungart, et al. "Informational and Energetic Masking Effects in the Perception of Multiple Simultaneous Talkers", The Journal of the Acoustical Society of America, vol. 110, pp. 2527-2538, 2001.
Eyndhoven et al. "EEG-informed attended speaker extraction from recorded speech mixtures with application in neuro-steered hearing prostheses." In: IEEE Trans. Biomedical Engineering, 2016, Feb. 18, 2016 [online].
Schminky MM, Baran JA. Central Auditory Processing Disorders—An Overview of Assessment and Management Practices <http://www.tsbvi.edu/seehear/spring00/centralauditory.htm>. Deaf-Blind Perspectives. 1999.
Mejia J, Dillion H, Hoesel RV, Beach E, Glyde H, Yeend I, Beechey T, Mcleeland M, O'Brien A, Buchholz J, Sharma M, Valderrama J, Williams W.—Loss of speech perception in noise causes and compensation <https://www.researchgate.net/publication/301770799_ISAAR2015_Paper>. International Symposium on Auditory and Audiological Research 2015 Paper. May 2016.
Lopez MA, Pomares H, Prieto A, Pelayo F. Signal Processing and Perceptrons in an Auditory based Brain-Computer Interface Eighth International Conference on Hybrid Intelligent Systems. Sep. 10-12, 2008. pp. 781-786.
Healy, E., Yoho, S. "An algorithm to improve speech recognition in noise for hearing-impaired listeners." Journal of Acoustical Society of America. vol. 134 / Issue 4. pp. 3029-3038, Oct. 2013.
Nima Mesgarani, "Neurophysiology of robust speech perception in human superior temporal gyrus." NIH Project #5R01DC014379-02. Feb. 24, 2016.
Nima Mesgarani, "Biologically inspired neural network models for robust speech processing." NSF Grant # 1555079. Jun. 1, 2016.
Yanhui, Tu & Du, Jun & Xu, Yong & Dai, Lirong & Lee, C.-H. (2015). Deep neural network based speech separation for robust speech recognition. International Conference on Signal Processing Proceedings, ICSP. 2015. 532-536. 10.1109/ICOSP.2014.7015061.
C. Kwan et al., "Speech separation algorithms for multiple speaker environments," 2008 IEEE International Joint Conference on Neural Networks (IEEE World Congress on Computational Intelligence), Hong Kong, 2008, pp. 1644-1648, doi: 10.1109/IJCNN.2008.4634018.
Narayanan and D. Wang, "Improving Robustness of Deep Neural Network Acoustic Models via Speech Separation and Joint Adaptive Training," in IEEE/ACM Transactions on Audio, Speech, and Language Processing, vol. 23, No. 1, pp. 92-101, Jan. 2015, doi: 10.1109/TASLP.2014.2372314.
Pombo N, Araújo P, Viana J, da Costa MD. Evaluation of a ubiquitous and interoperable computerised system for remote monitoring of ambulatory post-operative pain: a randomised controlled trial. Technol Health Care. 2014;22(1):63-75. doi:10.3233/THC-130774.
Y. Tu, J. Du, Y. Xu, L. Dai and C. Lee, "Speech separation based on improved deep neural networks with dual outputs of speech features for both target and interfering speakers," The 9th International Symposium on Chinese Spoken Language Processing, Singapore, 2014, pp. 250-254, doi: 10.1109/ISCSLP.2014.6936615.
C. Weng, D. Yu, M. L. Seltzer and J. Droppo, "Deep Neural Networks for Single-Channel Multi-Talker Speech Recognition," in IEEE/ACM Transactions on Audio, Speech, and Language Processing, vol. 23, No. 10, pp. 1670-1679, Oct. 2015, doi: 10.1109/TASLP.2015.2444659.
N. Mesgarani and E.F. Chang, "Selective cortical representation of attended speaker in multi-talker speech perception," Nature, vol. 485, pp. 233-U118, May 2012.
G.E. Dahl, D. Yu, L. Deng, and A. Acero, "Context-dependent pre-trained deep neural networks for large-vocabulary speech recognition," in IEEE Trans. on Audio, Speech and Language Processing, 2012, vol. 20.
Huang, et al. "Joint Optimization of Masks and Deep Recurrent Neural Networks for Monaural Source Separation", IEEE/ACM Transactions on Audio, Speech and Language Processing (TASKP), vol. 23, No. 12, pp. 1-12, 2015.

(56) References Cited

OTHER PUBLICATIONS

Zhang, et al. "A Deep Ensemble Learning Method for Monaural Speech Separation", IEEE/ACM Transactions on Audio, Speech and Language Processing (TASLP), vol. 24, No. 5, pp. 967-977, 2016.
Isik, et al. "Single-Channel Multi-Speaker Separation Using Deep Clustering", ArXiv Preprint arXiv: 1607. 02173, 2016.
Kolbaek, et al. "Multitalker Speech Separation with Utterance-Level Permutation Invariant Training of Deep Recurrent Neural Networks", IEEE/ACM Transactions on Audio, Speech, and Language Processing, vol. 25, No. 10, pp. 1901-1913, 2017.
Chen, et al. "Deep Attractor Network for Single-Microphone Speaker Separation", In Acoustics, Speech and Signal Processing (ICASSP), IEEE International Conference on IEEE, pp. 246-250, 2017.
Erdogan, et al. "Phase-Sensitive and Recognition-Boosted Speech Separation Using Deep Recurrent Neural Networks", in Acoustics, Speech and Signal Processing (ICASSP), IEEE International Conference on. IEEE, pp. 708-712, 2015.
Williamson, et al. "Complex Ratio Masking for Monaural Speech Separation", IEEE/ACM Transactions on Audio, Speech, and Language Processing, vol. 24, No. 3, pp. 483-492, 2016.
Luo, et al. "Deep Clustering and Conventional Networks for Music Separation: Stronger Together", in Acoustics, Speech and Signal Processing (ICASSP), IEEE International Conference on IEEE, pp. 61-65, 2017.
Sainath, et al. "Learning the Speech Front-End with Raw Waveform Cldnns", in Sixteenth Annual Conference of the International Speech Communication Association, 2015.
Ghahremani, et al. "Acoustic Modelling from the Signal Domain Using Cnns", in INTERSPEECH, pp. 3434-3438, 2016.
Van den Oord, et al. "Wavenet: A Generative Model for Raw Audio", arXiv Preprint arXiv: 1609.03499, 2016.
Mehri, et al. "Samplernn: An Unconditional End-to-End Neural Audio Generation Model", arXiv Preprint arXiv: 1612.07837, 2016.
Pascual, et al. "Segan: Speech Enhancement Generative Adversarial Network", arXiv Preprint arXiv: 1703.09452, 2017.
Venkataramani, et al. "End-to-End Source Separation with Adaptive Front-Ends", arXiv Preprint arXiv: 1705.02514, 2017.
Wang, et al. "Nonnegative Least-Correlated Component Analysis for Separation of Dependent Sources by Volume Maximization", IEEE Transactions on Pattern Analysis and Machine Intelligence, vol. 32, No. 5, pp. 875-888, 2010.
Ding, et al. "Convex and Semi-Nonnegative Matrix Factorizations", IEEE Transactions on Pattern Analysis and Machine Intelligence, vol. 32, No. 1, pp. 45-55, 2010.
Hosseini-Asl, et al. "Deep Learning of Part-Based Representation of Data Using Sparse Autoencoders with Nonnegativity Constraints", IEEE Transactions on Neural Networks and Learning Systems, vol. 27, No. 12, pp. 2486-2498, 2016.
Lemme, et al. "Online Learning and Generalization of Parts-Based Image Representations by Non-Negative Sparse Autoencoders", Neural Networks, vol. 33, pp. 194-203, 2012.
Chorowski, et al. "Learning Understandable Neural Networks with Nonnegative Weight Constraints", IEEE Transactions on Neural Networks and Learning Systems, vol. 26, No. 1, pp. 62-69, 2015.
Dauphin, et al. "Language Modeling and Gated Convolutional Networks", arXiv Preprint arXiv: 1612.08083, 2016.
Ba, et al. "Layer Normalization", arXiv Preprint arXiv: 1607.06450, 2016.
He, et al. "Identity Mappings in Deep Residual Networks", in European Conference on Computer Vision. Springer, pp. 630-645, 2016.
Kingma, et al. "Adam: A Method for Stochastic Optimization", arXiv Preprint arXiv: 1412.6980, 2014.
Bengio, et al. "Curriculum Learning" in Proc. ICML, pp. 41-48, 2009.
Vincent, et al. "Performance Measurement in Blind Audio Source Separation", IEEE Transactions on Audio, Speech, and Language Processing, vol. 14, No. 4, pp. 1462-1469, 2006.

Smaragdis et al. "A neural network alternative to non-negative audio models," in Acoustics, Speech and Signal Processing (ICASSP), 2017 IEEE International Conference on. IEEE, 2017, pp. 86-90.
Dumoulin et al. "A Guide to convolution arithmetic for deep learning," arXiv preprint arXiv: 1603.07285, 2016.
Nagamine, et al. "Understanding the Representation and Computation of Multilayer Perceptrons: A Case Study in Speech Recognition", in International Conference on Machine Learning, pp. 2564-2573, 2017.
Wang, et al. "Supervised Speech Separation Based on Deep Learning: An Overview", IEEE/ACM Transactions on Audio, Speech, and Language Processing, 2018.
Lu, et al. "Speech Enhancement Based on Deep Denoising Autoencoder", in Interspeech, pp. 436-440, 2013.
Xu, et al. "An Experimental Study on Speech Enhancement Based on Deep Neural Networks", IEEE Signal Processing Letters, vol. 21, No. 1, pp. 65-68, 2014.
"A regression approach to speech enhancement based on deep neural networks," IEEE/ACM Transactions on Audio, Speech and Language Processing (TASLP), pp. 1-13, 2013.
Wang, et al. "Alternative Objective Functions for Deep Clustering", in Proc. IEEE International Conference on Acoustics, Speech and Signal Processing (ICASSP), 2018.
Wang, et al. "End-to-End Speech Separation with Unfolded Iterative Phase Reconstruction", arXiv Preprint arXiv: 1804.10204. 2018.
Zhu, et al. "CBLDNN-Based Speaker-Independent Speech Separation via Generative Adversarial Training", in Acoustics, Speecj and Signal Processing (ICASSP), IEEE International Conference on IEEE, 2018.
Griffin, et al. "Signal Estimation From Modified Short-Time Fourier Transform", IEEE Transactions on Acoustics, Speech, and Signal Processing, vol. 32, No. 2, pp. 236-243, 1984.
LeRoux, et al. "Explicit Consistency Constraints for Stft Spectrograms and Their Application to Phase Reconstruction", in SAPA@ INTERSPEECH, pp. 23-28, 2008.
Jansson, et al. "Singing Voice Separation with Deep U-Net Convolutional Networks", in 18th International Society for Music Information Retrieval Conference, pp. 23-27, 2017.
Choi, et al. "Blind Source Separation and Independent Component Analysis: A Review", Neural Information Processing—Letters and Reviews, vol. 6, No. 1, pp. 1-57, 2005.
Yoshii, et al. "Beyond Nmf: Time-Domain Audio Source Separation Without Phase Reconstruction", in ISMIR, pp. 369-374, 2013.
Stoller, et al. "Wave-u-net: A Multi-Scale Neural Network for End-to-End Audio Source Separation", arXiv Preprint arXiv: 1806. 03185,2018.
Luo, et al. "Tasnet: Time-Domain Audio Separation Network for Real-Time, Single-Channel Speech Separation", in Acoustics, Speech and Signal Processing (ICASSP), IEEE International Conference on IEEE, 2016.
Lea, et al. "Temporal Convolutional Networks: A Unified Approach to Action Segmentation", in European Conference on Computer Vision. Springer, pp. 47-54, 2016.
Rene, et al. "Temporal Convolutional Networks for Action Segmentation and Detection", in IEEE International Conference on Computer Vision (ICCV), 2017.
Bai, et al. "An Empirical Evaluation of Generic Convolutional and Recurrent Networks for Sequence Modeling", arXiv Preprint arXiv: 1803.01271, 2018.
Chollet, et al. "Xception: Deep Learning with Depthwise Separable Convolutions", arXiv Preprint, 2016.
Howard, et al. "Mobilenets: Efficient Convolutional Neural Networks for Mobile Vision Applications", arXiv Preprint arXiv: 1704.04861, 2017.
Wang, et al. "On Ideal Binary Mask as the Computational Goal of Auditory Scene Analysis", in Speech Separation by Humans and Machines, Springer, pp. 181-197, 2005.
Li, et al. "On the Optimality of Ideal Binary Time-Frequency Masks", Speech Communication, vol. 51, No. 3, pp. 230-239, 2009.
Wang, et al. "On Training Targets for Supervised Speech Separation", IEEE/ACM Transactions on Audio, Speech and Language Processing (TASLP), vol. 22, No. 12, pp. 1849-1858, 2014.

(56) References Cited

OTHER PUBLICATIONS

S. Hasim Senior A., and F. Beaufays, "Long short-term memory recurrent neural network architectures for large scale acoustic modeling," in Interspeech 2014. ISCA, 2014.

A. Senior, S. Hasim, F.C. Quitry, T.N. Sainath, and K. Rao, "Acoustic modelling with cd-ctc-smbr lstm rnns," in ASRU 2015. IEEE, 2015.

Zhuo Chen, Shinji Watanabe, Hakan Erdogan, and John R. Hershey, "Speech enhancement and recognition using multi-task learning of long short-term memory recurrent neural networks," ISCA, 2015.

Takaaki Hori, Zhuo Chen, Hakan Erdogan, John R. Hershey, Jonathan Le Roux, Vikramjit Mitra, and Shinji Watanabe, "The merl/sri system for the 3rd chime challenge using beamforming robust feature extraction, and advanced speech recognition," in 2015 IEEE Workshop on Automatic Speech Recognition and Understanding (ASRU). IEEE, 2015, pp. 475-481.

E Colin Cherry, "Some experiments on the recognition of speech, with one and with two ears," The Journal of the acoustical society of America, vol. 25, No. 5, pp. 975-979, 1953.

Dong Yu, Morten Kolbaek, Zheng-Hua Tan, and Jesper Jensen, "Permutation invariant training of deep models for speaker-independent multi-talker speech separation," arXiv preprint arXiv: 1607.00325, 2016.

Patricia K. Kuhl, "Human adults and human infants show a perceptual magnet effect," Perception & psychophysics, 50.2 (1991): 93-107.

Dzmitry Bahdanau, Kyunghyun Cho, and Yoshua Bengio, "Neural machine translation by jointly learning to align and translate," arXiv preprint arXiv: 1409.0473, 2014.

Kyunghyun Cho, Aaron Courville, and Yoshua Bengio, "Describing multimedia content using attention-based encoder-decoder networks," IEEE Transactions on Multimedia, vol. 17, No. 11, pp. 1875-1886, 2015.

Sepp Hochreiter and Jurgen Schmidhuber, "Long-short-term memory," Neural computation, vol. 9, No. 8, pp. 1735-1780, 1997.

Tijmen Tieleman and Geoffrey Hinton, "Lecture 6.5-rmsprop," COURSERA: Neural networks for machine learning, 2012. http://www.cs.toronto.edu/~tijmen/csc321/slides/lecture_slides_lec6.pdf, Date of Download: Oct. 14, 2020.

\* cited by examiner

THE EFFECT OF DIFFERENT CONFIGURATIONS IN CONV-TASNET.

| N | L | B | H | P | X | R | Normali-zation | Causal | Receptive field(s) | SI-SNRi (dB) | SDRi (dB) |
|---|---|---|---|---|---|---|---|---|---|---|---|
| 128 | 40 | 64 | 128 | 3 | 7 | 2 | BN | × | 1.28 | 9.2 | 9.6 |
| 128 | 40 | 64 | 256 | 3 | 7 | 2 | BN | × | 1.28 | 10.0 | 10.4 |
| 128 | 40 | 128 | 256 | 3 | 7 | 2 | BN | × | 1.28 | 10.4 | 10.8 |
| 256 | 40 | 128 | 256 | 3 | 7 | 2 | BN | × | 1.28 | 10.5 | 10.9 |
| 256 | 40 | 128 | 512 | 3 | 7 | 2 | BN | × | 1.28 | 11.3 | 11.6 |
| 256 | 40 | 256 | 512 | 3 | 7 | 2 | BN | × | 1.28 | 11.3 | 11.7 |
| 256 | 40 | 256 | 512 | 3 | 6 | 4 | BN | × | 1.27 | 11.7 | 12.1 |
| 256 | 40 | 256 | 512 | 3 | 8 | 2 | BN | × | 2.56 | 12.2 | 12.6 |
| 256 | 40 | 256 | 512 | 3 | 7 | 4 | BN | × | 2.55 | 12.6 | 13.0 |
| 256 | 20 | 256 | 512 | 3 | 8 | 4 | BN | × | 2.55 | 14.3 | 14.7 |
| 256 | 20 | 256 | 512 | 3 | 8 | 4 | cLN | × | 2.55 | 14.0 | 14.4 |
| 256 | 20 | 256 | 512 | 3 | 8 | 4 | gLN | × | 2.55 | 14.6 | 15.0 |
| 256 | 20 | 256 | 512 | 3 | 8 | 4 | BN | ✓ | 2.55 | 10.8 | 11.2 |
| 256 | 20 | 256 | 512 | 3 | 8 | 4 | cLN | ✓ | 2.55 | 10.5 | 10.9 |

| Method | Causal | SI-SNRi (dB) | SDRi (dB) | PESQ |
|---|---|---|---|---|
| DAN-LSTM [13] | No | 9.1 | 9.5 | 2.73 |
| uPIT-LSTM [18] | Yes | --- | 7.0 | --- |
| ODAN | Yes | 9.0 | 9.4 | 2.70 |

Comparison of speech separation accuracy of ODAN with two other methods for separating two-speaker mixtures (WSJ0-mix2 dataset).

2810

| Method | Causal | SI-SNRi (dB) | SDRi (dB) | PESQ |
|---|---|---|---|---|
| DAN-LSTM [13] | No | 7.00 | 7.42 | 2.13 |
| uPIT-BLSTM [18] | No | --- | 7.4 | --- |
| DPCL++ [24] | No | 7.1 | --- | --- |
| ODAN | Yes | 6.7 | 7.2 | 2.03 |

Comparison of speech separation accuracy of ODAN with three noncausal methods for separating three speaker mixtures (WSJ0-mix3 dataset). The separation accuracy of ODAN, which is the only causal system, is slightly worse but comparable to the other three methods.

2820

FIG. 28

SYSTEMS AND METHODS FOR SPEECH SEPARATION AND NEURAL DECODING OF ATTENTIONAL SELECTION IN MULTI-SPEAKER ENVIRONMENTS

CROSS-REFERENCE TO RELATED APPLICATIONS

This application is a continuation-in-part (CIP) application of, and claims priority to, International Application No. PCT/US2017/037186, entitled "NEURAL DECODING OF ATTENTIONAL SELECTION IN MULTI-SPEAKER ENVIRONMENTS," and filed Jun. 13, 2017, which in turn claims the benefit of, and priority to U.S. Provisional Patent Application Ser. Nos. 62/480,005, entitled "DEEP ATTRACTOR NETWORK FOR SINGLE CHANNEL SPEECH SEPARATION" and filed Mar. 31, 2017, 62/429,549, entitled "NEURAL DECODING OF ATTENTIONAL SELECTION IN MULTI-SPEAKER ENVIRONMENTS WITHOUT ACCESS TO SEPARATED SOURCES" and filed Dec. 2, 2016, and 62/349,976, entitled "NEURAL DECODING OF ATTENTIONAL SELECTION IN MULTI-SPEAKER ENVIRONMENTS WITHOUT ACCESS TO SEPARATED SOURCES" and filed Jun. 14, 2016. The present CIP application also claims priority to U.S. Provisional application No. 62/578,324, entitled "Deep Waveform Decomposition for Real-Time Single-Channel Speech Separation" and filed Oct. 27, 2017, U.S. Provisional application No. 62/635,203, entitled "DEEP WAVEFORM DECOMPOSITION FOR REAL-TIME SINGLE-CHANNEL SPEECH SEPARATION" and filed Feb. 26, 2018, and U.S. Provisional application No. 62/733,215, entitled "TASNET: SURPASSING IDEAL TIME-FREQUENCY MASKING FOR SPEECH SEPARATION" and filed Sep. 19, 2018. The contents of all of the above-identified previously filed applications are incorporated herein by reference in their entireties.

STATEMENT REGARDING FEDERALLY SPONSORED RESEARCH

This invention was made with government support under grant DC014279 awarded by the National Institutes of Health and grant 1555079 awarded by the National Science Foundation. The government has certain rights in the invention.

BACKGROUND

In a natural auditory environment, most people can generally attend to (i.e., focus on) a particular speaker out of many. However, this task is challenging for persons suffering from peripheral and central auditory pathway disorders. This challenge is exacerbated by the fact that real-world speech communication often takes place in crowded environments. Any speech processing system that is designed to work in such conditions therefore requires the ability to separate speech of different speakers.

SUMMARY

Described herein are implementations to process multi-source sound signals (e.g., speech signals originating from multiple speakers) based on neural signals measured for a person observing (listening to) the multi-source signal. For example, the neural signal can be used to determine which source (speaker) the listener is attending to (i.e., attempting to focus on), to thus allow signal processing that amplifies or enhances signals originating from the attended-to source, and/or attenuates the other, non-attendant, signals. The implementations may use one of several multi-source signal separation approaches or frameworks to separate the multi-source combined (mixed) signal (which may be obtained using a single sensor, such as a single microphone) into individual signals that correspond to the various sources, and then use the observer's neural signals to select the likely individual signal that is to be enhanced. Speech separation approaches can also be used with other applications, such as to support surveillance systems, support virtual reality and augmented reality systems, etc.

One signal separation approach is the deep attractor network (DANet) approach for separating multiple sound sources (e.g. speakers) from a single channel recording. In some implementations, the DANet deep learning framework, which can be used for single channel speech separation, creates attractor points in high dimensional embedding space of the acoustic signals which pull together time-frequency bins corresponding to each source. Attractor points are created, in some embodiments, by finding the centroids of the sources in the embedding space, which are subsequently used to determine the similarity of each bin in the mixture to each source. The network is trained to minimize the reconstruction error of each source by optimizing the embeddings.

Another of the multi-source signal separation approaches includes implementations for a deep learning speech separation system that directly operates on sound waveforms. In some embodiments, a Time-domain Audio Separation Network (TasNet) is used to directly model a signal in the time-domain using an encoder-decoder framework, and to perform source separation on nonnegative encoder outputs. Such implementations remove the frequency decomposition stage and reduce the separation problem to estimation of source masks on encoder outputs which is then synthesized by the decoder. These implementations generally outperform state-of-the-art causal and non-causal speech separation systems (such as STFT-based systems), reduce the computational cost of speech separation, and reduce the minimum required latency of the output. This makes TasNet suitable for applications where low-power, real-time implementation is desirable, such as in hearable and telecommunication devices.

Another type of speech separation systems that may be used in conjunction with attentional selection (based on neural decoding) implementations is the time-domain audio separation network, that uses a convolutional encoder to create a representation of the signal that is optimized in order to extract individual speakers (this type of speech separation system is referred to herein as "convolutional-TasNet" or "Conv-TasNet"). In example embodiments, speaker extraction is achieved by applying a weighting function (mask) to the encoder output. The modified encoder representation is then inverted to the sound waveform using a linear decoder. The masks are found using a temporal convolution network comprising of dilated convolutions, which allow the network to model the long-term dependencies of the speech signal.

An additional multi-source signal separation approach that may be implemented is one that automatically separate speakers in mixed audio without any need for prior training on the speakers. This approach, referred to as online deep attractor network (ODAN) automatically separate unseen sources, and therefore can generalize to new speakers. A further approach that may be used is one based on using a neural network to derive multiple speaker spectrograms from the spectrogram of a combined (mixed) sound/speech signal. Neural signals measured for a person can be used to produce an neural-signals-based spectrogram that is then compared to the multiple spectrograms derived from the spectrogram for the combined signal, so as to select one of the multiple derived spectrograms (based on which a reconstructed separated speech signal can be generated).

Thus, in some variations, a method is provided that includes obtaining, by a device, a combined sound signal for signals combined from multiple sound sources in an area in which a person is located, and applying, by the device, a speech-separation processing to the combined sound signal from the multiple sound sources to derive a plurality of separated signals that each contains signals corresponding to different groups of the multiple sound sources. The method further includes obtaining, by the device, neural signals for the person, the neural signals being indicative of one or more of the multiple sound sources the person is attentive to, and selecting one of the plurality of separated signals based on the obtained neural signals for the person.

Embodiments of the method may include at least some of the features described in the present disclosure, including one or more of the following features.

Obtaining the neural signals for the person may include obtaining one or more of, for example, electrocorticography (ECoG) signals for the person, neural measurements via a non-invasive scalp, and/or in-ear EEG recordings.

The method may further include processing the selected one of the plurality of separated sound signals, including performing one or more of, for example, amplifying the selected one of the plurality of separated signals, and/or attenuating at least one non-selected signal from the plurality of separated signals.

Obtaining the combined sound signal for the multiple sound sources may include receiving the combined sound signal for the multiple sound sources at a single microphone coupled to the device.

Applying the speech-separation processing to the combined sound signal from the multiple sound sources to derive the plurality of separated signals may include applying neural-network-based speech-separation processing to the combined sound signal from the multiple sound sources to derive the plurality of separated signals.

Applying the neural-network-based speech-separation processing to the combined sound signal from the multiple sound sources may include providing the combined sound signal from the multiple sound sources to a deep neural network (DNN) configured to identify individual sound sources from the combined sound signal.

The method may further include generating a sound spectrogram from the combined sound signal, and applying the neural-network-based speech-separation processing to the generated spectrogram to derive multiple resultant speaker spectrograms.

Selecting the one of the plurality of separated sound signals based on the obtained neural signals for the person may include generating an attended speaker spectrogram based on the neural signals for the person, comparing the attended speaker spectrogram to the derived multiple resultant speaker spectrograms to select one of the multiple resultant speaker spectrograms, and transforming the selected one of the multiple resultant speaker spectrograms into an acoustic signal.

Comparing the attended-speaker spectrogram to the derived multiple resultant speaker spectrograms may include comparing the attended speaker spectrogram to the derived multiple resultant speaker spectrograms using normalized correlation analysis.

The combined sound signal may define a time-frequency embedding space, and applying the neural-network-based speech-separation processing to the combined sound signal may include determining respective reference points for each of the multiple sound sources, with the reference points representing locations of the sound sources in the embedding space for the combined sound signal, deriving masks for the determined reference points, and extracting at least one of the multiple sound sources using at least one of the derived masks.

Determining the respective reference points may include determining the respective reference points using a deep neural network.

Deriving the masks may include computing similarity between embedded time-frequency points within the embedding space and the determined respective reference points.

The reference points may include attractor points in the embedding space.

Applying the neural-network-based speech-separation processing to the combined sound signal may include dividing the combined sound signal into non-overlapping segments, transforming the non-overlapping segments into respective weighted sums of a learnable overcomplete basis of signals, with weight coefficients for the respective weighted sums being non-negative, performing neural-network-based processing on the respective weighted sums of the learnable overcomplete basis of signals to derive a plurality of mask matrices corresponding to different groups of the multiple sound sources, and estimating a plurality of reconstructed sounds signals from the derived plurality of mask matrices corresponding to the different groups of the multiple sound sources.

Transforming the non-overlapping segments into the respective weighted sums may include estimating the respective weighted sums of the learnable overcomplete basis of signals using a gated 1-D convolution layer according to $w_k = \text{ReLU}(x_k * U) \odot \sigma(x_k * V)$, $k=1, 2, \ldots, K$, where $U \in R^{N \times L}$ and $V \in R^{N \times L}$ are N vectors with length L, $w_k \in R^{1 \times N}$ is a mixture weight vector for segment k, $\sigma$ denotes a Sigmoid activation function, and * denotes a convolution operator.

Performing neural-network-based processing on the respective weighted sums to derive the plurality of mask matrices may include inputting the respective weighted sums of the learnable overcomplete basis of signals to a deep long-short term network (LSTM) followed by a fully connected layer with Softmax activation function for mask generation.

Estimating the plurality of reconstructed sounds signals may include computing a source weight matrix, $D_i$, according to $D_i = W \odot M_i$, where $D_i = [d_{i,1}, \ldots, d_{i,K}] \in R^{K \times N}$ is the weight matrix for source I, and synthesizing a time-domain synthesis of the sources by multiplying the weight matrix $D_i$ with basis signals $B \in R^{N \times L}$.

Applying the speech-separation processing to the combined sound signal from the multiple sound sources to derive the plurality of separated signals may include representing the combined sound signal as a time-frequency mixture signal in a time-frequency space, projecting the time-frequency mixture signal into an embedding space comprising multiple embedded time-frequency bins, tracking respective reference points for each of the multiple sound sources, with the reference points representing locations of the multiple sound sources in the embedding space, based at least in part on previous locations of the respective reference points at one or more earlier time instances, deriving masks for the tracked respective reference points, and extracting at least one of the multiple sound sources using at least one of the derived masks.

Projecting the time-frequency mixture signal into the embedding space may include processing the time-frequency mixture signal with a neural network comprising a plurality of stacked long short-term memory (LSTM) layers, coupled to a fully connected network.

The reference points may include attractor points in the embedding space.

Tracking the respective reference points may include computing distances of current embedded time-frequency bins to previous locations of the respective reference points at an earlier time instance, and assigning the each of the current embedded time-frequency bins to respective ones of the multiple sources based on the computed distances.

The method may further include updating current locations of the reference points based, at least in part, on assignments of the each of the current embedded time-frequency bins to the respective ones of the multiple sources. Deriving masks for the tracked reference points may include generating the masks based, at least in part, on the updated current locations of the references points.

Applying the speech-separation processing to the combined sound signal from the multiple sound sources to derive the plurality of separated signals may include dividing the combined sound signal into a plurality of segments, transforming the plurality of segments into a plurality of corresponding encoded segments represented in an intermediate feature space, estimating, for each of the plurality of corresponding encoded segments, multiple mask functions for respective ones of the multiple sound sources by passing the each of the plurality of corresponding encoded segments through a stacked dilated convolutional network, multiplying the estimated mask functions with the respective one of the plurality of corresponding encoded segments to produce respective resultant multiple masked segments, and generating separated estimates of the signals from the multiple sound sources based on the respective resultant multiple masked segments.

In some variations, a system is provided that includes at least one microphone to obtain a combined sound signal for signals combined from multiple sound sources in an area in which a person is located, one or more neural sensors to obtain neural signals for the person, with the neural signals being indicative of one or more of the multiple sound sources the person is attentive to, and a controller coupled to the at least one microphone and the one or more neural sensors. The controller is configured to apply speech-separation processing to the combined sound signal from the multiple sound sources to derive a plurality of separated signals that each contains signals corresponding to different groups of the multiple sound sources, and select one of the plurality of separated signals based on the obtained neural signals for the person.

In some variations, non-transitory computer readable media are provided, that are programmed with instructions, executable on a processor, to obtain, by a device comprising the processor, a combined sound signal for signals combined from multiple sound sources in an area in which a person is located, and apply, by the device, speech-separation processing to the combined sound signal from the multiple sound sources to derive a plurality of separated signals that each contains signals corresponding to different groups of the multiple sound sources. The instructions further include one or more instruction, executable on the processor, to further obtain, by the device, neural signals for the person, the neural signals being indicative of one or more of the multiple sound sources the person is attentive to, and select one of the plurality of separated signals based on the obtained neural signals for the person.

In some variations, an apparatus is provided that includes means for obtaining a combined sound signal for signals combined from multiple sound sources in an area in which a person is located, and means for applying speech-separation processing to the combined sound signal from the multiple sound sources to derive a plurality of separated signals that each contains signals corresponding to different groups of the multiple sound sources. The apparatus further includes means for obtaining neural signals for the person, the neural signals being indicative of one or more of the multiple sound sources the person is attentive to, and means for selecting one of the plurality of separated signals based on the obtained neural signals for the person.

Embodiments of the system, the computer-readable media, and the apparatus may include at least some of the features described in the present disclosure, including at least some of the features described above in relation to the method.

Details of one or more implementations are set forth in the accompanying drawings and in the description below. Further features, aspects, and advantages will become apparent from the description, the drawings, and the claims.

BRIEF DESCRIPTION OF THE DRAWINGS

These and other aspects will now be described in detail with reference to the following drawings.

FIG. 28 include tables providing data comparing the ODAN method with other speaker-independent speech separation methods on 2-speaker and 3-speaker mixtures.

Like reference symbols in the various drawings indicate like elements.

DETAILED DESCRIPTION

Figure 1:
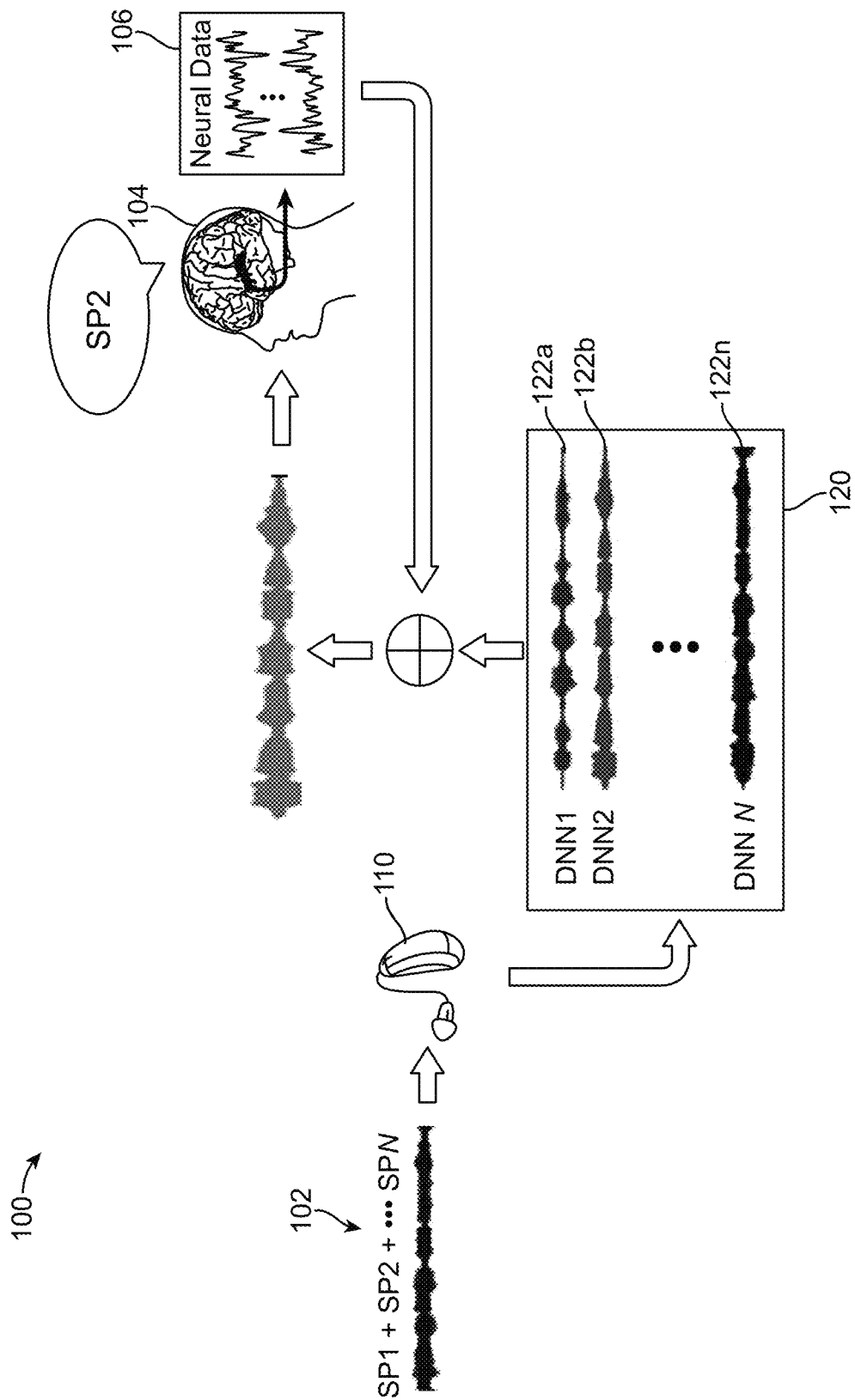
FIG. 1 is a diagram of a system to process (e.g., separate) combined sound signals (e.g., for attentional selection applications).

Described herein are systems, devices, apparatus, methods, computer program products, media, and other implementations, to process sound signals/data in environments that contain multiple sounds sources, based on neural signals/data from a person receiving the multi-source sound signals. In some embodiments, procedures to decode which speaker a person is attending to are implemented by monitoring their neural activity via both invasive and non-invasive electrophysiological recordings. In such embodiments, attention-aware brain-computer interfaces (BCIs) may be used to control smart hearable devices capable of selectively processing (e.g., amplifying) one speaker and/or suppressing other speakers in crowded environments.

In some attention decoding procedures, explicit access to the isolated sound sources in the environment may be required, which may be difficult to achieve. Techniques such as beamforming may be used in an attempt to isolate different speakers. However, these techniques may not be entirely adequate when there is little (or no) spatial separation between speakers. Also, the techniques' reliance on multiple microphones has drawbacks with regards to hardware complexity and user comfort. Thus, in implementations described herein, these challenges are addressed by using a single microphone, or by combining the beamforming techniques/methods with the proposed implementations, to implement automatic speech separation processing in which, for example, neural-network-based processing, such as deep neural network (DNN) models, are used to separate the sound sources. Generally, DNN refers to neural networks that include multiple hidden layers between the input and output layers of the networks. In DNN's that are used herein for speech separation processing, the output of the speech separation processes can be used to decode the attentional state of the listener, and subsequently, to amplify the attended source. For example, in some embodiments, a speech separation procedure separates out the speakers in a crowd, and compares to a signal reconstructed from the brain. The speech separation procedure can next amplify (or otherwise filter) that speaker source compared to other sources.

Accordingly, implementations described herein include a method that comprises obtaining, by a device (e.g., a hearing device, a hearing enhancement device to allow better hearing in a very noisy environment, a noise cancellation device, a virtual reality device, and/or other types of hearing augmentation devices), a combined sound signal for sound combined from multiple sound sources in an area in which a person is located. The method further includes applying, by the device, speech-separation processing to the combined sound signal from the multiple sound sources to derive a plurality of separated signals that each contains signals corresponding to different groups of the multiple sound sources, and obtaining, by the device, neural signals for the person, with the neural signals being indicative of one or more of the multiple sound sources the person is attentive to. The method additionally includes selecting one of the plurality of separated signals based on the obtained neural signals for the person. In some embodiments, obtaining the neural signals for the person may include obtaining one or more of, for example, electrocorticography (ECoG) signals for the person, neural measurements via a non-invasive scalp, and/or in-ear EEG recordings. Applying the speech-separation processing to the combined sound signal from the multiple sound sources may include providing the combined sound signal from the multiple sound sources to a deep neural network (DNN) configured to identify individual sound sources from the multiple sound sources based on the combined sound signal. The method may also include processing the selected one of the plurality of separated sound signals, including performing one or more of, for example, amplifying the selected one of the plurality of separated signals, and/or attenuating at least one non-selected signal from the separated sound signals.

In some embodiments, separation processes to separate the multi-source audio/sound signals may be realized as a deep learning framework for single channel speech separation by creating attractor points in high dimensional embedding space of the acoustic signals, which pull together the time-frequency bins corresponding to each source. Attractor points are created, in some embodiments, by finding the centroids of the sources in the embedding space, which are subsequently used to determine the similarity of each bin in the mixture to each source. The network is then trained to minimize the reconstruction error of each source by optimizing the embeddings.

Thus, in embodiments of the deep attractor network approach, the combined signal may be a mixture speech signal defining a time-frequency embedding space. Applying the speech-separation processing to the combined sound signal may include, in such embodiments, determining respective reference points for each of the multiple sound sources, with the reference points representing locations of the sources in the embedding space for the mixture speech signal, deriving masks for the determined reference points, and extracting at least one of the multiple sources using at least one of the derived masks. The reference points may include attractor points in the embedding space. Determining the respective reference points may include determining the respective reference points using a deep neural network. Deriving the masks may include computing similarity between embedded time-frequency points within the embedding space and the determined respective reference points. Other frameworks/approaches for speech separation that may be used in some of the various implementations described herein (be it for attentional selection application, surveillance applications, virtual or augmented reality applications, and otherwise) are also described below.

Attentional Selection in Multi-Speaker Environments

With reference now to FIG. 1, a diagram for an example system 100 to process sound signals is shown. The system 100 (which may be implemented as a hearing device to facilitate hearing for a person 104, or may be implemented as a noise cancellation device, or any other type of a hearing augmentation device) includes a microphone 110 to receive a combined sound signal 102 combining sound signals from multiple sound sources. In some embodiments, a controller (e.g., a computing-based device, which may be incorporated into the hearing device, or some other hearing augmentation device, used by the person 104) implements one or more sound-processing procedures 120 (which may each correspond to a separate DNN, although, in some embodiments, a single neural network unit may be configured to implement multiple separate DNN's) to process the combined (aggregated) sound signal 102 to separate the combined sound signal into a plurality of separate signals 122a-n (which may include sound signals, or may include signal representative and/or derived from sound signals). For example, in some embodiments, the one or more procedures 120 implemented by the system's controller may include a speech-separation process based on a deep-neural network. As will be discussed below in greater detail, the speech separation processes/procedures described herein may be based on neural network (or other types of learning engines), or may be implemented without using learning engines, e.g., speech separation may be implemented using filtering.

The system 100 also includes one or more sensors to obtain/measure neural signals/data 106 from the person 104 that are indicative of the sound source (e.g., one of multiple speakers in the vicinity of the person 104) the person 104 is attentive to. Based on the neural signals/data obtained for the person 104, one or more of the plurality of separated signals derived by the one or more procedures 120 is selected. In the example of FIG. 1, the neural signals obtained for the person 104 may indicate that the user is attentive to the sound source SP2, and, therefore, separated sound signal 122b (corresponding to the source SP2 in FIG. 1) is selected for further processing. The selected separated sound signal can then be processed to, for example, amplify, or otherwise perform signal enhancing filtering on the signal. Additionally and/or alternatively, the non-selected signals (i.e., the signals other than the sound signal 122b) may be processed to attenuate or suppress them (or to perform some other filtering operation thereon).

Figure 2:
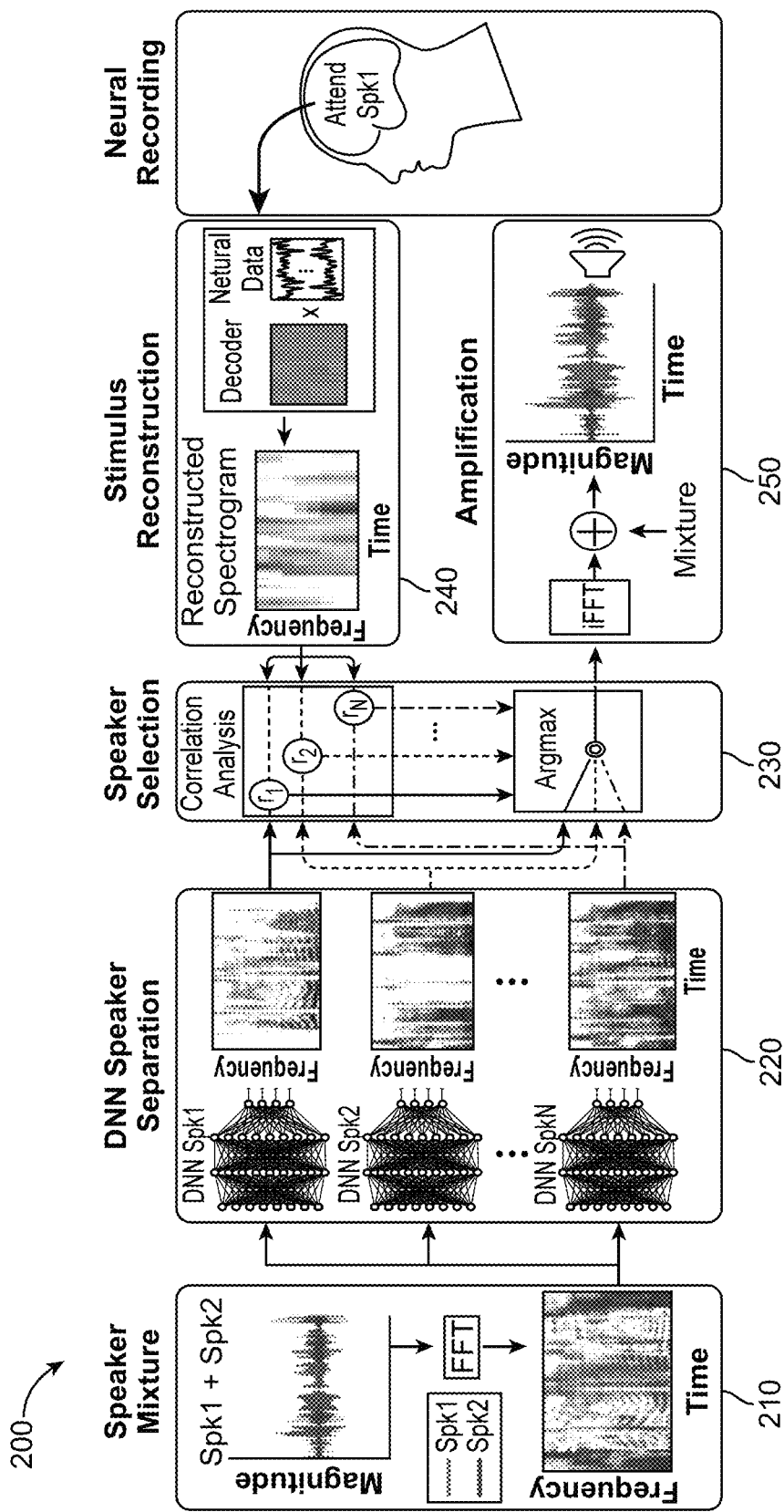
FIG. 2 is another example implementation of a system to process (e.g., separate) sound signals.

FIG. 2 depicts another example implementation of a system 200 to process (e.g., separate) sound signals (e.g., in a closed-loop). As shown, two speakers, namely, Spk1 and Spk2, are mixed together, as illustrated in a first stage 210 of the system 200. In some embodiments, the first stage 210 includes various signal recording and pre-processing operations performed on acquired audio signals. In example implementations that were realized and evaluated, as will be more particularly described below, some source speakers were recorded using Tucker Davis Technologies (TDT®) hardware and sampled at 2441 Hz, while other source speakers were recorded using Xltek® hardware and sampled at 500 Hz. Further processing operations were performed offline. In the implementations that were realized and tested herein, filters were realized using Matlab's® Filter Design Toolbox, and were used in both a forwards and backwards direction to remove phase distortion. In the example using TDT acquired data, the data was resampled to 500 Hz, and a $1^{st}$ order Butterworth highpass filter with a cut-off frequency at 1 Hz was used to remove DC drift. The data was subsequently re-referenced using a common average scheme, with the effect of noisy electrodes mitigated by using a trimmed mean approach (e.g., removing the top and bottom 10% of electrodes at each sample point). These example implementations also included removing line noise at 60 Hz and its harmonics (up to 240 Hz) using $2^{nd}$ order IIR notch filters with a bandwidth of 1 Hz. A period of silence was recorded before each experiment, and the corresponding data was normalized by subtracting the mean and dividing by the standard deviation of the pre-stimulus period. These implementations also included filtering data into two frequency bands known to be responsive to speech, namely, the high-frequency (HF) gamma band (70-150 Hz), and the low-frequency (LF) delta and theta bands (1-8 Hz). The power of the high-frequency band and the phase of the low-frequency band are modulated by speech. In order to obtain the power of the HF band, the data was first filtered into 8 frequency bands between 70 and 150 Hz, using, for example, Chebyshev Type 2 filters, each with a bandwidth of 10 Hz. The power analytic amplitude of each band could then be derived using a Hilbert transform. The average of all 8 frequency bands can then be used to represent the total HF power. To obtain the LF data, an $8^{th}$ order (4 sections) Butterworth low-pass filter was applied to the data with a corner frequency of, for example, 8 Hz, and 20 dB attention at 12 Hz.

With continued reference to FIG. 2, signal separation processing is applied to the combined (mixed) audio signal (which may have been processed based on, for example, processing operation such as those described in relation to stage 210) at stage 220. In some embodiments, speech separation processing is based on a deep neural network (DNN) approach. After obtaining the mixed/combined audio signal, a spectrogram of the mixture is obtained. This spectrogram is then fed to each of several DNNs, each trained to separate a specific speaker from a mixture (DNN Spk1 to DNN SpkN). At the same time, a user may be attending to one of the speakers (in this case, Spk1). A spectrogram of this speaker is reconstructed from the neural recordings of the user. This reconstruction is then compared with the outputs of each of the DNNs using a normalized correlation analysis (as shown at stage 230) in order to select the appropriate spectrogram, which is then converted into an acoustic waveform and added to the mixture so as to amplify the attended speaker (and/or attenuate the signals corresponding to the non-attended speakers).

More particularly, In order to automatically separate each speaker from the mixture, a single-channel speech separation that utilizes, in some embodiments, a class of DNNs known as long short-term memory (LSTM) DNNs is employed. Each DNN is trained to separate one specific speaker from arbitrary mixtures. In an experiment, two speakers (Spk1F and Spk2M) were presented to each subject. However, a system configured to work in a real-world situation would generally contain multiple DNNs, each trained to separate specific speakers, any of whom may or may not be present in the environment. In the example system of FIG. 2, 4 DNNs were trained to separate 4 speakers (two female speakers and two male speakers), hereafter referred to as Spk1F, Spk2M, Spk3F, and Spk4M. In an example, all speakers were native American English speakers. In order to be used by the DNNs, the speech waveforms were converted, in the example experiment, into 100-dimensional Mel-frequency spectrograms. The goal was then to obtain an estimate S' of a clean target spectrogram S from a mixture M. To do so, a soft mask Y' is learned and applied to the mixture to mask the interfering speech. The squared Euclidian distance between the masked spectrogram and the clean target spectrogram is treated as the error in order to generate the gradient that is back propagated through the DNN to update the parameters. An objective function that may be used is:

$$E(\hat{Y}) = \|\hat{Y}M - S\|_2^2$$

In the experimentation conducted for the implementations if the system 200, the input to the DNNs was the logarithm (base 10) of the spectrograms, normalized so that each frequency band had zero mean and unit variance. Each DNN, in the implementations realized and tested, contained four (4) layers with 300 nodes each, followed by a single layer containing 100 nodes with logistic activation to output a spectrogram. An acoustic waveform was generated by combining the spectrogram that was output by the DNN with the phase of the original mixture (e.g., inverting, in some embodiments, the spectrogram with the phase of the original mixture). In the implementations that were realized and tested, twenty (20) minutes of speech from the target speakers, and approximately five (5) hours of speech from interfering speakers were used. A target speaker sample was generally mixed with one interfering speaker, and both were mixed into the same channel and with the same root mean squared (RMS) intensity. Unseen utterances were used for testing (for both the target and interfering speakers). To ensure generalization, each of the DNNs did not receive training sample data for the other target speakers during training. That is, in the implementations realized and evaluated herein, a DNN trained to separate one speaker (e.g., Spk1F) was not exposed to training data for other speakers.

As will be discussed in greater detail below, in some embodiments, other types of speech separation processing may be applied to the mixed/combined signal. As noted, one speech separation approach that may be implemented is a deep attractor network (DANet) approach for separating multiple sound sources (e.g. speakers) from a single channel recording. Under this approach, the a deep learning framework for single channel speech separation is used that is configured to create attractor points in high dimensional embedding space of the acoustic signals, which pull together the time-frequency bins corresponding to each source. Attractor points may be created by finding the centroids of the sources in the embedding space, which are subsequently used to determine the similarity of each bin in the mixture to each source. The network is then trained to minimize the reconstruction error of each source by optimizing the embeddings. Advantages of the DANet approach is that it implements an end-to-end training, and it does not depend on the number of sources in the mixture. Two strategies that can be used with respect to the DANet implementations are the K-means strategy and the fixed-attractor-points strategy, where the latter requires no post-processing and can be implemented in real-time. In example system implementations of the DANet approach, the system was configured to output several waveforms, each corresponding to one sound source in the mixture, in response to an input mixed waveform. The processing operations of such a system implementation may include acquiring mixture speech signal with a (single) sensor, processing the signal to estimate a set of features, processing the features by a deep neural network (DNN) to assign a descriptor for each element in the signal, estimating the attribution of each element according to the physical properties of the descriptors, and recovering the target sources according to the estimation. Example embodiments based on the DANet approach can be incorporated into online applications or mobile devices to allow fast and accurate signal separation, and can also be deployed into hearing aids or earphones to be a front-end solution of source separation.

Other speech separations approaches that will be discussed in further detail below include an online deep attractor network (ODAN) approach, that is effective for handling situations involving new sources/speakers (i.e., where the implementations have not been trained to handle the new source/speaker), a time-domain audio separation approach using a deep long-short term memory network (LSTM), an approach based on use of convolutional encoder for time-domain separation procedure, etc.

While the embodiments described herein may use multiple possible speech separation approaches, for ease of illustration and explanation, the approach using multiple DNN's trained for specific respective speakers (i.e., the approach illustrated in FIGS. 1 and 2) will be referenced. However, as noted, the identification of speakers a listener is attending to can be performed using other speech separation approaches.

Thus, with continued reference to FIG. 2 (and similarly to FIG. 1), selection of the speaker, whose speech data is to be provided to the target user, is performed through use of a speaker selection stage 230 and a stimulus reconstruction stage 240 of the system 200. The signals corresponding to the selected speaker are then processed (e.g., amplified)

using the filtering processes implemented at stage 250. Additionally and/or alternatively, signals corresponding to non-selected speakers mat be processed to, for example, attenuate those signals. In some embodiments, the stimulus-reconstruction procedure implemented by the stage 240 applies a spatiotemporal filter (decoder) to neural recordings to reconstruct an estimate of the spectrogram of the attended speaker. A 100-dimensional log Mel-frequency spectrograms may be downsampled by a factor of 10, resulting in ten (10) frequency bands used for neural recordings. Each decoder can be trained using the data from the single-speaker (S-S) experiment.

Electrodes may be chosen if they are significantly more responsive to speech than to silence. For the high gamma (HG) data, this means that the average power during speech is greater than during silence. For the low frequency (LF) data, electrodes may be chosen if the average power is either significantly greater or lower during speech than during silence. To perform statistical analyses, the data can be segmented into 500 ms chunks and divided into two categories: speech and silence. Significance may then be determined using an unpaired t-test (false discovery rate (FDR) corrected, $q<0.05$). This results in varying numbers of electrodes retained for each frequency band and each subject. The decoders may be trained using time-lags from $-400$ to 0 ms.

Determining to whom the subject user is attending (i.e., which speaker the target user is trying to listen to) may be implemented through a correlation analysis, e.g., using Pearson's r-value (e.g., the linear correlation measure between two variables). Typically, whichever spectrogram has the largest correlation with the reconstructed spectrogram is considered to be the attended speaker. However, in embodiments in which four (4) DNNs are used, each trained to separate a speaker that may or may not be present in the combined signal (mixture), the analysis becomes slightly more complex. Because the DNNs that do not see their designated speakers in the mixture are likely to output a signal very close to the mixture, it may be necessary to normalize the correlation values with respect to the mixture. This is because the correlation between the reconstructed spectrograms and the mixture can be very large.

In the continued discussion of correlation analysis processing, the following terminology and notations will be used. The $k^{th}$ DNN (i.e., the DNN decoder configured to identify the $k^{th}$ specific speaker) is referred to as $S_{DNNk}$, the spectrogram of the mixture signal is represented as $S_{MIX}$, and the reconstructed spectrogram (from the neural responses) as $S_{RECON}$. In order to emphasize large correlations, a Fisher transformation (inverse hyperbolic tangent) is applied to each r-value.

The normalization procedure involves five stages. First, the correlation between $S_{RECON}$ and each $S_{DNNk}$, which is denoted as $\rho_{1k}$ is derived according to:

$$\rho_{1k}=\text{arctanh}\{r(S_{RECON},S_{DNNk})\} \quad (1)$$

where $r(x, y)$ is Pearson's correlation between the variables x and y, and arctanh is the inverse hyperbolic tangent function.

Next, the correlation between $S_{RECON}$ and the difference between $S_{DNNk}$ and $S_{MIX}$, which is referred to as $\rho_{2k}$, is computed according to:

$$\rho_{2k}=\text{arctanh}\{(S_{RECON},S_{MIX}-S_{DNNk})\} \quad (2)$$

This value, $\rho_{2k}$, should be close to zero if a DNN is outputting the mixture, should be relatively small if it is outputting the attended speaker (because subtracting the attended spectrogram from the mixture will only leave behind portions of the unattended spectrogram), and should be relatively large if it outputs the unattended speaker (similarly, because only portions of the attended speaker will be left). Therefore, taking the difference of $\rho_{1k}$ and $\rho_{2k}$, and dividing by their sum, should produce a score $(\alpha_k)$ that can differentiate between each of these cases, where $\alpha_k$ is computed according to:

$$\alpha_k = \frac{\rho_{1k}-\rho_{2k}}{\rho_{1k}+\rho_{2k}} \quad (3)$$

The computation of $\alpha_k$ is followed by a test-normalization, in which the $\alpha$ score for each DNN is normalized relative to the distribution of $\alpha$ scores from all DNNs, according to:

$$\beta_k = \frac{\alpha_k - \mu_\alpha}{\sigma_\alpha} \quad (4)$$

where $\mu_\alpha$ and $\sigma_\alpha$ are the mean and standard deviation of the distribution of $\alpha$ scores from all DNNs.

The next neural correlation processing stage includes subtracting the correlation between $S_{DNNk}$ and $S_{MIX}$, and adding the constant 1, providing a resultant normalized correlation value, $P_k$, for each DNN, which is computed according to:

$$P_k=\beta_k-\text{arctanh}\{(S_{DNNk},S_{MIX})\}+1 \quad (5)$$

The above normalization operation effectively penalizes a DNN that is simply outputting the mixture rather than separating the speakers. This could occur if a DNN's trained speaker was not in the mixture. The addition of the constant 1 is used to make the final result more intuitive, as otherwise the values would typically be less than zero.

In experimentations and testing of the neural correlation processing realized as part of the implementations described herein, the lowest two frequency bands (~50-200 Hz) of the 10 frequency bands in the downsampled spectrograms were excluded to avoid bias towards male speakers whose fundamental frequency occupied the exclusion range region. Correlation values derived may thus correspond to the average of the r-values obtained across the remaining eight (8) non-excluded frequency bands.

In order to obtain a measure of the ability of the implemented systems described herein to determine the attended speaker from neural recordings, the reconstructed spectrogram is first segmented (from the multi-speaker experiments) into, for example, 20-second bins. In an example implementation, in which four (4) DNNs are trained to separate two female speakers (denoted as Spk1F and Spk3F) and two male speakers (Spk2M and Spk4M) from random mixtures, four normalized correlation values are produced by the DNN's for each segment (the normalized correlation values are denoted $P1_f$, $P2_m$, $P3_f$, and $P4_m$). When, for example, Spk1F and Spk2M are the only speakers that are presented to the subject (the listener), it is expected that $P1_f$ and $P2_m$ would be the largest, depending on whom the subject was attending to. If there are only two possible correlation values to choose from, a segment could be considered correctly decoded if the attended speaker produced the largest correlation with the reconstructed spectrogram. However, when there are multiple values to choose from, it is important to take into account any bias for a particular speaker. This is of particular importance when using intracranial data, because it is possible that some electrodes could be tuned to speaker-specific features, and respond to those features regardless of the attentional focus of the subject. To take into account any such potential bias, the Attention Decoding Index (ADI) metric is defined as the proportion of the number of correct hits minus the number of false positives, for target speakers. The ADI metric may be computed as:

$$ADI = (CH_{spk1} + CH_{spk2} - FP_{spk1} - FP_{spk2})/nS \qquad (6)$$

where $CHs_{SpkN}$ and $FP_{SpkN}$ are the number of correct hits and false positives for speaker N, respectively, and nS is the number of segments. The resultant metric is bounded between $[-1, 1]$. In some of the experimentations and evaluation performed for the systems implemented herein, chance and significant ADI were determined by randomly shuffling the reconstructed spectrograms with respect to the DNN outputs 100 times for each subject. This allowed finding the actual chance performance and comparing that to the performance of the system (to test the significance of the result). A null distribution of the ADI was then obtained using the same normalized correlation analysis described above. The resulting mean +/−SD performance was 0 +/−0.15 for both HF and LF data. Significant performance was therefore determined to be 0.45 (three times the standard deviation). For comparison, the ADI that would be achieved using the clean (ideal) spectrograms of Spk1F and Spk2M was also computed. In that ideal situation, it was assumed that the DNNs trained on Spk3F and Spk4M outputted the mixture.

In some of the experimentations and evaluations conducted, in order to simulate a dynamic scenario in which a subject (a listener) was switching attention, the neural data was artificially divided and concatenated into consecutive segments in which subjects were attending to either speaker. Specifically, the data was divided into ten (10) segments, each lasting 60 seconds. The subjects attended to the male speaker for the first segment. To assess the ability to track the attentional focus of each subject, a sliding window approach was used in which correlation values were obtained every second over a specified window. Window sizes ranging from 5 to 30 seconds (in 5 second increments for 6 window sizes in total) were used. Larger windows should lead to more consistent (i.e., less noisy) correlation values and provide a better estimate of the attended speaker. However, they should also be slower at detecting a switch in attention.

Thus, implementations described herein include a system comprising at least one microphone to obtain a combined sound signal for sound combined from multiple sound sources in an area in which a person is located, one or more neural sensors to obtain neural signals for the person, with the neural signals being indicative of one or more of the multiple sound sources the person is attentive to, and a controller coupled to the at least one microphone and the one or more neural sensors. The controller is configured to apply speech-separation processing (e.g., neural-net processing such as deep neural network, or DNN) to the combined sound signal from the multiple sound sources to derive a plurality of separated signals that each contains signals corresponding to different groups of the multiple sound sources, select one of the plurality of separated signals based on the obtained neural signals for the person, and process the selected one of the plurality of separated signals.

Figure 3:
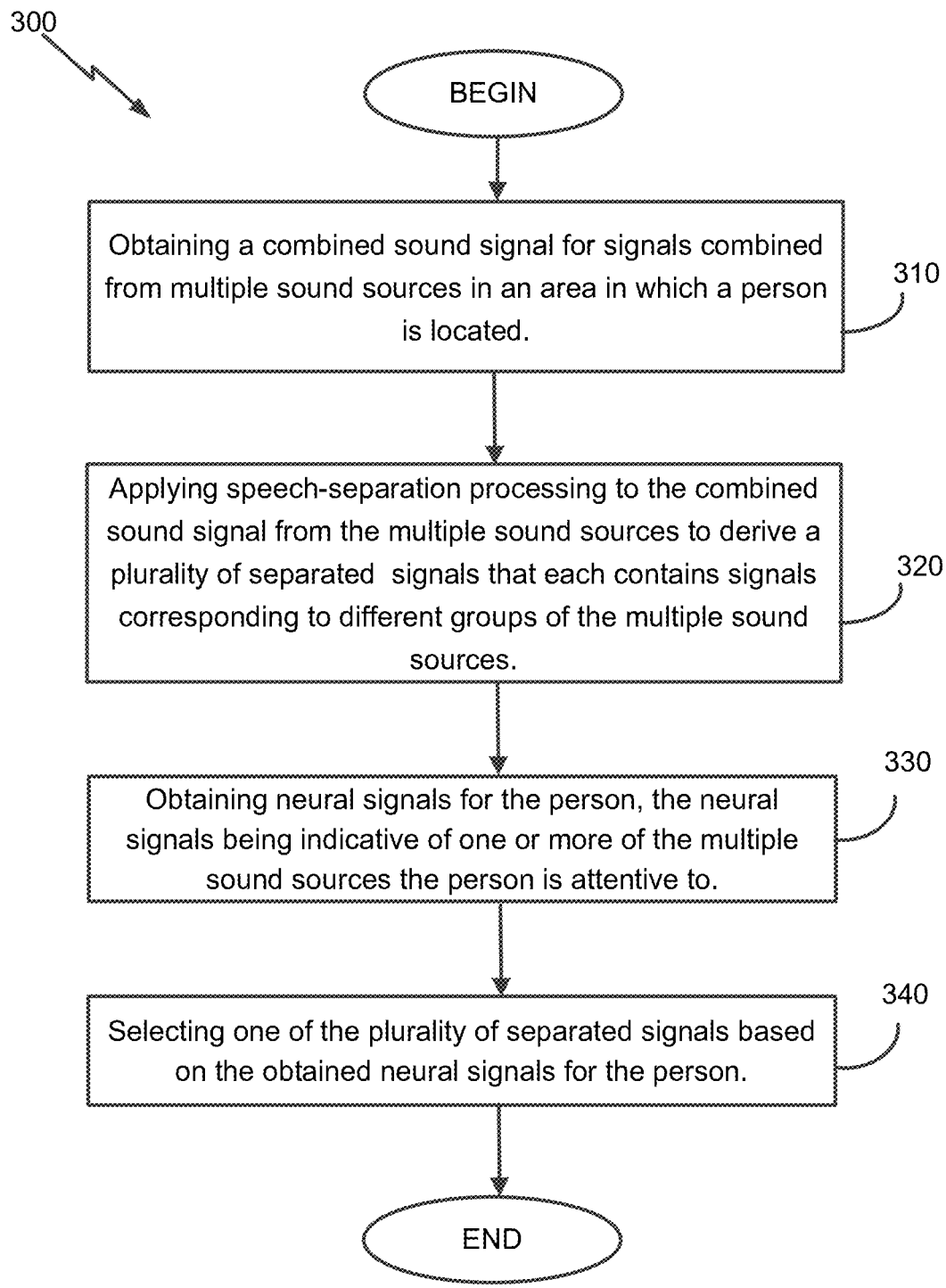
FIG. 3 is a flowchart of an example procedure for attentional selection of a speaker in a multi-speaker environment.

With reference now to FIG. 3, a flowchart of an example procedure 300 for attentional selection of a speaker in a multi-speaker environment. The procedure 300 includes obtaining 310, by a device, a combined or mixed sound signal for signals combined from multiple sound sources in an area in which a person is located. As noted, the device of procedure 300 (that performs that various operation of the procedure 300) may include one or more of, for example, a hearing device, a hearing enhancement device (to allow better hearing in a very noisy environment), a noise cancellation device, a virtual reality device, and/or other types of hearing augmentation devices. In some embodiments, the combined signal may be obtained through use of a single receiving sensor (e.g., a single microphone), although the procedure 300 may be performed using multiple receiving sensor which may be part of the device implementing the procedure 300.

As further shown in FIG. 3, the procedure 300 includes applying 320, by the device, speech-separation processing to the combined sound signal from the multiple sound sources to derive a plurality of separated signals that each contains signals corresponding to different groups of the multiple sound sources. Applying the neural-network-based speech-separation processing to the combined sound signal from the multiple sound sources may include providing the combined sound signal from the multiple sound sources to a deep neural network (DNN) configured to identify individual sound sources from the multiple sound sources based on the combined sound signal. In some embodiments, the DNN may include a plurality of individual DNN's (e.g., long short-term memory (LSTM) DNN's) that are each configured to separate one respective specific speaker from an arbitrary mixture of signals. Configuring the individual DNN's to separate their respective specific speakers may be realized through an initial training of the DNN's using speech data from the specific speaker, and speech data from interfering speakers (e.g., a combined/mixed speech signals). In some embodiments, speech separation processing may be applied to resultant data derived from the raw combined speech data (signals). For example, the speech separation processing may be applied to sound spectrogram data to derive multiple resultant speaker spectrograms. In such embodiments, the procedure 300 may further include generating a sound spectrogram from the combined sound signal, and applying the speech-separation processing to the generated spectrogram to derive multiple resultant speaker spectrograms.

As noted, in some embodiments, other speech separation approaches, such as the deep attractor network (DANet) approach, more particularly discussed below, may be used for the speech separating processing performed on the combined speech data, or performed on some resultant data derived from the combined speech data. Thus, in implementations to realize the deep attractor network approach, the combined sound signal may define a time-frequency embedding space, and applying the speech-separation processing to the combined sound signal may include determining respective reference points for each of the multiple sound sources, with the reference points representing locations of the sources in the embedding space for the combined sound signal, deriving masks for the determined reference points, and extracting at least one of the multiple sound sources using at least one of the derived masks. In such embodiments, determining the respective reference points may include determining the respective reference points using a deep neural network. Deriving such masks may include computing similarity between embedded time-frequency points within the embedding space and the determined respective reference points. The reference points may include attractor points in the embedding space.

In some embodiments, the speech separation process may be the LSTM-TasNet approach discussed in greater detail below. In such embodiments, applying the speech-separation processing to the combined sound signal may include dividing the combined sound signal into non-overlapping segments, transforming the non-overlapping segments into respective weighted sums of a learnable overcomplete basis of signals (with weight coefficients for the respective weighted sums being non-negative) performing neural-network-based processing on the respective weighted sums of the learnable overcomplete basis of signals to derive a plurality of mask matrices corresponding to different groups of the multiple sound sources, and estimating a plurality of reconstructed sounds signals from the derived plurality of mask matrices corresponding to the different groups of the multiple sound sources. In such embodiments, transforming the non-overlapping segments into the respective weighted sums may include estimating the respective weighted sums of the learnable overcomplete basis of signals using a gated 1-D convolution layer according to $w_k=\text{ReLU}(x_k*U)\odot\sigma(x_k*V)$, $k=1, 2, \ldots, K$, where $U\in R^{N\times L}$ and $V\in R^{N\times L}$ are N vectors with length L, $w_k\in R^{1\times N}$ is a mixture weight vector for segment k, $\sigma$ denotes a Sigmoid activation function, and * denotes a convolution operator.

In some embodiments, performing neural-network-based processing on the respective weighted sums to derive the plurality of mask matrices may include inputting the respective weighted sums of the learnable overcomplete basis of signals to a deep long-short term network (LSTM) followed by a fully connected layer with Softmax activation function for mask generation. Estimating the plurality of reconstructed sounds signals may include computing a source weight matrix, $D_i$, according to $D_i=W\odot M_i$, where $D_i=[d_{i,1}, \ldots, d_{i,K}]\in R^{K\times N}$ is the weight matrix for source I, and synthesizing a time-domain synthesis of the sources by multiplying the weight matrix $D_i$ with basis signals $B\in R^{N\times L}$.

In some examples, the speech separation process may be the online deep attractor network (ODAN) approach described more fully below. In such examples, applying the speech-separation processing to the combined sound signal from the multiple sound sources to derive the plurality of separated signals may include representing the combined sound signal as a time-frequency mixture signal in a time-frequency space, projecting the time-frequency mixture signal into an embedding space comprising multiple embedded time-frequency bins, tracking respective reference points for each of the multiple sound sources (with the reference points representing locations of the multiple sound sources in the embedding space) based at least in part on previous locations of the respective reference points at one or more earlier time instances, deriving masks for the tracked respective reference points, and extracting at least one of the multiple sound sources using at least one of the derived masks. In such embodiments, projecting the time-frequency mixture signal into the embedding space may include processing the time-frequency mixture signal with a neural network comprising a plurality of stacked long short-term memory (LSTM) layers, coupled to a fully connected network. The reference points may include attractor points in the embedding space. Tracking the respective reference points may include computing distances of current embedded time-frequency bins to previous locations of the respective reference points at an earlier time instance, and assigning the each of the current embedded time-frequency bins to respective ones of the multiple sources based on the computed distances. These examples may also include updating current locations of the reference points based, at least in part, on assignments of the each of the current embedded time-frequency bins to the respective ones of the multiple sources. Deriving masks for the tracked reference points may include generating the masks based, at least in part, on the updated current locations of the references points.

In some examples, the speech separation process may be a convolutional encoder TasNet (Conv-TasNet) framework described more fully below. In such examples, applying the speech-separation processing to the combined sound signal from the multiple sound sources to derive the plurality of separated signals may include dividing the combined sound signal into a plurality of segments, transforming the plurality of segments into a plurality of corresponding encoded segments represented in an intermediate feature space, estimating, for each of the plurality of corresponding encoded segments, multiple mask functions for respective ones of the multiple sound sources by passing the each of the plurality of corresponding encoded segments through a stacked dilated convolutional network, multiplying the estimated mask functions with the respective one of the plurality of corresponding encoded segments to produce respective resultant multiple masked segments, and generating separated estimates of the signals from the multiple sound sources based on the respective resultant multiple masked segments. In some embodiments, estimating the multiple mask function may include performing, at each block of the stacked dilated convolution network, a 1×1 convolution operation followed by a depthwise separable convolution operation (S-conv). The method may further include performing another 1×1 convolution operation, at the each block of the stacked dilated convolutional network, following the S-conv operation, with a non-linear activation function (PReLU) and a normalization process added between each two convolution operations in the each block of the stacked dilated convolutional network.

With continued reference to FIG. 3, the procedure 300 also includes obtaining 330, by the device, neural signals for the person, with the neural signals being indicative of one or more of the multiple sound sources the person is attentive to. Obtaining the neural signals for the person may include obtaining one or more of, for example, electrocorticography (ECoG) signals for the person, neural measurements via a non-invasive scalp, and/or in-ear EEG recordings.

Using the neural signals obtained for the person (the listener), the procedure 300 includes selecting 340 one of the plurality of separated signals based on the obtained neural signals for the person. As noted, in some embodiments, selecting the one of the plurality of separated signals may include generating an attended speaker spectrogram based on the neural signals for the person, comparing the attended-speaker spectrogram to the derived multiple resultant speaker spectrograms to select one of the multiple resultant speaker spectrograms, and transforming the selected one of the multiple resultant speaker spectrograms into an acoustic signal. In such embodiments, comparing the attended-speaker spectrogram to the derived multiple resultant speaker spectrograms may include comparing the attended-speaker spectrogram to the derived multiple resultant speaker spectrograms using normalized correlation analysis.

In some embodiments, the procedure 300 may optionally include processing the selected one of the plurality of separated signals. For example, in some embodiments, processing the selected one of the plurality of separated sound signals may include one or more of amplifying the selected one of the plurality of separated signals, and/or attenuating at least one non-selected signal from the separated signals.

While the speech-separation processes described herein are discussed primarily in relation to attentional selection application (e.g., to enhance the speech of a speaker, from a plurality of speaker, that the listener is focusing on), the speech-separation processes described herein may be utilized for other applications. For example, the speech separation processes may be used in surveillance application (to separate and record speech from a combined sound signal corresponding to different speakers). In other words, the speech separation processes described herein may be used to automatically analyze and transcribe surveillance audio, which can be hundreds of hours long. The speech separation processes can be used as a preprocessing step, where the target speech sounds are first separated from other sources that might have been present during the recording, and the cleaned speech signal can be passed to speech recognition implementation. In another example, the speech separation processes described herein may be used for virtual reality applications, in which speech separation techniques discussed are used to reconstruct speaking objects from a pre-recorded source (and render the separated speech signals into a virtual audio (or audio-visual) scene). One of the challenges in 3D virtual audio is that rendering an acoustic scene requires separate audio tracks for individual sources, so that the sound sources can be processed separately and placed in different positions relative to the listener. When such separate audio tracks are not available, the speech processing procedures described herein can be used to first separate all the sources in the recording, and subsequently re-synthesize them with desired location and attribute.

Figure 4:
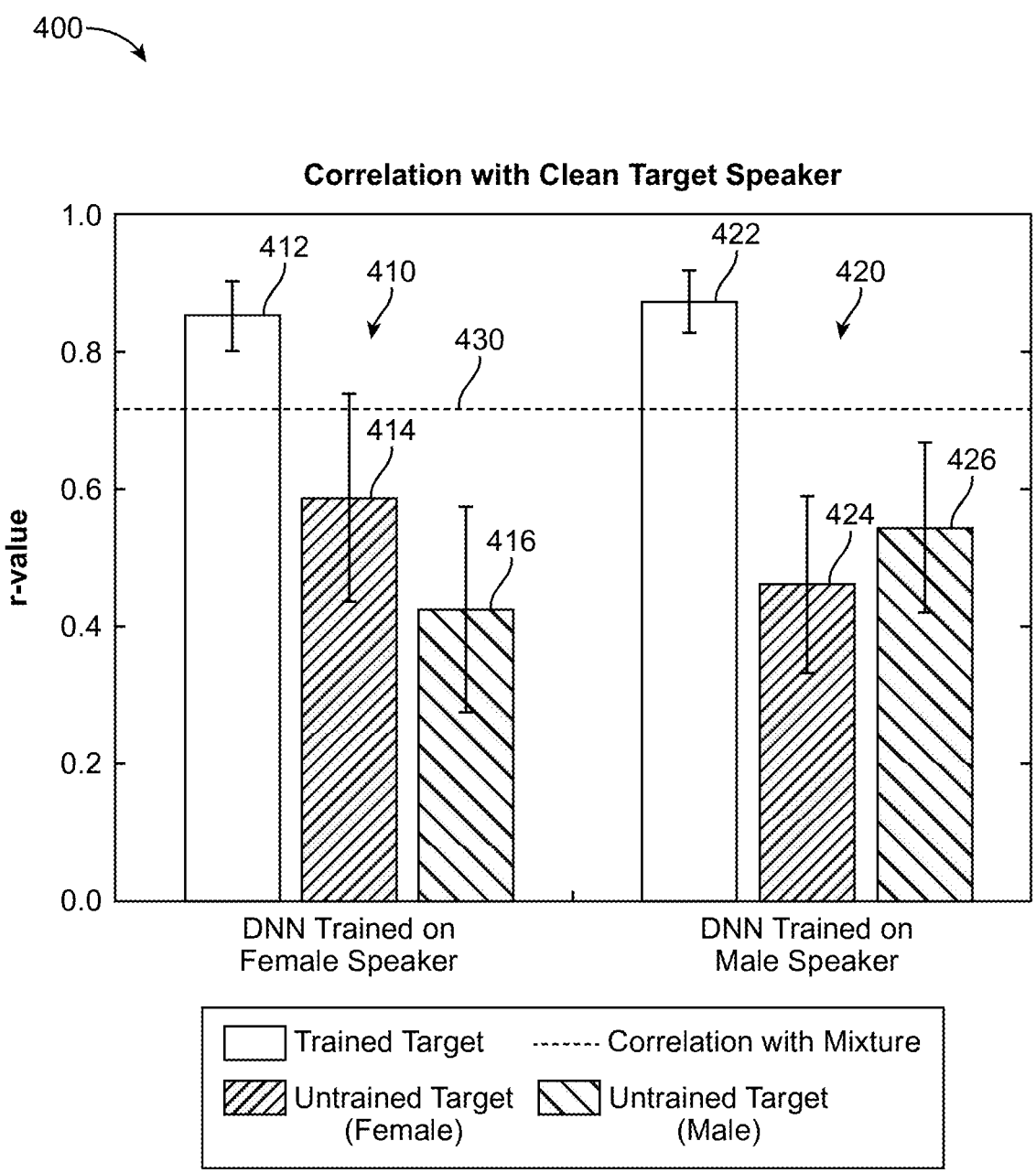
FIG. 4 is a graph providing an analysis of deep neural network (DNN) output correlation.

The implementations described herein were tested to evaluate their performance and efficacy. FIG. 4 includes a graph 400 providing an analysis of the DNN output correlation. To test the performance of the DNNs at single-channel speaker-separation, multiple mixtures of random speakers were created, with four (4) target speakers (2 male and 2 female), and with each mixture being passed through four DNNs that were each pre-trained to separate one of the target speakers. Performance was measured by obtaining the correlation (r-value) between the output of each DNN and the spectrogram of the clean target speaker. The results from the four networks are split into two by averaging the r-values obtained from the networks that were trained to separate a female speakers (left portion 410 of the graph 400) or male speakers (right portion 420 of the graph 400). The bars 412 and 422 show the results when a DNN was presented with a mixture containing its designated pre-trained speaker (trained target), while the bars 414, 416, 424, and 426 are the results when the mixtures contained an undesignated speaker (i.e., an untrained target, with the bars 414 and 424 corresponding to female speakers, and 416 and 426 corresponding to make speakers). The dotted line 430 shows the average correlation between the raw mixture and the clean target speaker. The results illustrated in FIG. 4 show that, as expected, the networks could not separate undesignated speakers from the mixture, but their outputs were slightly more similar to the target speaker when that speaker was the same gender as the network's designated speaker. This result is likely because of the characteristic differences between male and female speakers (e.g., pitch, spectral envelope).

Figure 5:
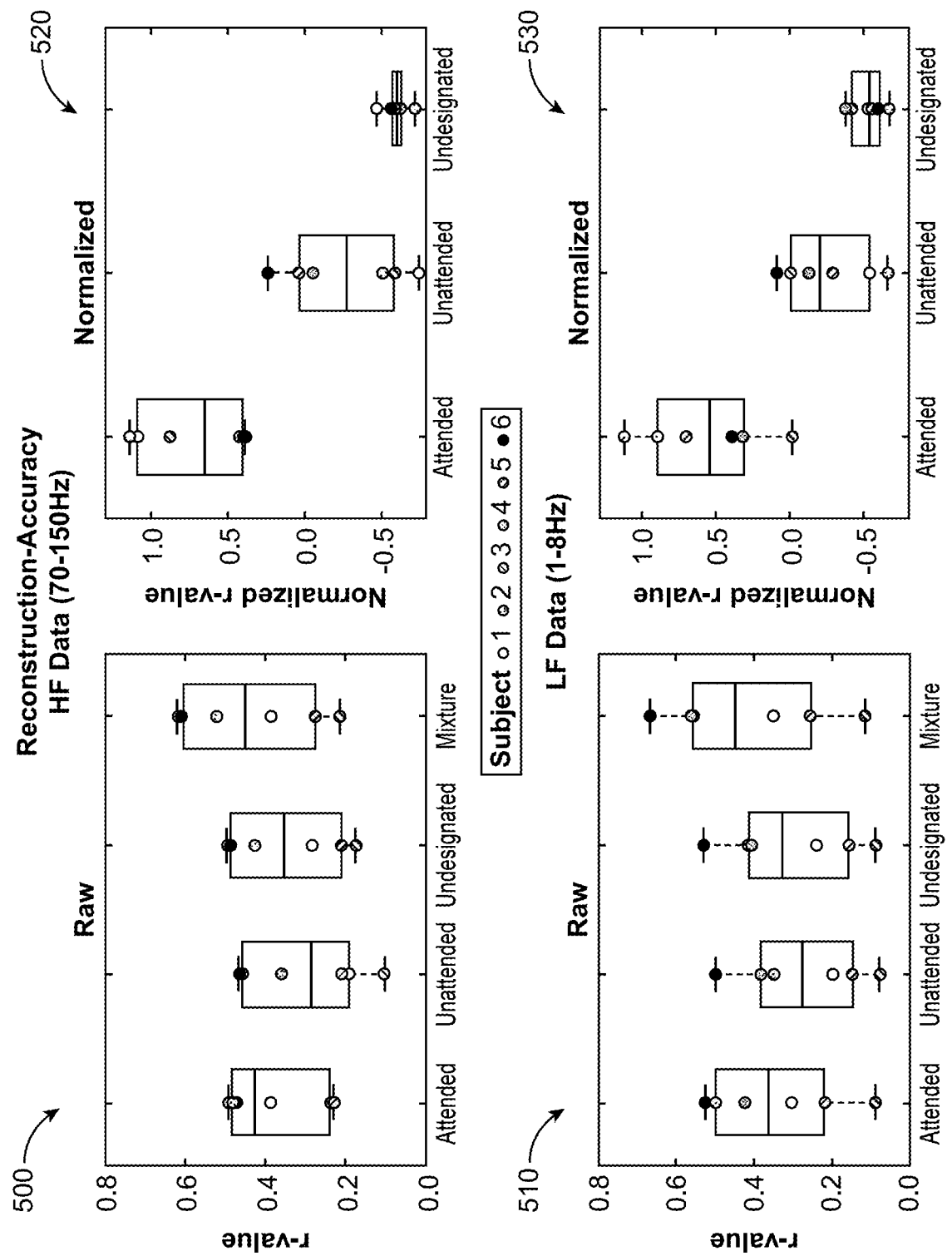
FIG. 5 includes graphs illustrating reconstruction accuracy for neural correlation analysis.

To determine which speaker a subject was attending to, a neural correlation analysis was performed to compare the reconstructed spectrograms (from the neural data) with the output of each DNN. FIG. 5 includes graphs 500, 510, 520, and 530, illustrating reconstruction accuracy for the neural correlation analysis. The left part of FIG. 5, including the graphs 500 and 510, provides the reconstruction accuracy in terms of raw r-values, and shows the average correlations between the reconstructed spectrograms and the outputs of the DNNs for each subject and neural frequency band (where each subject is represented by a dot of a different shade). Because, in the experiments conducted, the subjects alternated their attention between two speakers, the r-values labeled as attended and unattended come from the DNNs trained on Spk1F and Spk2M. The r-values labeled as undesignated come from the DNNs that were trained for Spk3F and Spk4M (as used herein, "undesignated" means that the DNN's in question were not trained to separate either speakers in the mixture that the listener actually listened to). Although the attended r-values are typically higher than the unattended r-values, there is also a high correlation between the reconstructed spectrograms and the mixture. Because the DNNs that do not see their designated speaker usually output spectrograms similar to the mixture, the undesignated correlation values were also relatively high.

In some embodiments, to improve the reconstruction analysis, the r-values are normalized with respect to the mixture. An example normalization solution involves three key steps: (i) incorporating the mixture into the correlation analysis (in accordance with, for example, Equations 2 and 3 above), (ii) performing a test-normalization (t-norm) to equalize the outputs of each DNN with respect to each other (in accordance with, for example, Equation 4, above), and (iii) subtracting the correlation between the DNN output and the mixture (in accordance with, for example, Equation 5). The graphs 520 and 530 at the right portion of FIG. 5 provide the correlation analysis results in terms of normalized r-values, and indicate that after applying the normalization processes, the attended correlation values were far higher than either the unattended or undesignated r-values, which allows adequate decoding of the attended speaker.

Figure 6A:
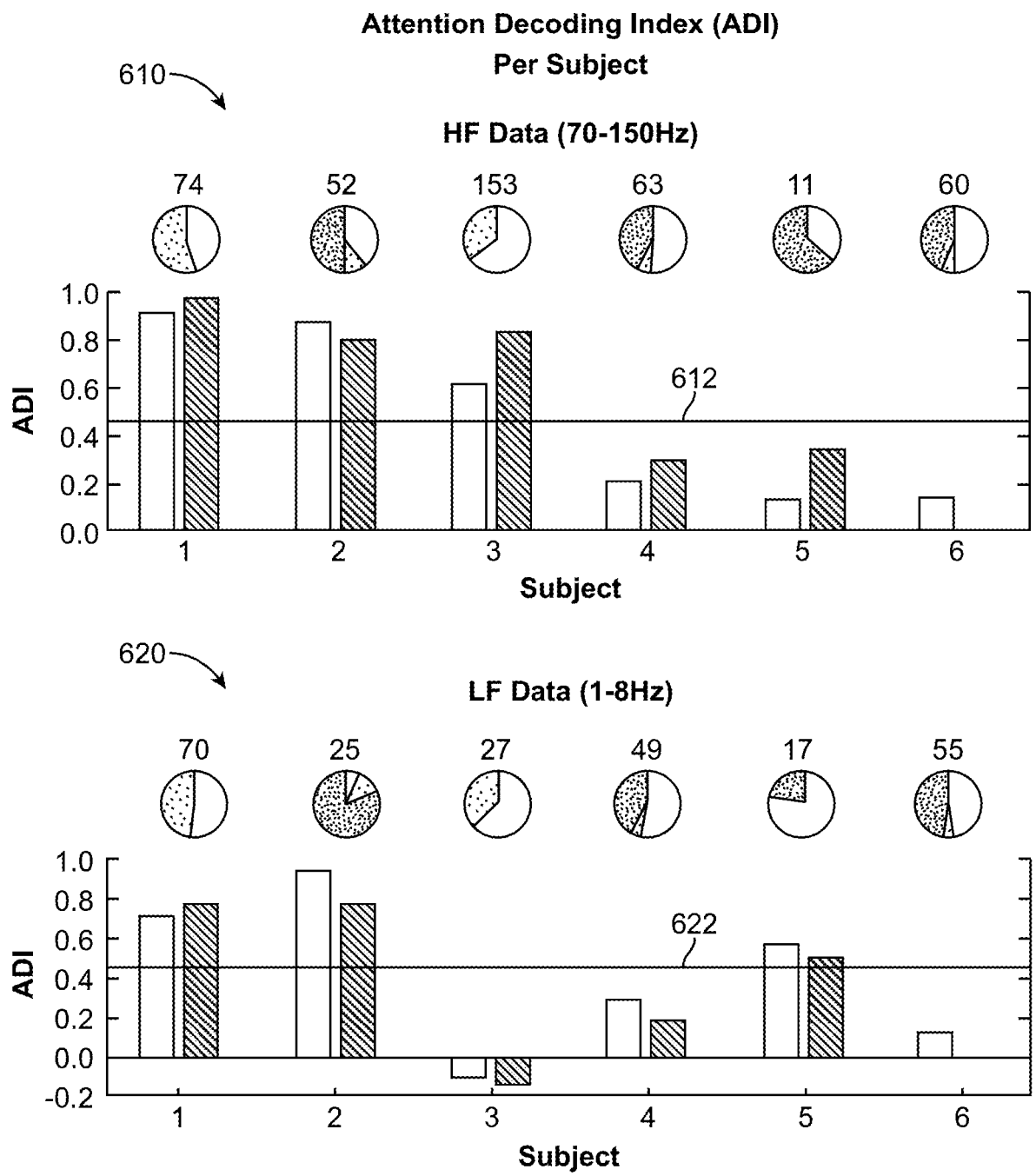
FIG. 6A includes graphs showing the proportion of segments in which the attentional focus of subjects could be correctly determined using HF data and LF data.

Given that the normalized correlation values differentiated between attended, unattended, and undesignated r-values, it is possible to decode the attentional focus of the subjects using the DNN outputs. After segmenting, in some implementations, the data into 20-second chunks, a segment was labeled as a correct hit (CH) if the normalized correlation between the reconstructed spectrogram and the output of the DNN that was trained to separate the attended speaker was the highest of all 4 DNN outputs. A segment was considered to be a false positive if the correlation with the unattended speaker was higher than all others. The Attention Decoding Index (ADI) is defined as the proportion of segments correctly decoded minus the proportion of false positives. For comparison, the ADI obtained is also calculated using the ideal (clean) spectrograms of Spk1F and Spk2M. FIG. 6A includes graphs 610 and 620 showing the proportion of segments (20 s) in which the attentional focus of each subject could be correctly determined using HF data (the graph 610 at the left part of FIG. 6A) and LF data (the graph 620 at right part of FIG. 6A). The attentional focus of a subject was considered to be successfully decoded if the ADI was greater than the 0.45 threshold (indicated by the lines 612 and 622) calculated using a random shuffle of the data. Of the 6 subjects who participated in an experimental study, the attentional focus of subjects 1, 2, and 3 could be decoded using HF (70-150 Hz) data, and subjects 1, 2 and 5 using LF (1-8 Hz) data. Because different regions in the auditory cortex are differentially modulated by attention, the variability in ADI across subjects was thought to be related to the anatomical locations of electrodes. For each subject, and for each frequency band, the pie charts in the graphs 610 and 620 illustrate the proportion of electrodes that were responsive to speech from two (2) anatomical regions: Heschl's gyms, and the superior temporal gyms. Electrodes that were responsive to speech, but that were not in either of these locations, are collectively referred to as Other. These Other electrodes were located in various anatomical regions including the middle and inferior temporal gyri, and planum temporale. The single number displayed above each pie chart refers to the total number of electrodes that were responsive to speech for that subject and for the corresponding frequency band.

Figure 6B:
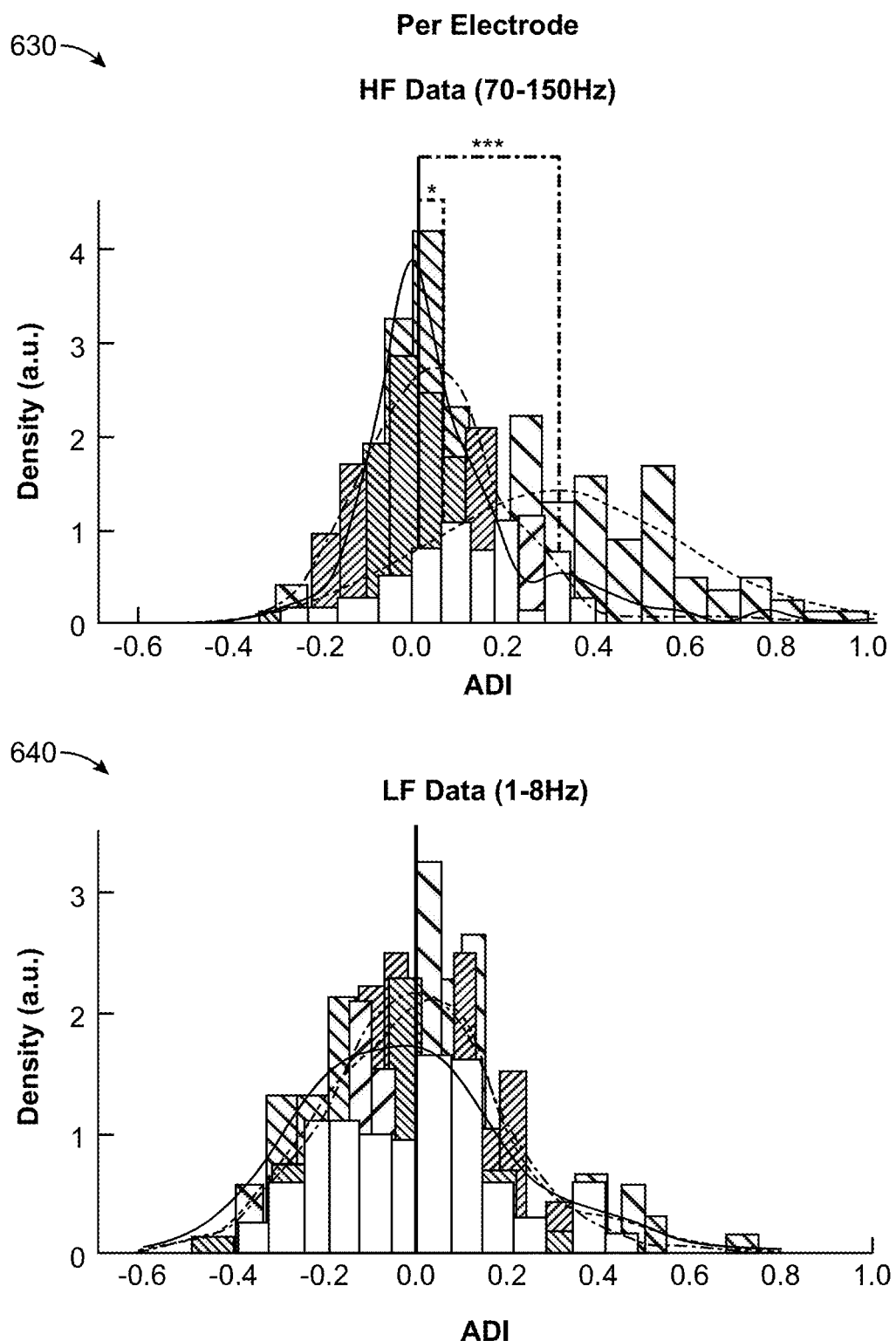
FIG. 6B includes graphs presenting attention decoding index (ADI) measures per electrode.

To determine which anatomical regions produced the highest ADI, a single electrode analysis was performed, as illustrated in FIG. 6B, which includes graphs 630 and 640 presenting ADI measures per electrode. Similar to FIG. 6A, electrodes are shaded according to anatomical location: Heschl's gyms (HG; medium dark shade), superior temporal gyms (STG; dark shade), and Other (light shade). When using HF data, electrodes in STG and Other produced ADIs significantly greater than zero (Wilcoxon signed-rank test; $p<0.001$), compared to the use of electrodes in HG ($p=0.02$). Using LF data, no region produced ADIs significantly greater than zero ($p>0.05$). These results show that electrodes placed in STG are important for successfully decoding attention (an important finding for non-invasive AAD research where source localization methods can be used to target specific brain regions).

Figure 7:
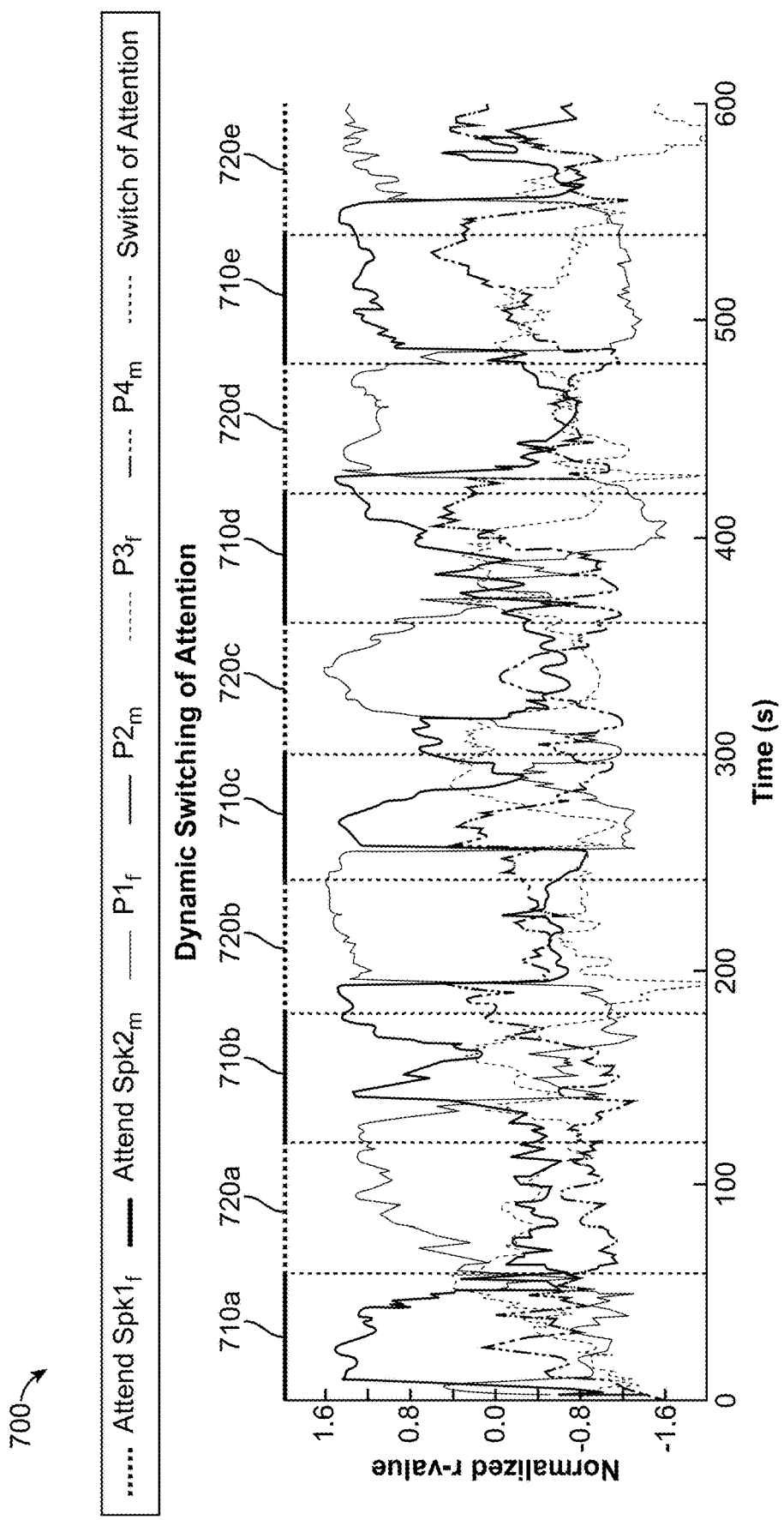
FIG. 7 is a graph showing results of an analysis for dynamic switching of attention for an example subject.

In a further experiment of the implementations described herein, to simulate a dynamic situation where subjects alternated their attention between the two speakers, the data was segmented and concatenated into 60-second chunks, with a subject's attention switching at the beginning of each chunk. FIG. 7 shows the results of the analysis for dynamic switching of attention for an example subject (subject 1) using HF data and a 20 second window size. Each solid vertical line marks a switch in attention. Portion 710*a-e* of the graph correspond to segments when the subject was attending to Spk2*m*, and portions 720*a-e* correspond to segments when the subject was attending to Spk1*f*. Normalized correlation values for each of the 4 DNNs are plotted at the bottom of the figure. From this analysis, a measure of decoding-accuracy was obtained, which was defined as the percentage of samples in which the correct target speaker produced the highest normalized correlation value. Unlike the ADI method discussed above, this method does not formally take into account false-positives. This is because the sliding window approach inevitably produces false-positives around transitions in attention that are not due to a bias towards a particular speaker, but are instead an inherent property of the methodology. However, these false-positives will still reduce the decoding-accuracy achievable because the correct target speaker will not produce the highest correlation values in these regions. A decoding-accuracy of 75% was observed for the data displayed in FIG. 7.

Figures 8A, 8B:
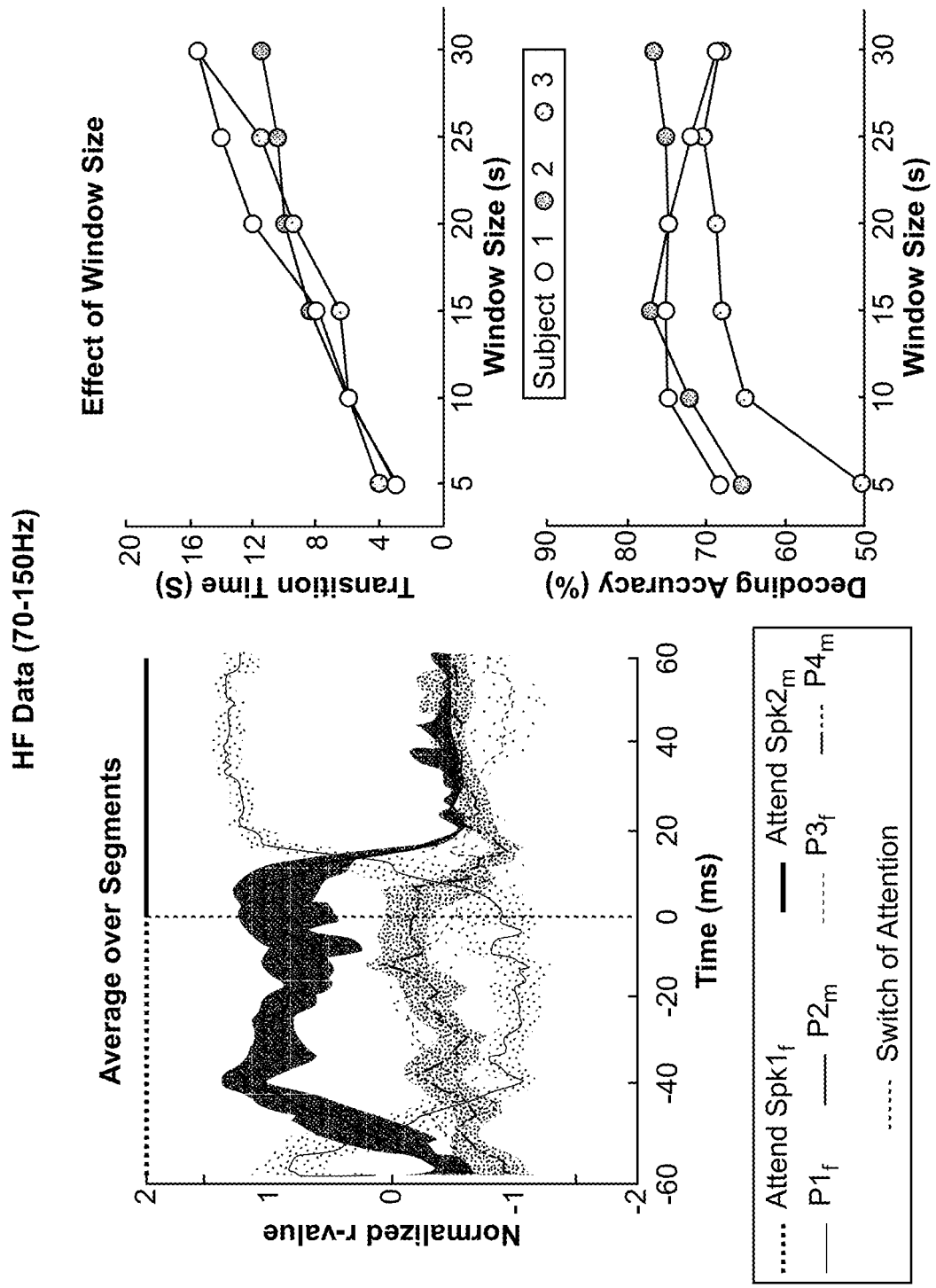
FIGS. 8A-D are graphs showing further performance results in relation to dynamic switching of attention
Figures 8C, 8D:
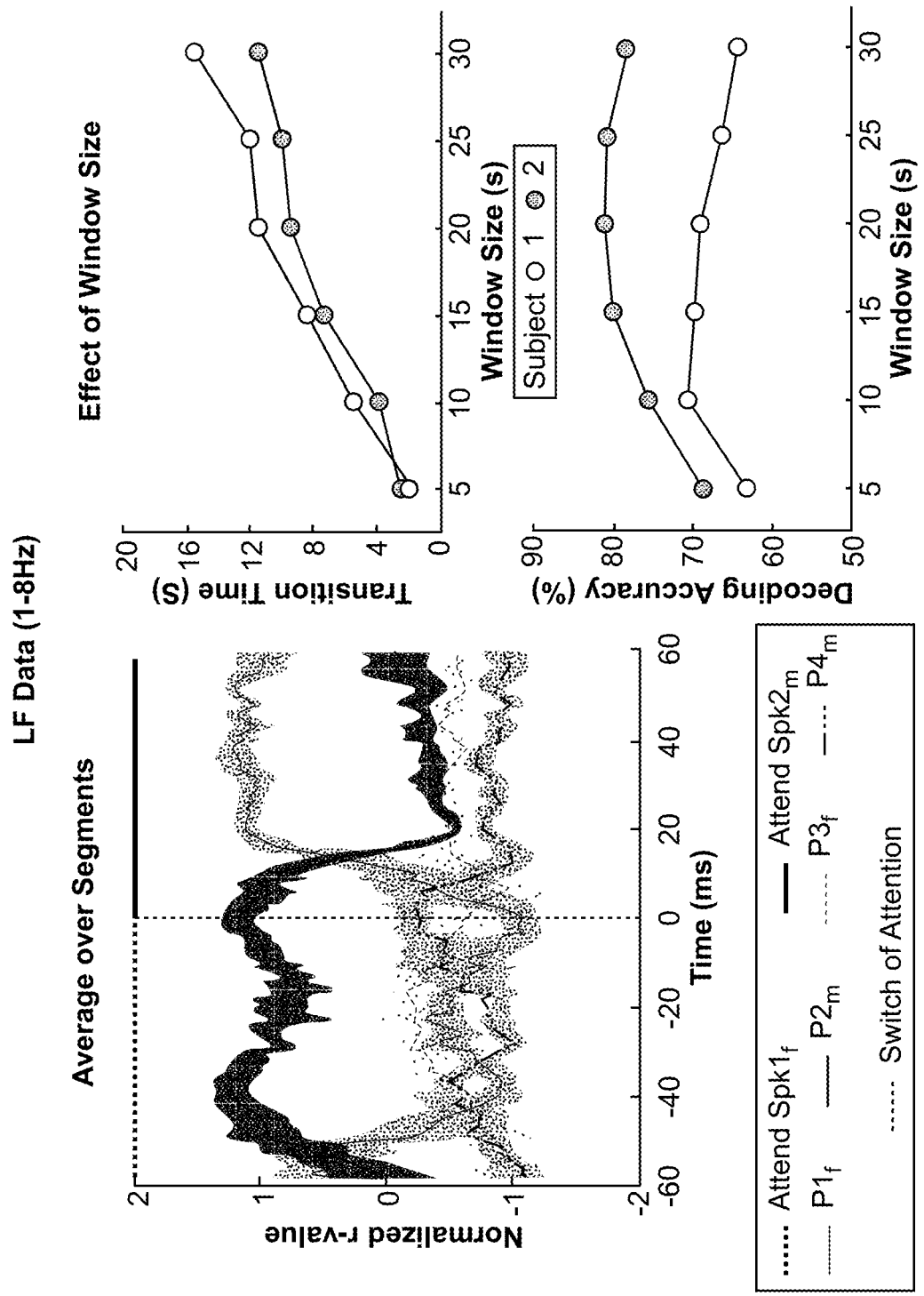

FIG. 8A displays the same results as shown in FIG. 7, but averaged over all sections when the subject was attending to Spk2*m* (−60 s–0 s) and Spk1*f* (0 s-60 s). Shaded regions denote standard error. This analysis was used in order to determine a measure of the transition time (how long it takes to detect a switch in attention for a subject). Transition times were calculated as the time at which the blue (Spk2M) and red (Spk1F) lines intersected in the averaged data. This calculation was performed for each subject whose attentional focus could be decoded and for all window-sizes (between 5 and 30 seconds; see FIG. 8B). For all subjects, the transition-time increases monotonically with larger window-sizes. Also shown is the decoding-accuracy that was achieved for each window-size (see FIG. 8B; bottom panel). These results suggest that window-sizes between 15 and 20 seconds achieve the best trade-off between speed and accuracy, and that longer window-sizes produce a reduction in decoding-accuracy. Larger window-sizes result in longer transition times, and therefore more false-positives after a switch in attention. FIG. 8C shows an example of the same analysis as in FIG. 8A, but instead uses LF data from subject 2. FIG. 8D illustrates the effect of the window size on transition-time and decoding-accuracy when using the LF data for subjects 1 and 2.

Figure 9A:
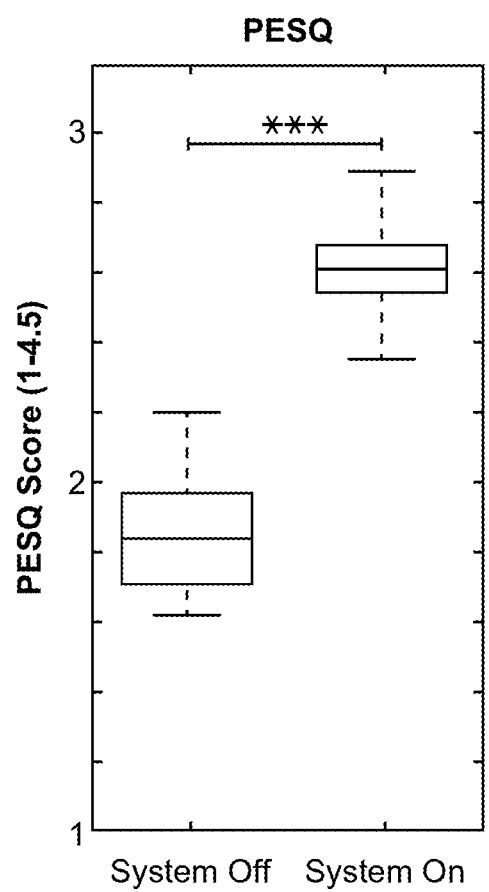
FIGS. 9A-B are graphs illustrating speaker separation quality results.

While the decoding-accuracy score (as presented in FIGS. 8A-D) is an important objective measure of performance, an objective of the experimentations and studies of the implementations described herein was to also enhance the quality of the audio by amplifying the attended speaker relative to the other sound sources. The quality of the output depends on a combination of factors including the accuracy of the DNN speech separation, the neural reconstruction, the attention decoding, and the amplification scheme. The quality of the final output audio was tested using both subjective and objective tests. The output of the system proposed herein produced an objectively cleaner speech signal with a significant increase in the Perceptual Evaluation of Speech Quality (PESQ) score (Wilcoxon signed-rank test, $p<0.001$; see FIG. 9A showing the PESQ results with the implemented system in OFF state and ON state).

To subjectively test the preference of users on the quality of the audio output of the systems described herein in a multi-speaker scenario, a psychoacoustic experiment was performed. More particularly, twelve subjects (seven female), aged between 20 and 28 years (mean±SD, 22±2.5) took part. All subjects reported normal hearing. The stimuli used for this experiment were the same as those used for the neural experiment, i.e. subjects were always presented with a mixture of Spk1F and Spk2M. However, the way the stimuli were presented was altered to obtain as much information as possible about the subjects' perception. The experiment was divided into four blocks, each containing fifteen (15) trials. Each trial included a single sentence. Before each block, the subjects were instructed to pay attention to one of the speakers (starting with the male) and to switch attention on each successive block. In order to test the intelligibility of the speech, after each trial (sentence) the subjects were presented with a transcription of the sentence of the attended speaker with one word missing. Subjects were instructed to type the missing word (the intelligibility task).

Figure 9B:
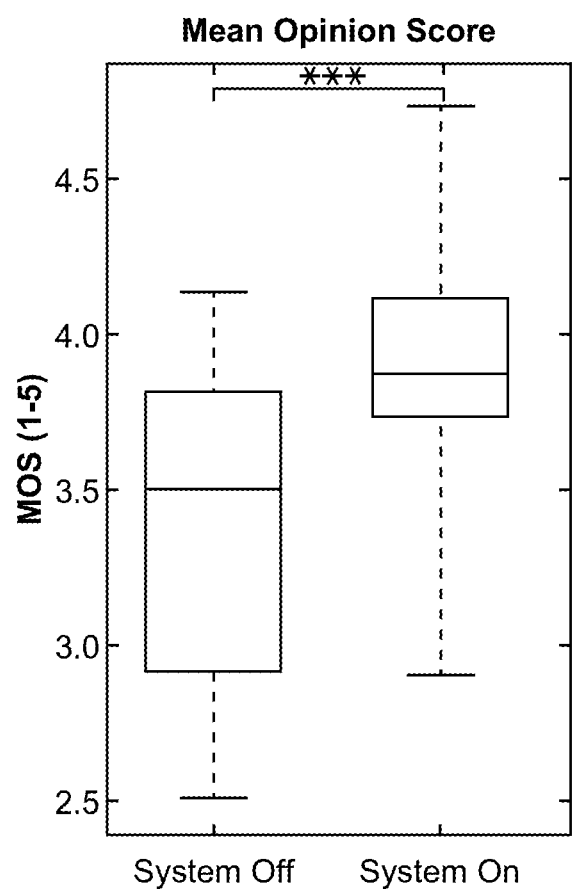

Subjects were also asked to indicate the difficulty they had understanding the attended speaker on a scale from 1 to 5, i.e., very difficult (1), difficult, not difficult, easy, and very easy (5). From these responses, the Mean Opinion Score (MOS) was calculated. This allowed obtaining both an objective measure of intelligibility and a subjective measure of listening effort (MOS). For half of the experiment, both speakers were presented at the same RMS power. For the other half, an attempt was made to amplify the attended speaker. Block order was counterbalanced across subjects. In total, the experiment lasted approximately 15 minutes, during which subjects were presented with 4 minutes and 11 seconds of audio. FIG. 9B is a graph showing the MOS scores when the system was off and on, and illustrates that MOS measures were significantly improved when the system was on. Particularly, all but one subject reported a larger MOS when the system was on, with a median MOS of 3.87 ($25^{th}$ percentile, 3.73; $75^{th}$ percentile, 4.12) versus a median MOS of 3.5 (25th percentile, 2.9; 75th percentile, 3.8) when the system was off. The one subject who reported no reduction in listening effort had almost identical MOS scores for both system on (3.7) and system off (3.8). The majority of subjects also reported a preference for the segments where the system was turned on (9 out of 12), and a majority reported a preference for using the system once they were informed of its nature (10 out of 12). In the missing word task, there was no significant difference in the numbers of words that were correctly reported when the system was on versus off. This lack of improved intelligibility is a well-known phenomenon in speech enhancement research where noise suppression does not typically improve intelligibly scores, even though the listening effort is reduced.

As part of the psychoacoustic experimentation conducted herein, real neural data was used to demonstrate how the overall system could be implemented. Specifically, the neural data from one of the subjects (subject 2) was used. To dynamically track the attentional focus of the subject, a strategy similar to the artificial switching of attention discussed earlier was implemented, i.e., use a sliding window approach, attempting to decode the attention of the subject every second. LF data was used, as opposed to the HF data, to be as comparable as possible with noninvasive technologies which typically only have access to low-frequency neural activity. Additionally, a window size of 20 seconds was used in order to be consistent with the decoding strategies discussed herein. Whenever it was possible to correctly classify the attended speaker from the neural data for that subject, the output from the correct DNN was added to the mixture. However, if a mistake was made, and the subject's attentional focus was misclassified, the output from whichever DNN produced the largest normalized correlation was presented. The DNN output was added at a level of +12 dB relative to the mixture. In addition to obtaining measures of intelligibility and listening effort, a determination of the participants' overall preference was made. Subjects were informed before the experiment that they would have to report which half of the experiment required less effort to understand the attended speaker, and were reminded half way through. The experimentation also asked the users as to whether they would prefer to use the system if they knew that it was not perfect.

Thus, as discussed herein, an end-to-end system that incorporates a single channel automatic speech-separation process into the auditory attention-decoding (AAD) platform was described. The approaches discussed herein alleviate the spatial separation requirements of multi-channel approaches, but can also be used in tandem with beamforming methods for optimal source separation. In addition to successfully identifying the attended speaker, the implementations described herein also amplify that speaker, resulting in an improvement in the subjective quality of the listening experience. Combined with the latest developments in AAD research, the systems described herein can be used to realize hearing aid devices that can automatically and dynamically track a user's direction of attention, and amplify an attended speaker (and/or attenuate non-attended speaker(s)). In some embodiments, neurological signals can be obtained through invasive ECoG recordings from neurological patients, which allows examining the upper bound of decoding speed and accuracy, determining the varying contributions of different auditory cortical areas, and separately examining attention decoding using low (1-8 Hz) and high (70-150 Hz) frequency neural data. In some embodiments, neural data may be obtained also through non-invasive neural recordings.

While the subjects in the experiments conducted for the implementations described herein were only presented with mixtures of two speakers (Spk1F and Spk2M), the implementations can be extended to a more general case of multiple speakers. Each DNN of the implementation may therefore be able to separate a trained target speaker from other unseen speakers.

The proposed system can switch to default operation when no target speaker is detected. Generally, a new speaker can be easily added to the system, requiring only a small amount of clean speech from the new target speaker (e.g., ~20 minutes). Because the reconstruction process from neural data may be achieved using single speaker data training, adding a new speaker does not involve recording new neural responses for that speaker. A practical limitation for all processes intended for hearing aids (or other hearing augmentation devices) is that hardware constraints could limit the number of DNNs that could be housed inside a portable device. However, modern hearing aids are able to perform off-board computing by interfacing with a cell phone, and specialized hardware is also becoming available for low-power neural network implementations. Another consideration is the fact that DNNs rely heavily on the data used to train them. Therefore, additional training may be required to separate speakers under different environmental conditions. Also, because people tend to involuntarily speak louder in noisy situations, which affects acoustic features such as pitch, rate and syllable duration, this would also need to be taken into account during training of the DNNs.

It was determined that the reconstructed spectrograms in data had a high correlation with the raw mixture. This is a problem that needs to be addressed, because a DNN is likely to output the mixture when its designated speaker is not present. The reason why the reconstructed spectrograms had such a high correlation with the mixture can be understood by looking at the single-electrode analysis. It was determined that many speech responsive electrodes are not modulated by attention, and instead encode both the attended and unattended speakers. Therefore, training decoders using all speech-responsive electrodes will lead to reconstructions that are similar to the mixture. The analysis also revealed that the location of electrodes in the brain played an important role in decoding attention. This result is likely due to the variable degree of attentional modulation in various parts of the auditory system. There was also a dichotomy between the high and low frequency data, where the accuracy of decoding was not always related, possibly due to the different neural generators of these two frequency bands.

In a real-world situation, it is likely that users would want to dynamically switch their attention between multiple speakers as a conversation progresses. Although the subjects in the experiments conducted for the implementations described herein alternated their attention between two speakers, they did not do so in a dynamic fashion. Rather, there was a substantial break between each block of the experiment. When simulating switching of attention, the window size used for estimation has an effect on both decoding-accuracy and transition-time (the time it takes to detect a switch in attention). The results of the experiments indicated that there is an optimal window-size for decoding-accuracy: shorter window sizes produce r-values that are too noisy, and longer window sizes prohibit the rapid detection of switches in attention. This problem is particularly important when using neural signals with a lower signal to noise ratio (such as around the ear, or in ear EEG). It is possible that more elaborate decoding processes can be used to speed up decoding and provide a better trade-off between decoding-accuracy and transition-time.

One important requirement of speech enhancement techniques is to ensure that the resulting speech is not distorted or corrupted, as users tend to prefer no enhancement over an amplified but distorted signal. In the experiments conducted, the automatically separated target speaker was amplified by +12 dB relative to the mixture. This level has been shown to significantly increase the intelligibility of an attended speaker in a two-talker scenario (from ≈88% to 98%). Importantly, an unattended speaker should still be audible so that users can switch their attention should they choose to do so. It is still possible to understand speakers when they are attenuated by 12 dB, although intelligibility drops to ≈78%. These parameters need to be further optimized when this type of system is tested in hearing impaired listeners and in closed-loop setups, where the decoding processes and a subject's brain can co-adapt to converge to a suitable solution. It was determined that there is a noticeable increase in the mean opinion score (MOS) when the implementations described herein were used, and almost all subjects reported that they would prefer to have the system turned on, a finding that supports the implementations' potential as a useful and effective way to identify and amplify an attended speaker.

Deep Attractor Network for Signal Separation

As noted, in some embodiments, a deep learning framework, also referred to as the attractor network, is implemented to solve the source separation problem. The term attractor is motivated by the well-studied perceptual effects in human speech perception which suggest that the brain circuits create perceptual attractors (magnets) that warp the stimulus space so as to draw the sound that is closest to it, a phenomenon that is called Perceptual Magnet Effect. The proposed model works on the same principle by forming a reference point (attractor) for each source in the embedding space which draws all the T-F bins toward itself. Using the similarity between the embedded points and each attractor, a mask is estimated for each sources in the mixture. Since the mask is directly related to the attractor point, the proposed framework can potentially be extended to arbitrary number of sources without the permutation problem. Moreover, the mask learning allows a very efficient end-to-end training scheme and highly reduces the computation complexity compared with the deep-clustering (DC) approach and the permutation invariant training (PIT) approach. In deep clustering, a network is trained to generate discriminative embedding for each time-frequency (T-F) bin with points belonging to the same source forced to be closer to each other. DC is generally able to solve both permutation and output dimension problem to produce the state of the art separation performance. A drawback of DC is its relative inefficiency to perform end-to-end mapping, because the objective function is the affinity between the sources in the embedded space and not the separated signals themselves. Minimizing the separation error is done with an unfolding clustering system and a second network, which is trained iteratively and stage-by-stage to ensure convergence. The PIT algorithm solves the permutation problem by pooling over all possible permutations for N mixing sources (N! permutations), and using the permutation with lowest error to update the network. The PIT approach was shown to have comparable performance as DC. However, PIT approach suffers the output dimension mismatch problem because it assumes a fixed number of sources. PIT also suffers from its computation efficiency, where the prediction window has to be much shorter than context window due to the inconsistency of the permutation both across and within sample segments.

Figure 10:
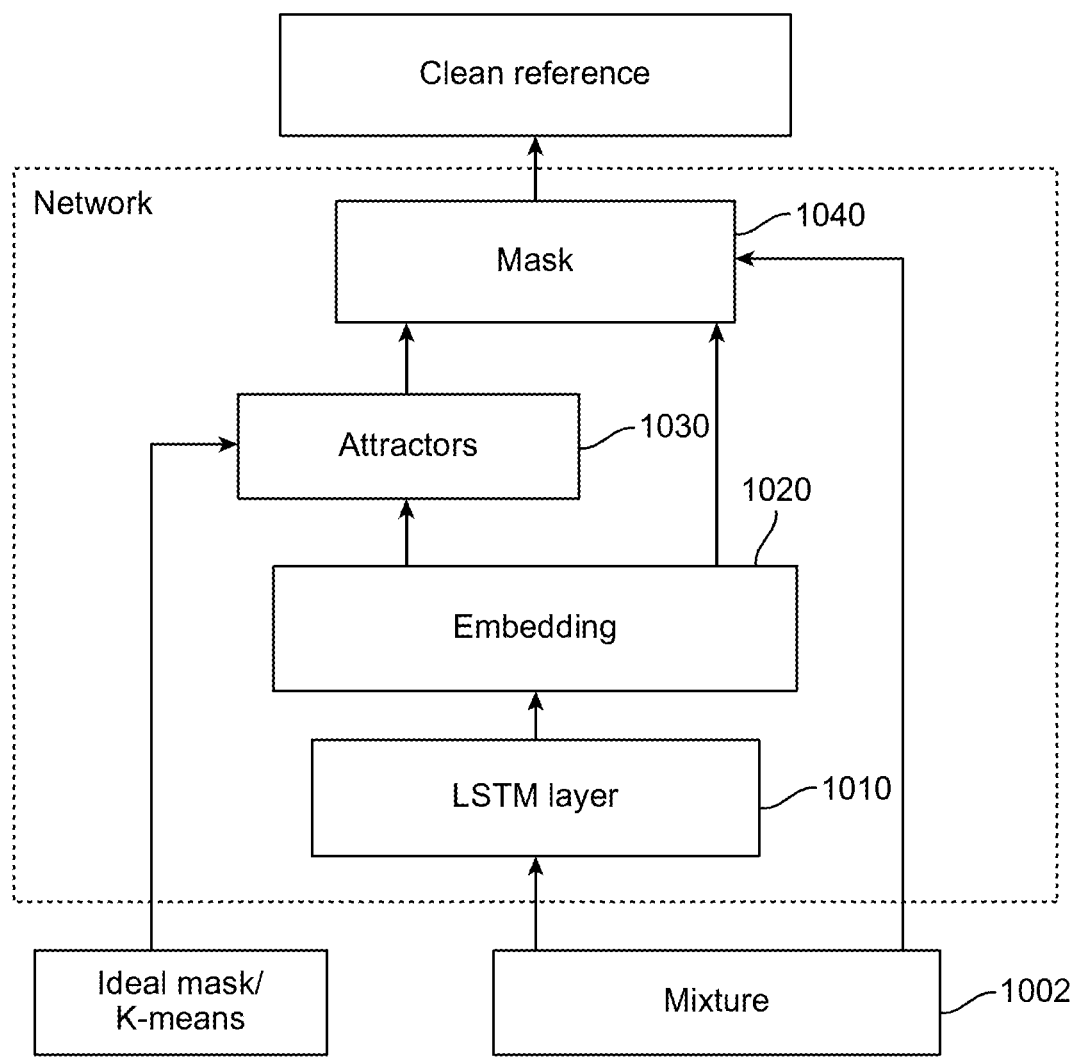
FIG. 10 is a diagram of a proposed system architecture to implement a deep-attractor network (DANet) approach.

With reference to FIG. 10, a diagram of a proposed system architecture 1000 to implement a deep-attractor network approach is provided. As shown, the system 1000 receives as input a mixture signal 1002 (e.g., a multi-speaker combined signal) via an input sensor (e.g., a single or multiple microphones coupled to a device such as a hearing devices, or some other hearing augmentation device). The received input mixture signal 1002 is provided to a deep learning neural network 1010, which may be implemented, for example, as an LSTM layer. In some embodiments, the neural network is trained to map the mixture sound X to a k dimensional embedding space (represented by the box 1020), such that it minimizes an objective function such as the following:

$$\mathcal{L} = \Sigma_{f,t,c} \|S_{f,t,c} - X_{f,t} \times M_{f,t,c}\|_2^2 \quad (7)$$

where S is the clean spectrogram (frequency F×time T) of C sources, X is the mixture spectrogram (frequency F×time T), and M is the mask formed to extract each source. Other objective functions may also be used.

The mask is estimated in the K dimensional embedding space of each T-F bin, represented by $V \in \mathbb{R}^{FT \times K}$:

$$M_{f,t,c} = \text{Sigmoid}(\Sigma_k A_{c,k} \times V_{ft,k}) \quad (8)$$

where $A \in \mathbb{R}^{C \times K}$ are the attractors (represented in box 1030) for the C sources in the embedding space, learned during training, which are defined as $$A_{c,k} = \frac{\Sigma_{f,t} V_{k,ft} \times Y_{c,ft}}{\Sigma_{f,t} Y_{c,ft}} \quad (9)$$

where $Y \in \mathbb{R}^{FT \times C}$ is the source membership function for each T-F bin, i.e., $Y_{tf,c}=1$ if source c has the highest energy at time t and frequency f compare to the other sources.

The objective function in Equation 7 includes of three parts. During training, an embedding V is first computed through a forward pass of the neural network for each given mixture. Then an attractor vector is estimated for each source using Equation 9. This can be done in several ways. The most straightforward method for attractor generation is to find the source centroid, as defined in Equation 9.

Next, a reconstruction mask is estimated (at box 1040) for each source by finding the similarity of each T-F bin in the embedding space to each of the attractor vectors A, where the similarity metric is defined in Equation 8. This particular metric uses the inner product followed by a sigmoid function which monotonically scales the masks between [0, 1]. Intuitively, if an embedding of a T-F bin is closer to one attractor, then it means that it belongs to that source, and the resulting mask for that source will produce larger values for that T-F bin. Since the source separation masks for each TF bin should add up to one, particularly in difficult conditions, the sigmoid function (of Equation 8) can be replaced with softmax function:

$$M_{f,t,c} = \text{Softmax}(\Sigma_k A_{c,k} \times V_{ft,k}) \quad (10)$$

Finally, a standard L2 reconstruction error is used to generate the gradient, as shown in Equation 7. Therefore, the error for each source reflects the difference between the masked signal and the clean reference, forcing the network to optimize the global reconstruction error for better separation. The proposed net is referred to as deep attractor network (DANet).

As noted, the DANet approach has several advantages. Firstly, DANet removes the stepwise pre-training process (required, for example, in the DC methodology) to allow end-to-end training. Another advantage of the DANet approach arises from flexibility in the number of sources in the mixture.

Figure 11A:
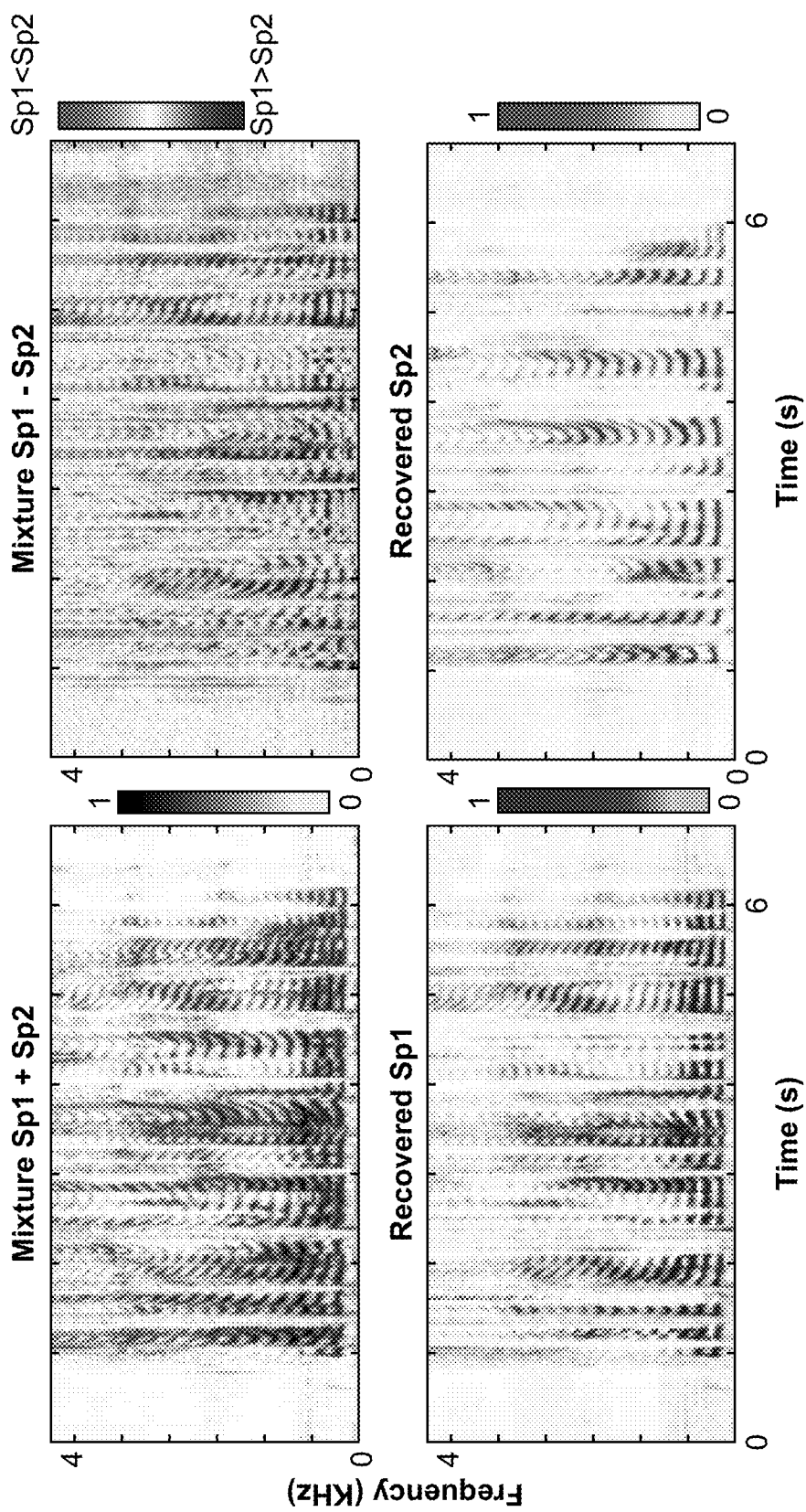
FIG. 11A includes graphs showing an example of a mixture, the difference between two speakers in the mixture, and the separated spectrograms of the two speakers using a DANet implementation.
Figure 11B:
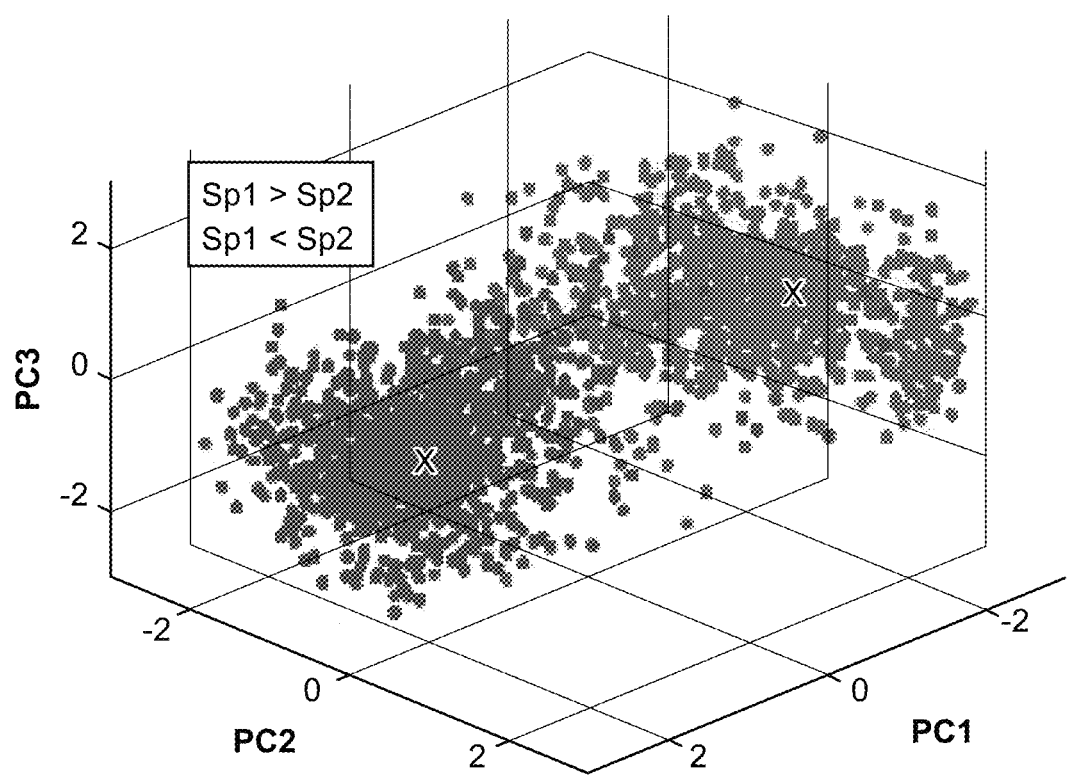
FIG. 11B is a graph showing locations of T-F bins in an embedding space.

Attractor points can be estimated using various processes other than the average-based approach. One possibility is to use weighted average. Since the attractors represent the sources' center of gravity, only the embeddings of the most salient T-F bins may be included, which leads to more robust estimation. This strategy can be investigated by using an amplitude threshold in the estimation of the attractor. Alternatively, a neural network model may also be used to pick the representative embedding for each source, an idea which shares similarities with encoder-decoder attention networks. During test time, because the true assignment Y is unknown, two strategies can be applied to form the attractor points. The first is similar to the strategy used in DC, where the centers are found using post K-means process. The second strategy is based on the observation that the location of the attractors in the embedding space is relatively stable. This observation is shown in FIGS. 11A-B, which includes, at FIG. 11A, graphs showing an example of a mixture, the difference between two speakers in the mixture, and the separated spectrograms of the two speakers using a DANet implementation, and, at FIG. 11B, a graph showing locations of T-F bins in the embedding space, where each pair of dots corresponds to the attractor found for the two speakers in a given mixture.

The objective function of DC is shown in Equation 11, where Y is the indicator function which is equivalent to a binary mask, and V is the learned embedding:

$$\mathcal{L} = \|YY^T - VV^T\|_2^2 \qquad (11)$$

Since Y is orthogonal and constant for each mixture, by multiplying $Y^T$ and a normalizer $U=(Y^T T)^{-1}$ to both terms, an objective function can be derived that is a special case of the attractor network, as in Equation 12:

$$\mathcal{L} = \|Y^T - UY^T VV^T\|_2^2 \qquad (12)$$

Figure 12:
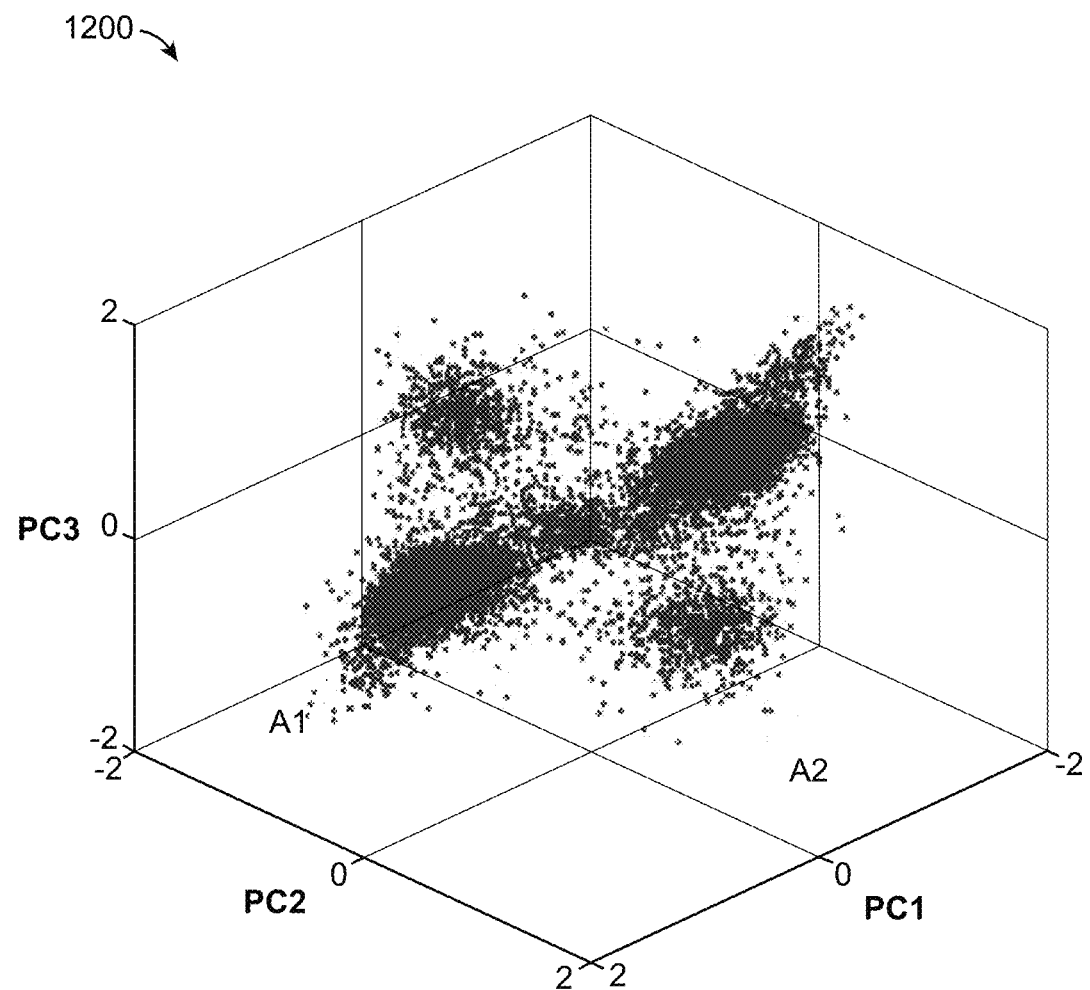
FIG. 12 is a graph presenting the locations of attractor points in the embedding space.

In Equation 12, $UY^T V$ can be viewed as an averaging operation, where the embeddings are summed according to the label, and the resulted center is multiplied with the embedding matrix V to measure the similarity between each embedding and the center, and compared with the ground truth binary mask. When the learned V is optimum, i.e., $VV^T = YY^T$, Equations 11 and 12 are equivalent. On the other hand, when the attractor vectors are considered as free parameters in the network, DANet reduces to a classification network, and Equation 7 becomes a fully-connected layer. In this case, PIT may become necessary because the mask has no information about the source and the problem of fixed output dimension arises. In contrast, the freedom of the network to form attractor points during the training allows the system to use the affinity between samples where no constraint is on the number of patterns found, therefore allowing the network to be independent of the number of sources. The flexibility of the network in choosing the attractor points is helpful even in two-source separation problems, because the two sources may have very different structures. As can be seen in FIG. 12, providing a graph 1200 presenting the locations of attractor points in the embedding space, the proposed implementations trained in speaker separation tasks have ended up finding 2 attractor pairs (4 points in the embedding space). More particularly, each point in FIG. 12 corresponds to one of 10,000 mixture sounds, visualized using the first three principal components. Two distinct attractor pairs (denoted as A1 and A2) are visible.

Figure 13:
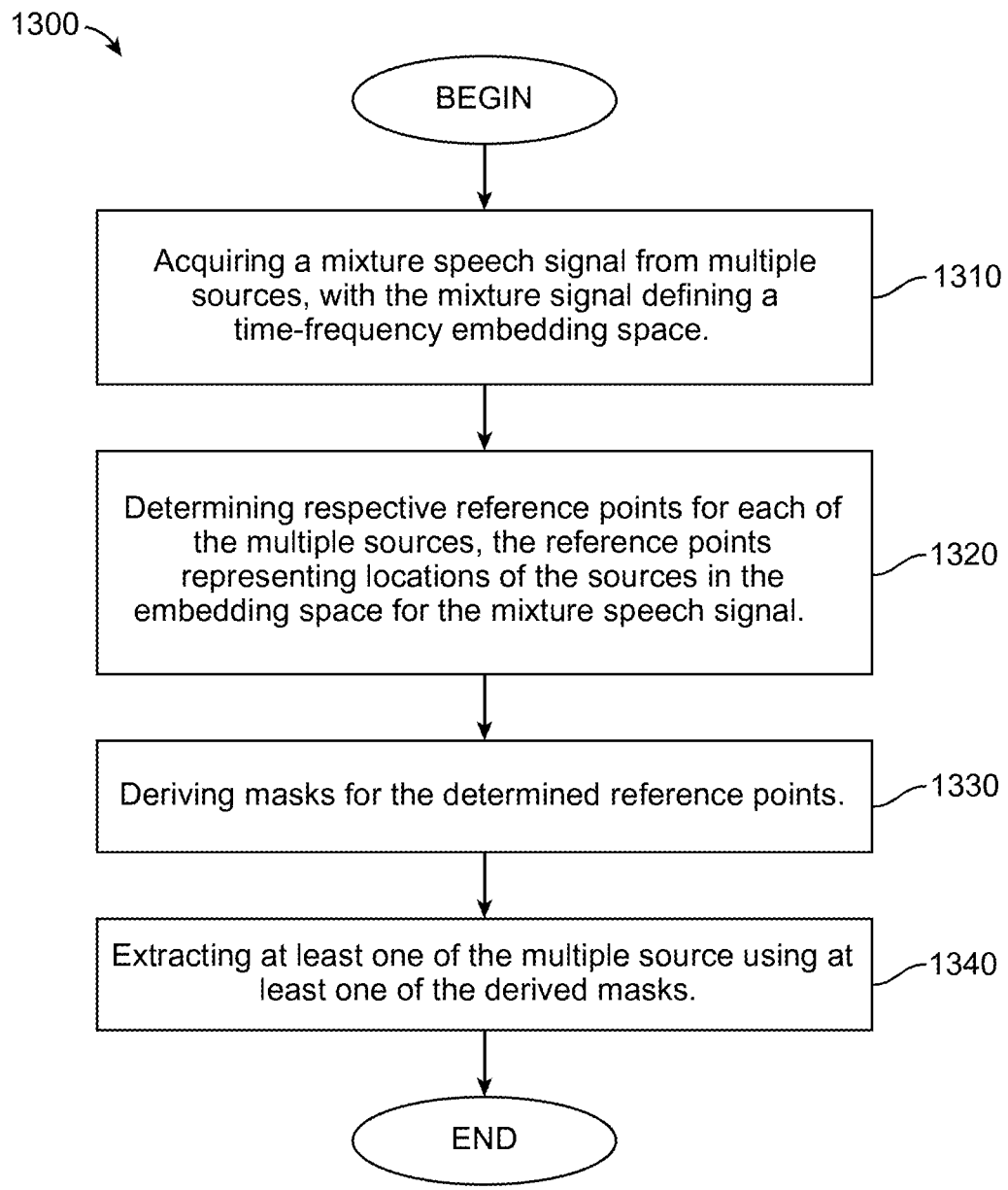
FIG. 13 is a flowchart of an example deep attractor signal separation procedure.

With reference now to FIG. 13, a flowchart of an example deep attractor signal separation procedure 1300 is shown. The procedure 1300 includes acquiring 1310 a mixture speech signal from multiple sources, the mixture signal defining a time-frequency embedding space. As discussed herein, the mixture signal may be the combined sounds signal of the procedure 300, which includes multiple sounds signals from multiple sounds sources. As also notes, the mixture speech signal may be obtained using a single audio sensor, such as a microphone, or multiple audio sensors. Having obtained the mixture speech signal, the procedure 1300 further includes determining 1320 respective reference points for each of the multiple sources, with the reference points representing locations of the sources in the embedding space for the mixture speech signal. The reference points may include attractor points in the embedding space. In some embodiments, determining the respective reference points may include determining the respective reference points using a deep neural network.

At 1330, the procedure 1300 further includes deriving masks for the determined reference points, and extracting 1340 at least one of the multiple sources using at least one of the derived masks. Deriving the masks may include computing similarity between embedded time-frequency points within the embedding space and the determined respective reference points.

As noted, the deep attractor network approach for speech separation may be used in many different application. For example, the DANet approach may be used to separate multi-speaker speech signals to implement attentional selection processing (i.e., enhance the speech signals of a speaker that the listener is determined to be listening to or focused on). In another example, the DANet approach may also be used in surveillance applications (to separate and record speech from a combined sound signal corresponding to different speakers), for virtual reality applications (reconstruct speaking objects from a pre-recorded source, and render the separated speech signals into a virtual audio, or audio-visual, scene), etc.

The deep attractor network implementations described herein were tested to evaluate their performance and efficacy. To that end, a system was realized for which a 30 hour training set and a 10 hour validation set, generated by randomly selecting utterances from different speakers in the Wall Street Journal (WSJ0) training data set si_tr_s was used. The data was mixed with various signal-to-noise ratios (SNR) randomly chosen between 0 dB and 10 dB. A five (5) hour evaluation set was generated similarly as above, using utterances from sixteen (16) unseen speakers from si_dt_05 and si_et_05 data in the WSJ0 dataset. Additionally, a three speaker mixture dataset was constructed for a three speaker separation evaluation from the same WSJ set, which had 30 hour training data, 10 hours validation data, and 5 hours testing data, mixed with SNR at −5~5 dB. Each three speaker mixture was ensured to include both female and male speakers. All data was re-sampled to 8 kHz to reduce computational and memory costs. The log spectral magnitude was served as an input feature, computed using short-time Fourier transform (STFT) with 32 ms window length, 8 ms hop size, and the square root of hanning window.

The network contained four (4) bi-directional LSTM layers with 600 hidden units in each layer. The embedding dimension was set to 20, resulting in a fully-connected feed-forward layer of 2580 hidden units (20×129) after the BLSTM layers. The input features were split into non-overlapping chunks of 100-frame length as the input to the network. An RMSprop procedure was used for training, with an exponential learning rate decaying strategy, where the learning rate started at $10^{-4}$ and ended at $3\times10^{-6}$. The total number of epochs was set to be 150, and a cost function was used in Equation 7 on the validation set for early stopping. The criteria for early stopping is no decrease in the loss function on validation set for 10 epochs. A Deep Clustering (DC) network was constructed with the same configuration, which was used as the baseline. The results were reported in terms of signal-to-distortion ratio (SDR, which was defined as scale-invariant SNR here), signal-to-artifacts ratio (SAR), and signal-to-interference ratio (SIR). The results are shown below in Table 1, which provides evaluation metrics for networks with different configurations.

TABLE 1

|  | GNSDR | GSAR | GSIR |
| --- | --- | --- | --- |
| DC | 9.1 | 9.5 | 22.2 |
| DANet | 9.4 | 10.1 | 18.8 |
| DANet-50% | 9.4 | 10.4 | 17.3 |
| DANet-70% | 9.6 | 10.3 | 18.7 |
| DANet-90% | 9.6 | 10.4 | 18.1 |
| DANet-90% (with curriculum training of 400-frame length input) | 10.5 | 11.1 | 20.3 |
| Fix-DANet-90% | 9.5 | 10.4 | 17.8 |

In Table 1 above, the percentage indicated represents the salient weigh threshold used during training. As indicated by the results of Table 1, although the plain DANet already outperforms the DC baseline, adding a simple threshold on T-F samples included in the formation of the attractor yields further improved performance, presumably due to the increased influence of salient segments. On the other hand, the performance boost suggests that better attractor formation procedures can be utilized to estimate the attractors, such as joint optimizing of the network parameters. Moreover, by applying curriculum training strategy, in which the network continues to be trained with 400-frame length input, DANet achieves the best overall performance.

In the last experiment presented in Table 1, a fixed pair of attention vector collected from the training data was used, corresponding to the A1 pair of FIG. 12. This pre-set attractor is able to generalize well to the unseen mixtures and produces high quality separation, but corresponds to slightly worse results than the best model. Compared with K-means, this has the advantage that it can be easily implemented in real-time using a frame-by-frame pipeline. Based on this observation, when more attractors are required (e.g. in more complex tasks), a collection of attractor codebook and a simple classifier could be implemented for real-time processing.

Next, in a three-speaker separation experiment, whose results are shown in Table 2 below, the proposed system significantly outperforms the deep clustering baseline. This result may be expected since deep clustering was trained to estimate binary mask, while the deep attractor network focuses on the signal reconstruction. When the mixture is relatively simple, the binary mask could generate high quality separation. However, for more complex mixtures, or when one source is significantly louder than the other, the binary mask usually leads to large bias to the loudest source, and thus result in unsatisfactory separation for the weaker source. Note that in the three speaker experiment, the network was trained using softmax objective as shown in Equation 10.

TABLE 2

|  | GNSDR | GSAR | GSIR |
| --- | --- | --- | --- |
| DC | 6.3 | 2.3 | 12.6 |
| DANet | 7.7 | 3.9 | 13.2 |
| DANet (with curriculum training of 400-frame length input) | 8.8 | 5.0 | 15.0 |

Thus, described herein are implementations of a neural network framework referred to as a deep attractor network for general source separation problem. The network forms attractor points in a high-dimensional embedding space of the signal, and the similarity between attractors and time-frequency embeddings are then converted into a soft separation mask. The proposed framework can perform end-to-end, real-time separation, and can work on different number of mixing sources. Evaluations and experimentations performed for the deep attractor network implementations for multi-speaker separation tasks confirmed its efficacy and potential for extension to general source separation problems.

Time-Domain Audio Separation Using a Deep Long-Short Term Memory Network (LSTM)

Another speech separation implementation that may be used in to separate the multi-speaker speech signals (e.g., as part of the attentional selection processes described herein, or for other applications such as virtual reality applications, surveillance applications, etc.) is the Time-domain Audio Separation Network (TasNet) process that uses a Deep Long-Short Term Memory Network (LSTM) for directly modelling a signal in the time-domain using an encoder-decoder framework (this separation process will henceforth be referred to as the "LSTM-TasNet" process). The LSTM-TasNet process performs source separation on nonnegative encoder outputs. The implementations described herein remove the frequency decomposition stage and reduce the separation problem to estimation of source masks on encoder outputs which is then synthesized by the decoder. The implementations described herein outperform state-of-the-art causal and non-causal speech separation systems, reduces the computational cost of speech separation, and reduces the minimum required latency of the output. This makes TasNet suitable for applications where low-power, real-time implementation is desirable, such as in hearable and telecommunication devices.

Generally, in a typical STFT-based system, the speech separation process starts with calculating the short-time Fourier transform to create a time-frequency (T-F) representation of the mixture sound. The T-F bins that correspond to each source are then separated, and are used to synthesize the source waveforms using inverse STFT. One issue that arises for STFT-based systems is that because STFT transforms the signal into a complex domain, the separation algorithm needs to deal with both magnitude and the phase of the signal. Because of the difficulty in modifying the phase, most SFFT-based systems only modify the magnitude of the STFT by calculating a time-frequency mask for each source, and synthesize using the masked magnitude spectrogram with the original phase of the mixture.

In the example implementations described herein of the LSTM TasNet process, a mixture waveform (i.e., the mixed signal resulting from the combining of speech signals produced by multiple speakers) is divided into non-overlapped segments, and each segment is represented as a weighted sum of a set of basis signals that is optimized automatically by the network, with (in some embodiments) the constraint that the weights be nonnegative. The time-domain signal can then be represented by a weight matrix, reformulating the waveform separation problem into estimating the weight matrices that correspond to different sources given the weight matrix of the mixture. A deep long-short term memory network (LSTM) is configured for this process. The synthesis of the sources signals is done by calculating the weighted sum of the bases with the estimated source weight matrices. Without the need for calculating short-time Fourier transform (STFT) and its inverse, this system has much shorter latency than STFT-based systems, where a spectrogram is typically taken as the input and a time-frequency mask as the output. Experiments show that the implementations described herein have significantly better performance compared with conventional causal systems. The implementations described herein have the potential to be deployed in hearing aids and real-time multi-talker recognition applications that have strict requirement about latency. Moreover, more complex mixtures such as music and environment sounds are also expected to be separated with this system architecture, leading to the possibility of a real-time universal separator.

Figure 14:
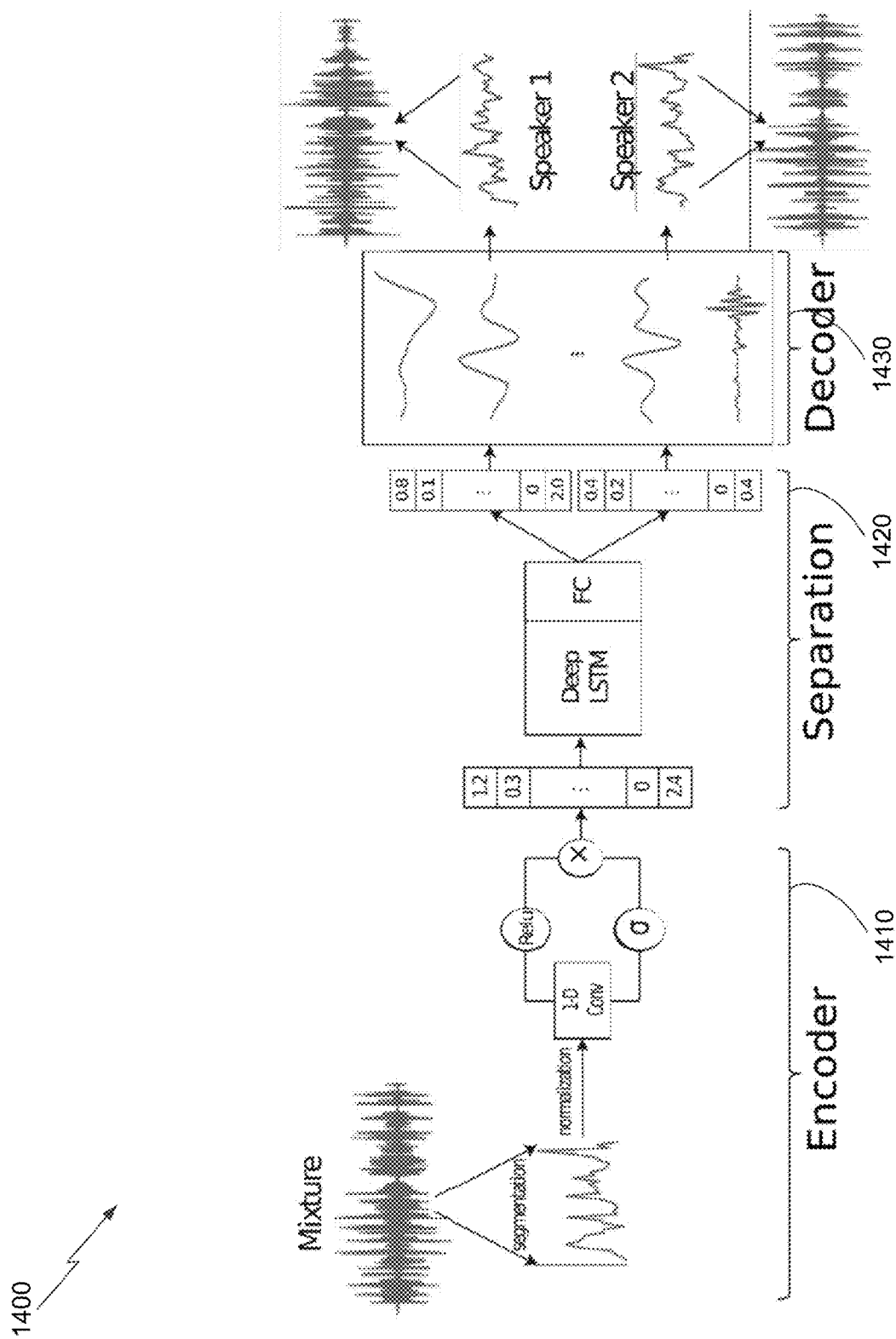
FIG. 14 is a schematic diagram of an example Long-Short Term Memory Network (LSTM) time-domain audio separation system.

Thus, with reference to FIG. 14, a schematic diagram of an example LSTM-TasNet system implementation 1400 to perform speech separation of a multi-speaker signal is shown. In the system implementation of FIG. 14, the Time-domain Audio Separation Network (TasNet) models the signal in the time-domain using encoder-decoder framework, and performs the source separation on nonnegative encoder outputs. Separation is achieved by estimating source masks that are applied to mixture weights to reconstruct the sources. The source weights are then synthesized by the decoder. The above example implementation contains three parts: an encoder 1410 for estimating the mixture weight, a separation module 1420, and a decoder 1430 for source waveform reconstruction. The combination of the encoder and the decoder modules construct a nonnegative autoencoder for the waveform of the mixture, where the nonnegative weights are calculated by the encoder and the basis signals are the 1-D filters in the decoder. The separation is performed on the mixture weight matrix using a subnetwork that estimates a mask for each source.

The encoder 1410 is configured to perform estimation of the nonnegative mixture weight $w_k$ for a segment k by a 1-D gated convolutional layer $$w_k = \text{ReLU}(x_k * U) \odot \sigma(x_k * V), k=1,2,\ldots,K$$

where $U \in R^{N \times L}$ and $V \in R^{N \times L}$ are N vectors with length L, and $w_k \in R^{1 \times N}$ is the mixture weight vector. σ denotes the Sigmoid activation function and * denotes a convolution operator. $x_k \in R^{1 \times N}$ is the $k^{th}$ segment of the entire mixture signal x(t) with length L, and is normalized to have unit $L^2$ norm to reduce the variability. The convolution is applied on the rows (time dimension). This process is motivated by the gated CNN approach that is used in language modeling, and empirically it performs significantly better than using only ReLU or Sigmoid.

In some embodiments, the encoder 1410 may also be configured to perform pre-processing on the combined signal (alternatively, a dedicated unit/processor may be configured to perform the pre-processing operations to produce resultant segments provided to the encoder 1410). For example, the pre-processing may include obtaining the combined sound signal for the signals formed from the multiple sound sources in an area in which a person is located, and dividing the combined sound signal into non-overlapping segments. Obtaining the combined sound signal may include obtaining the combined sound signal using a single microphone to receive the signals from the multiple sound sources (in some examples, multiple microphones may be used). The pre-processing operations of dividing the combined sound signal may include normalizing the non-overlapping segments.

As further illustrated above in FIG. 14, the separation module 1420 is configured the estimation of the source masks is done with a deep LSTM network to model the time dependencies across the K segments, followed by a fully-connected layer with Softmax activation function for mask generation. The input to the LSTM network is the sequence of K mixture weight vectors $w_1, \ldots, w_K \in R^{1 \times N}$, and the output of the network for source i is K mask vectors $m_{i,1}, \ldots, m_{i,K} \in R^{1 \times N}$. The procedure for estimation of the masks is similar to a T-F mask estimation process, where a set of masks are generated by several LSTM layers followed by a fully-connected layer with Softmax function as activation.

To speed up and stabilize the training process, the mixture weight vector $w_k$ is normalized in a way similar to layer normalization:

$$\hat{w}_k = \frac{g}{\sigma} \otimes (w_k - \mu) + b, k = 1, 2, \ldots, K$$

$$\mu = \frac{1}{N}\sum_{j=1}^{N} w_{k,j} \quad \sigma = \sqrt{\frac{1}{N}\sum_{j=1}^{N}(w_{k,j} - \mu)^2}$$

where parameters $g \in R^{1 \times N}$ and $b \in R^{1 \times N}$ are defined as the gain and bias vectors that are jointly optimized with the network. This normalization step results in scale invariant mixture weight vectors and also allows more efficient training for the LSTM layers. In some embodiments, starting from the second LSTM layer, an identity skip connection is added between every two LSTM layers to enhance the gradient flow and accelerate the training process.

With continued reference to FIG. 1, for the decoder stage 1430, the separation network produces a mask matrix for each source i $M_i=[m_{i,1}, \ldots, m_{i,K}] \in R^{K \times N}$ from the mixture weight $\hat{W}=[\hat{w}_1, \ldots, \hat{w}_K] \in R^{K \times N}$ across all the K segments. The source weight matrices can then be calculated by:

$$D_i = \hat{W} \odot M_i,$$

where $D_i=[d_{i,1}, \ldots, d_{i,K}] \in R^{K \times N}$ is the weight matrix for source i. Note that $M_i$ is applied to the original mixture weight $W=[w_1, \ldots, w_K]$ instead of normalized weight $\hat{W}$. The time-domain synthesis of the sources is done by matrix multiplication between $D_i$ and the basis signals $B \in R^{N \times L}$ according to $S_i=D_iB$.

For each segment, this operation can also be formulated as a linear deconvolutional operation (also known as transposed convolution), where each row in B corresponds to a 1-D filter which is jointly learned together with the other parts of the network. This is the inverse operation of the convolutional layer discussed in relation to the encoder stage. Finally, the recovered signals is scaled to reverse the effect of $L^2$ normalization of $x_k$. Concatenating the recoveries across all segments reconstruct the entire signal for each source yields:

$$s_i(t)=[S_{i,k}], k=1,2,\ldots,K.$$

Since the output of the network are the waveforms of the estimated clean signals, source-to-distortion ratio (SDR) can be directly used as the training target. Here a scale-invariant source-to-noise ratio (SI-SNR) is used as the evaluation metric in place of the standard SDR. The SI-SNR is defined as:

$$s_{target} = \frac{\langle \hat{s}, s \rangle s}{\|s\|^2}$$

$$e_{noise} = \hat{s} - s_{target}$$

$$SI-SNR = 10\log_{10}\frac{\|s_{target}\|^2}{\|e_{noise}\|^2}$$

where $\hat{s} \in R^{1 \times t}$ and $s \in R^{1 \times t}$ are the estimated and target clean sources respectively, t denotes the length of the signals, and $\hat{s}$ s are both normalized to have zero-mean to ensure scale-invariance. Permutation invariant training (PIT) is applied during training to remedy the source permutation problem.

Thus, in some embodiments, a system is provided that includes at least one microphone to obtain a combined sound signal for signals combined from multiple sound sources in an area in which a person is located, and a controller coupled to the at least one microphone. The controller is configured to divide the combined sound signal into non-overlapping segments, transform the non-overlapping segments into respective weighted sums of a learnable overcomplete basis of signals, with weight coefficients for the respective weighted sums being non-negative, perform neural-network-based processing on the respective weighted sums of the learnable overcomplete basis of signals to derive a plurality of mask matrices corresponding to different groups of the multiple sound sources, and estimate a plurality of reconstructed sounds signals from the derived plurality of mask matrices corresponding to the different groups of the multiple sound sources.

Figure 15:
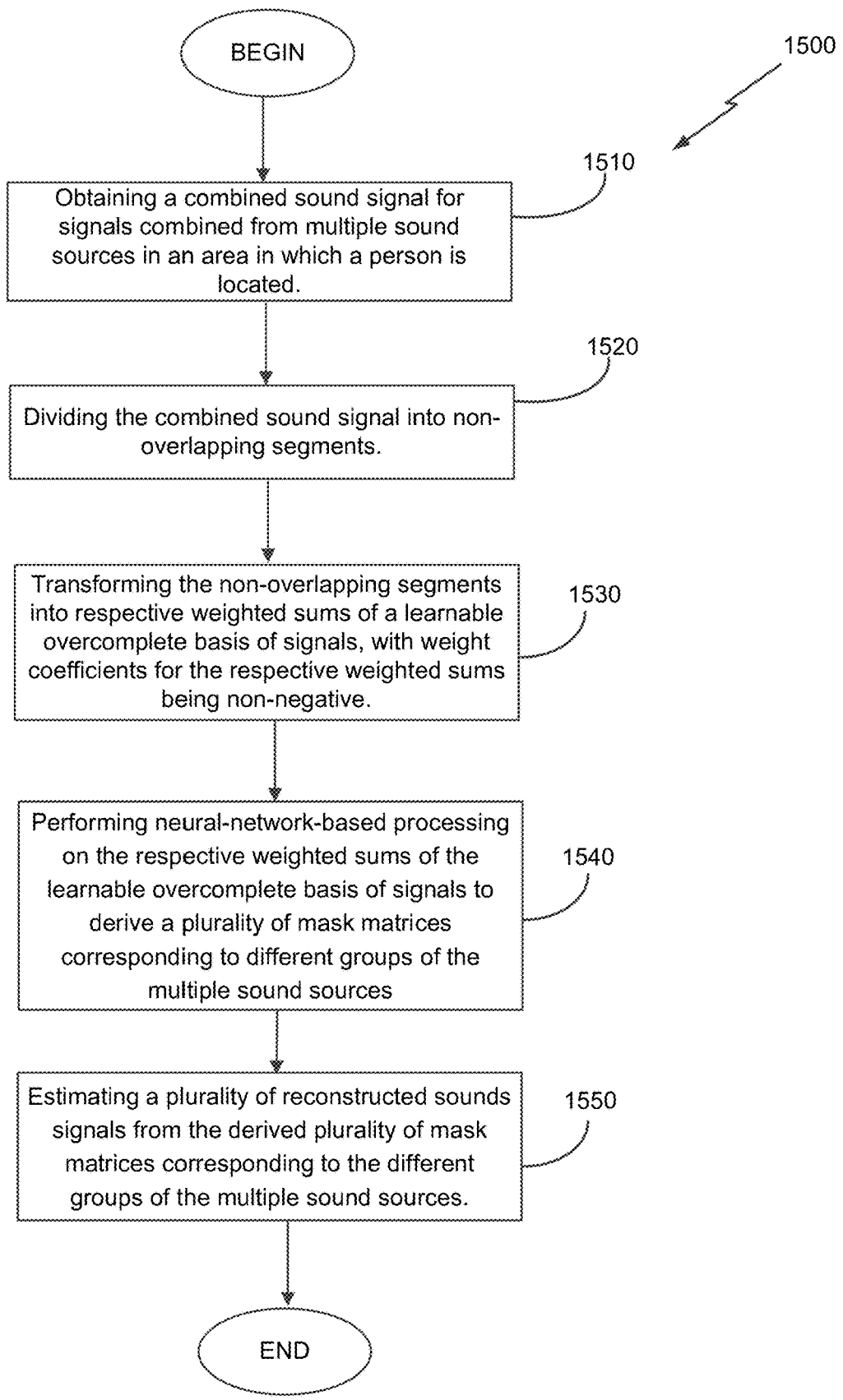
FIG. 15 is a flowchart of an example procedure to separate speech signals using an LSTM-TasNet approach.

With reference to FIG. 15, a flowchart of an example procedure 1500 to separate speech signals is shown. The procedure 1500 includes obtaining 1510 a combined sound signal for signals combined from multiple sound sources (e.g., from multiple speakers) in an area in which a person is located. Obtaining the combined sound signal may include obtaining the combined sound signal using a single microphone to receive the signals from the multiple sound sources. The procedure 1500 further includes dividing 1520 the combined sound signal into non-overlapping segments. Dividing the combined sound signal into the non-overlapping segments may include normalizing the non-overlapping segments.

As further illustrated in FIG. 15, the procedure 1500 additionally includes transforming 1530 the non-overlapping segments into respective weighted sums of a learnable overcomplete basis of signals, with weight coefficients for the respective weighted sums being non-negative. In some embodiments, transforming the non-overlapping segments into the respective weighted sums may include estimating the respective weighted sums of the learnable overcomplete basis of signals using a gated 1-D convolution layer according to:

$$w_k = ReLU(x_k * U) \odot \sigma(x_k * V), k=1,2,\ldots K,$$

with $U \in R^{N \times L}$ and $V \in R^{N \times L}$ being N vectors with length L, $w_k \in R^{1 \times N}$ is a mixture weight vector for segment k, $\sigma$ denotes a Sigmoid activation function, and * denotes a convolution operator.

The procedure 1500 also includes performing 1540 neural-network-based processing on the respective weighted sums of the learnable overcomplete basis of signals to derive a plurality of mask matrices corresponding to different groups of the multiple sound sources. In some examples, performing neural-network-based processing on the respective weighted sums to derive the plurality of mask matrices may include inputting the respective weighted sums of the learnable overcomplete basis of signals to a deep long-short term network (LSTM) followed by a fully connected layer with Softmax activation function for mask generation.

The procedure further includes estimating 1550 a plurality of reconstructed sounds signals from the derived plurality of mask matrices corresponding to the different groups of the multiple sound sources. In some embodiments, estimating the plurality of reconstructed sounds signals may include computing a source weight matrix, $D_i$, according to $D_i = W \odot M_i$, where $D_i = [d_{i,1}, \ldots, d_{i,K}] \in R^{K \times N}$ is the weight matrix for source i, and synthesizing a time-domain synthesis of the sources by multiplying the weight matrix $D_i$ with basis signals $B \in R^{N \times L}$.

Testing and evaluations were performed for some of the implementation described herein for the LSTM-TasNet approach. An example system implementation was evaluated for a two-speaker speech separation problem using WSJ0-2mix dataset, which contains 30 hours of training and 10 hours of validation data. The mixtures were generated by randomly selecting utterances from different speakers in Wall Street Journal (WSJ0) training set si_tr_s, and mixing them at random signal-to-noise ratios (SNR) between 0 dB and 5 dB. Five hours of evaluation set was generated in the same way, using utterances from 16 unseen speakers from si_dt_05 and si_et_05 in the WSJ0 dataset. To reduce the computational cost, the waveforms were down-sampled to 8 kHz.

The parameters of the system included a segment length L, the number of basis signals N, and the configuration of the deep LSTM separation network. Using a grid search, the optimal L was found to be 40 samples (5 ms at 8 kHz) and N to be 500. A 4 layer deep uni-directional LSTM network was implemented with 1000 hidden units in each layer, followed by a fully-connected layer with 1000 hidden units that generated two 500-dimensional mask vectors. For the noncausal configuration with bi-directional LSTM layers, the number of hidden units in each layer was set to 500 for each direction. An identical skip connection was added between the output of the second and last LSTM layers.

During training, the batch size was set to 128, and the initial learning rate was set to $3e^{-4}$ for the causal system (LSTM) and $1e^{-3}$ for the noncausal system (BLSTM). The learning rate was halved if the accuracy on validation set was not improved in three (3) consecutive epochs.

The criteria for early stopping was observance of no decrease in the cost function on the validation set for 10 epochs. The stochastic optimization "Adam" was used as the optimization process. No further regularization or training procedures were used. A curriculum training strategy was applied in a similar fashion. Training the network was commenced on 0.5 second long utterances, with the training continued on 4 second long utterances afterward.

For comparison with previous studies, the system was evaluated with both SI-SNR improvement (SI-SNRi, as defined above) and with the SDR improvement (SDRi)

metrics. Table 3, below shows the performance of tested system implementation, as well as example other convention deep speech separation systems, namely, Deep Clustering (DPCL++), Permutation Invariant Training (PIT), and Deep Attractor Network. Here LSTM-TasNet represents the causal configuration with uni-directional LSTM layers. TasNet-BLSTM corresponds to the system with bi-directional LSTM layers which is noncausal and cannot be implemented in real-time.

TABLE 3

| Method | Causal | SI-SNRi | SDRi |
|---|---|---|---|
| uPIT-LSTM | ✓ | — | 7.0 |
| TasNet-LSTM | ✓ | 7.7 | 8.0 |
| DPCL++ | X | 10.8 | — |
| DANet | X | 10.5 | — |
| uPIT-BLSTM-ST | X | — | 1-.0 |
| TasNet-BLSTM | X | 10.8 | 11.1 |

With causal configuration, the proposed LSTM-TasNet system significantly outperforms the state-of-art causal system which uses a T-F representation as input. Under the noncausal configuration, the LSTM-TasNet systems described herein provided strong performance. It is to be noted that the LSTM-TasNet systems did not contain any regularizers such as recurrent dropout (DPCL++) or post-clustering steps for mask estimation (DANet).

Table 4, below compares the latency of different causal systems. The latency of a system Trot is expressed in two parts: $T_i$ is the initial delay of the system that is required in order to receive enough samples to produce the first output. $T_p$ is the processing time for a segment, estimated as the average per-segment processing time across the entire test set. The model was pre-loaded on a Titan X Pascal GPU before the separation of the first segment started. The average processing speed per segment in our system is less than 0.23 ms, resulting in a total system latency of 5.23 ms. In comparison, a STFT-based system requires at least 32 ms time interval to start the processing, in addition to the processing time required for calculation of STFT, separation, and inverse STFT. This allows some of the example systems described herein to preform in situations that can tolerate only short latency, such as hearing devices and telecommunication applications.

TABLE 4

| Method | $T_i$ | $T_p$ | $T_{tot}$ |
|---|---|---|---|
| uPIT-LSTM | 32 | — | >32 |
| TasNet-LSTM | 5 | 0.23 | 5.23 |

Figure 16:
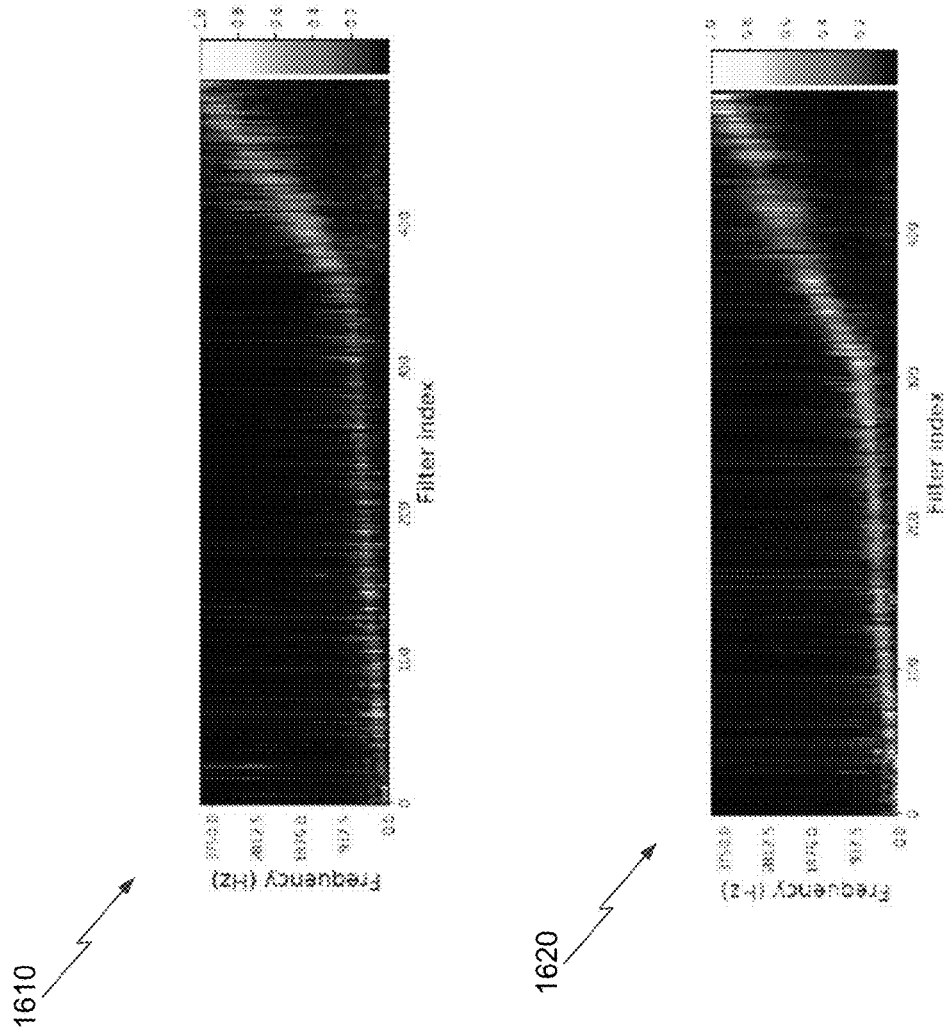
FIG. 16 includes graphs showing the frequency response of basis signals, sorted by their center frequencies, for causal and non-causal networks.

To investigate the properties of the basis signals B, the magnitude of their Fourier transform was visualized in both causal and noncausal networks. FIG. 16 includes graphs 1610 and 1620 for causal and non-causal networks, respectively, showing the frequency response of the basis signals sorted by their center frequencies (i.e. the bin index corresponding to the peak magnitude). A continuous transition from low to high frequency can be observed, showing that the system has learned to perform a spectral decomposition of the waveform. It can also be observed that the frequency bandwidth increases with center frequency similar to mel-filter banks. In contrast, the basis signals in TasNet have a higher resolution in lower frequencies compared to Mel and STFT. In fact, 60% of the basis signals have center frequencies below 1 kHz, which may indicate the importance of low-frequency resolution for accurate speech separation.

Convolutional Encoder for a Time-Domain Audio Separation Network

Yet another speech separation approach implementation that may be used to separate the multi-speaker speech signals (e.g., as part the of the attentional selection processes described herein, and/or other types of applications, such as virtual and augmented reality applications, surveillance applications, etc.) is a convolutional encoder approach for Time-domain Audio Separation Network (TasNet) (this separation process will henceforth be referred to as the "Convolutional TasNet" or "Conv-TasNet" process).

The convolution TasNet systems, methods, and other implementations described herein implement a deep learning autoencoder framework for time-domain speech separation. TasNet uses a convolutional encoder to create a representation of the signal that is optimized for extracting individual speakers. Speaker extraction is achieved by applying a weighting function (mask) to the encoder output. The modified encoder representation is then inverted to the sound waveform using a linear decoder. The masks are found using a temporal convolution network comprising of dilated convolutions, which allow the network to model the long-term dependencies of the speech signal. This end-to-end speech separation approach provides good performance in terms of separating speakers in mixed audio. In addition, the convolutional TasNet approach has a small model size and a short minimum latency, making it a suitable solution for both offline and real-time speech separation applications. This approach therefore allows for actualizing speech separation for real-world speech processing technologies.

The convolutional TasNet implementations described herein use a stacked dilated 1-D convolutional networks. This approach is motivated by the success of temporal convolutional network (TCN) models which allow parallel processing on consecutive frames or segments to speed up the separation process. This approach also reduces the model size. To further decrease the number of parameters and the computational complexity of the system, the original convolution operation is replaced with depth-wise separable convolution. Such a configuration provides high separation accuracy. The separation accuracy of Conv-TasNet surpasses the performance of ideal time-frequency masks, including the ideal binary mask (IBM), ideal ratio mask (IRM), and Winener filter-like mask (WFM). Each layer in a TCN contains a 1-D convolution block with increasing dilation factors. The dilation factors increase exponentially to ensure a sufficiently large temporal context window to take advantage of the long-range dependencies of the speech signal. In Conv-TasNet implementations, M convolution blocks with dilation factors 1, 2, 4, . . . , $2^{M-1}$ are repeated R times. The output of the last block in the last repeat is then passed to a 1×1 convolutional layer with N×C filters followed by a Softmax activation function to estimate C mask vectors for each of the C target sources. The input to each block may be zero padded to ensure the output length is the same as the input.

Figure 17:
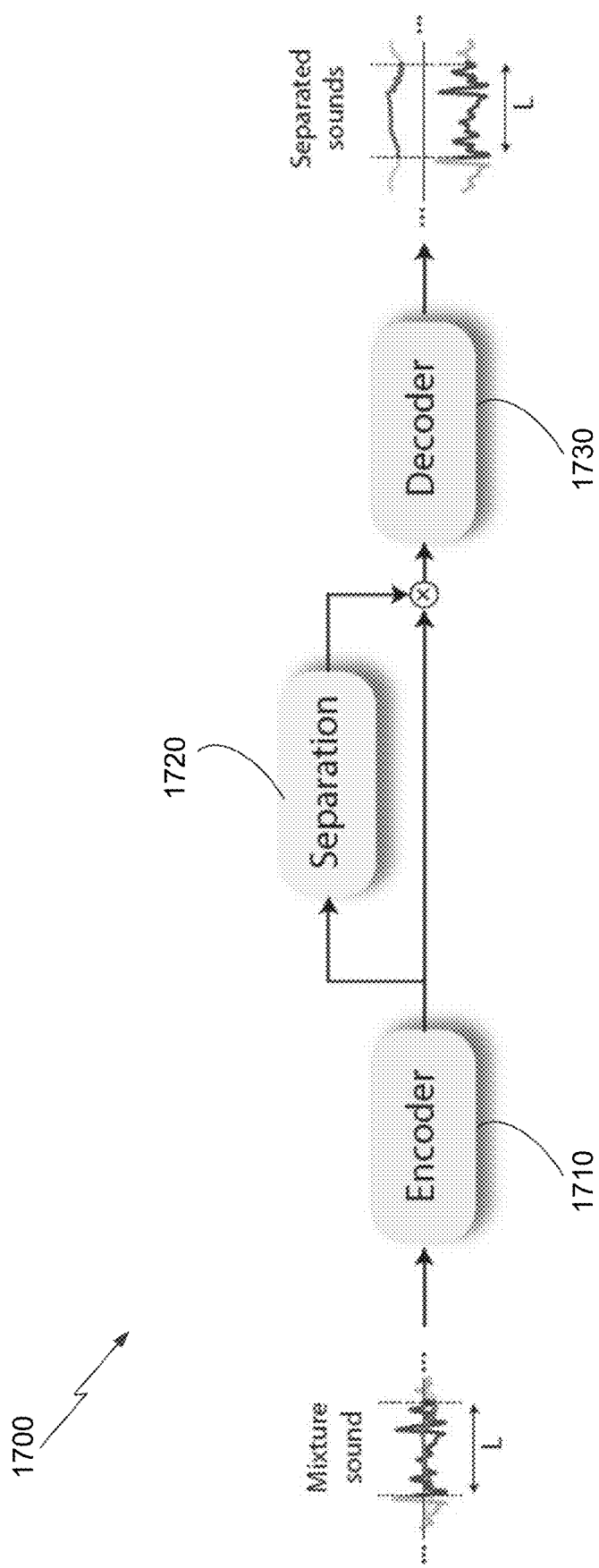
FIG. 17 is a block diagram of an example convolutional TasNet system to separate a combined speech signal.

With reference to FIG. 17, a block diagram of an example convolutional TasNet system 1700 to separate a combined speech signal(s) corresponding to multiple speakers is shown. The fully-convolutional time-domain audio separation network (Conv-TasNet) includes three processing stages, namely, and encoder 1710 (which may be configured to perform some pre-processing, such as dividing the combined signal into separate segments and/or normalize those segments), a separation unit 1720, and a decoder 1730. First, the encoder 1710 is used to transform short segments of the mixture waveform into their corresponding representations in an intermediate feature space. This representation is then used to estimate a multiplicative function (mask) for each source and for each encoder output at each time step. The source waveforms are then reconstructed by transforming the masked encoder features using a linear decoder module (e.g., of the decoder 1730).

More particularly, with further reference to the encoder 1710, the problem of single-channel speech separation can be formulated in terms of estimating C sources $s_1(t), \ldots, s_c(t) \in R^{1 \times T}$, given the discrete waveform of the mixture $x(t) \in R^{1 \times T}$, where $$x(t) = \sum_{i=1}^{c} s_i(t)$$

In time domain audio separation, the aim is to directly estimate $s_i(t)$; $i=1, \ldots, C$, from $x(t)$.

Each segment of the input mixture sound with length L, $x_k \in R^{1 \times N}$ (hereafter x for simplicity) where $k=1, \ldots, T/L$, is transformed into a nonnegative representation, $w \in R^{1 \times N}$ by a 1-D convolution operation (the index k is dropped from now on):

$$w = \text{ReLU}(x * U)$$

where $U \in R^{N \times L}$ contains N vectors (encoder basis functions) with length L each, and * denotes the convolution operation. ReLU denotes the rectified linear unit activation. The decoder 1730 reconstructs the waveform from this representation using a 1-D linear deconvolution operation, which can be defined as a matrix multiplication $\hat{x} = wV$, where $\hat{x} \in R^{1 \times L}$ is the reconstruction of x, and the rows in $V \in R^{N \times L}$ are the decoder basis functions, each with length L. In the case of overlapping encoder outputs, the overlapping reconstructed segments are summed together to generate the final reconstructions.

The separation for each frame is performed by estimating C vectors (masks) $m_i \in R^{1 \times N}$, with $i=1, \ldots, C$, where C is the number of speakers in the mixture that is multiplied by the encoder output w. The mask vectors $m_i$ have the constraint that $$\sum_{i=1}^{C} m_i = 1,$$

where 1 is the unit vector in $R^{1 \times N}$. The representation of each source, $d_i \in R^{1 \times N}$, is then calculated by applying the corresponding mask, $m_i$, to the mixture representation w: $d_i = w \odot m_i$.

The waveform of each source $\hat{s}_i$, $i=1, \ldots, C$ is then reconstructed by the decoder 1730 according to $\hat{s}_i = d_i V$. The unit summation constraint that is imposed on the masks guarantees that the reconstructed sources add up to the reconstructed mixture $$\hat{x} = \sum_{i=1}^{C} \hat{s}_i, \text{ since } \sum_{i=1}^{C} d_i = w \odot \sum_{i=1}^{C} m_i = w.$$

Figure 18A:
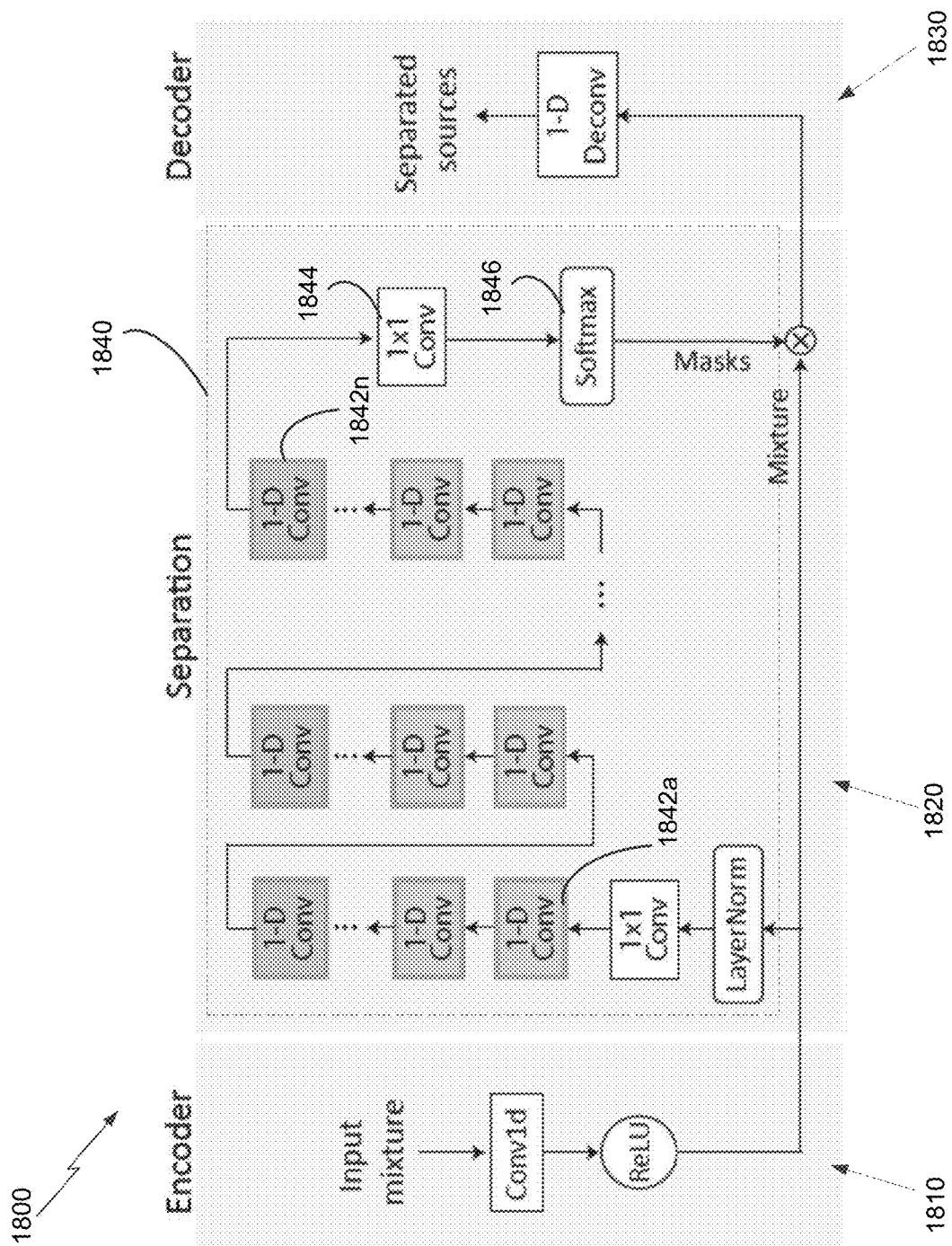
FIG. 18A is a schematic diagram of another example convolutional TasNet system implementation to separate a combined speech signal.
Figure 18B:
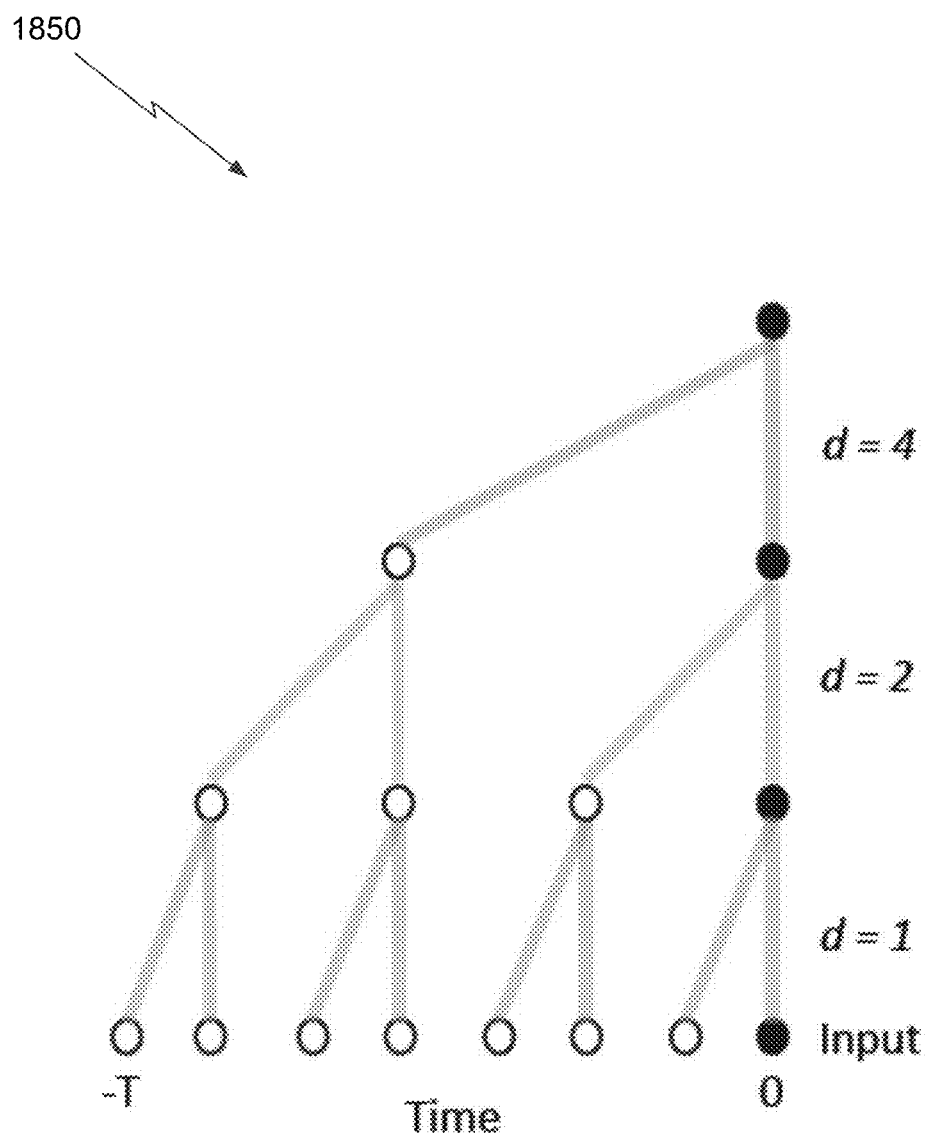
FIG. 18B is a diagram illustrating an example causal dilated convolution implementation.

FIG. 18A is a schematic diagram of another example system implementation 1800, which may be similar to the example system implementation 1700 of FIG. 17, and is configured to separate a combined speech signal (resulting from individual speech signals uttered by multiple speakers). FIG. 18A provides details regarding the configuration and structure of the separation module 1820 (which may be similar to the separation module 1720) implemented as a stacked 1-D dilated convolution blocks 1840 (this stacked 1-D dilated configuration is motivated by the temporal convolutional network (TCN)). TCN was proposed as a replacement for recurrent neural networks (RNNs) for various tasks. Each layer in a TCN contains a 1-D convolution block with increasing dilation factors. The dilation factors increase exponentially to ensure a sufficiently large temporal context window to take advantage of the long-range dependencies of the speech signal, as more particularly shown in FIG. 18B, providing a diagram 1850 illustrating an example of a causal dilated convolution with three kernels of size 2.

In the Conv-TasNet approach, M convolution blocks 1842a-n with dilation factors $1, 2, 4, \ldots, 2^{M-1}$ are repeated R times. The output of the last block in the last repeat is then passed to a 1×1 convolutional layer 1844 with N×C filters followed by a Softmax activation function 1846 to estimate C mask vectors for each of the C target sources. The input to each block may be zero padded to ensure the output length is the same as the input. To further decrease the number of parameters, a depthwise separable convolution (S-conv(•)) is utilized to replace standard convolution in each convolutional block. Depthwise separable convolution (also referred to as separable convolution) has proven effective in image processing and neural machine translation tasks. The depthwise separable convolution operator involves two consecutive operations, a depthwise convolution (D-conv(•)) followed by a standard convolution with kernel size 1 (pointwise convolution, 1×1-conv(•)):

$$D\text{-conv}(Y,K) = \text{concat}(y_j * k_j), j=1, \ldots, N$$

$$S\text{-conv}(Y,K,L) = D\text{-conv}(Y,K) * L \quad (7)$$

where $Y \in R^{G \times M}$ is the input to the S-conv(•), $K \in R^{G \times P}$ is the convolution kernel with size P, $y_j \in R^{1 \times M}$ and $k_j \in R^{1 \times P}$ are the rows of matrices Y and K, respectively, and $L \in R^{G \times H \times 1}$ is the convolution kernel with size 1. In other words, the D-conv(•) operation convolves each row of the input Y with the corresponding row of matrix K, and 1×1-conv(•) is the same as a fully connected linear layer that maps the channel features to a transformed feature space. In comparison with the standard convolution with kernel size $\hat{K} \in R^{G \times H \times P}$, depthwise separable convolution only contains G×P+G×H parameters, which decreases the model size by a factor of $$\frac{H \times P}{H + P}.$$

Figure 19:
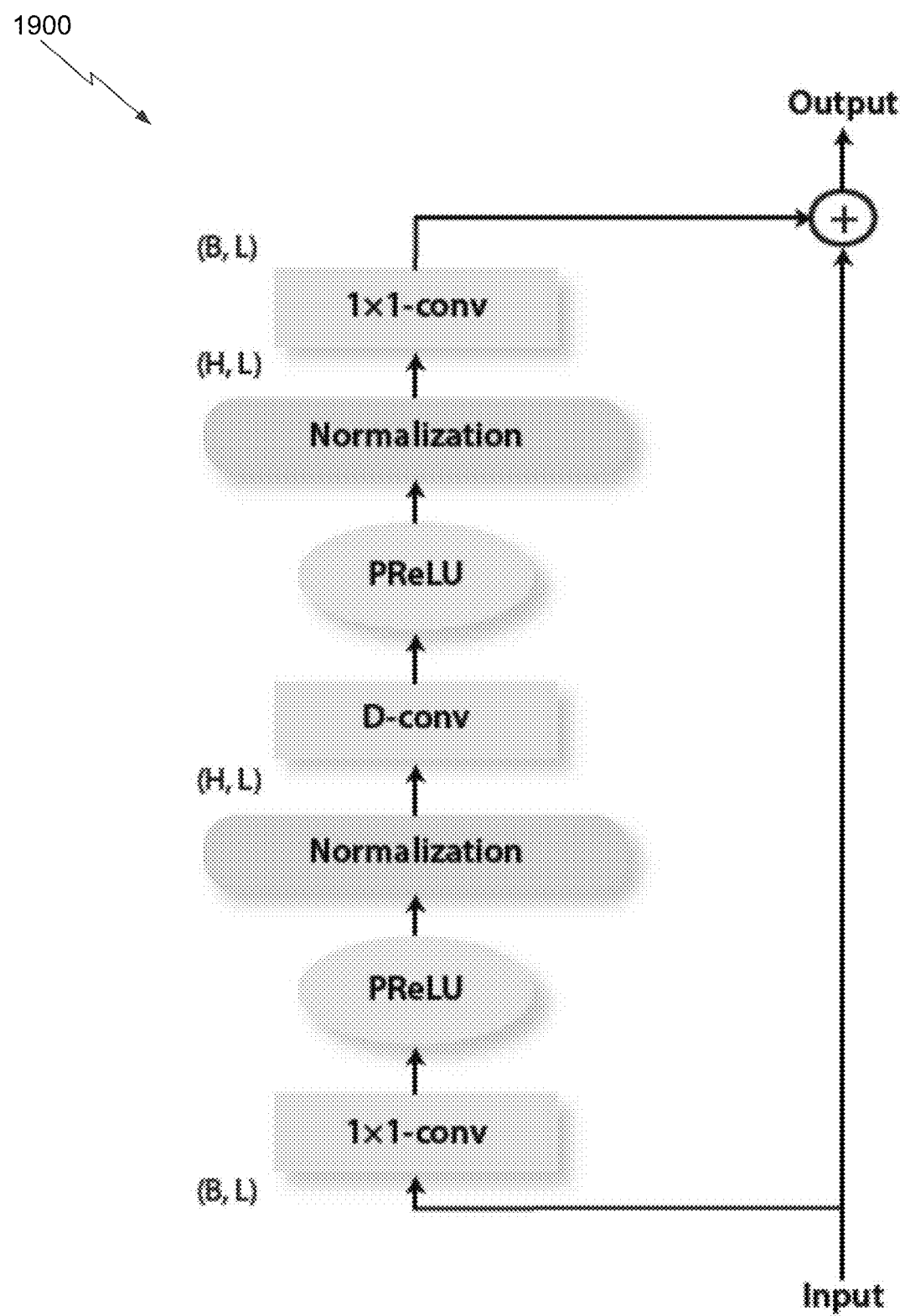
FIG. 19 is a flow diagram of operations performed by each 1-D convolutional block of the system of FIG. 18A.

With reference to FIG. 19, a flow diagram 1900 of operations performed by each 1-D convolutional block is shown. In each 1-D convolutional block, a 1×1-conv operation is followed by a S-conv operation. A nonlinear activation function and a normalization are added after both the first 1×1-conv and D-conv operations. The nonlinear activation function is the parametric rectified linear unit (PReLU), namely:

$$PReLU(x) = \begin{cases} x, & x \geq 0 \\ \alpha x, & \text{otherwise} \end{cases}$$

where α∈R is a trainable scalar controlling the negative slope of the rectifier. An identity residual connection is added between the input and output of each convolutional block. At the beginning of the separation module, a linear 1×1conv block is added as a bottleneck layer. This block determines the number of channels in the input and output of the subsequent convolutional blocks. For instance, if the linear bottleneck layer has B channels, then for a convolutional block with H channels and kernel size P, the size of the kernel in the first 1×1-conv block, the first D-conv block and the last 1×1-conv block should be $O \in R^{B \times H \times 1}$, $K \in R^{H \times P}$, and $L \in R^{H \times B \times 1}$, respectively.

The choice of the normalization technique used in conjunction with the convolutional-TasNet speech separation technique can significantly impacts the performance. Three different normalization schemes may be used, namely: channel-wise layer normalization (cLN), global layer normalization (gLN), and batch normalization (BN). Channel-wise layer normalization (cLN) is similar to the standard layer normalization operation in sequence modeling which is applied to each segment k independently:

$$cLN(y_k) = \frac{y_k - E|y_k|}{\sqrt{\text{Var}(y_k) + \epsilon}} \odot \gamma + \beta$$

$$E|y_k| = \frac{1}{N} \sum_N y_k$$

$$\text{Var}(y_k) = \frac{1}{N} \sum_N (y_k - E|y_k|)^2$$

where $y_k \in R^{N \times 1}$ is the $k^{th}$ segment of the sequence Y, and γ, $\beta \in R^{N \times 1}$ are trainable parameters. To ensure that the separation module is invariant to change in the scale of the input, cLN may be always applied to the input of the separation module (i.e., to the encoder output w): ŵ=cLN(w). In the 1-D convolutional blocks, cLN is suitable for both the causal and noncausal configurations.

In global layer normalization (gLN), each feature is normalized over both the channel and the time dimension:

$$gLN(Y) = \frac{Y - E|Y|}{\sqrt{\text{Var}(Y) + \epsilon}} \odot \gamma + \beta$$

$$E|Y| = \frac{1}{NT} \sum_{NT} Y$$

$$\text{Var}(Y) = \frac{1}{NT} \sum_{NT} (Y - E|Y|)^2$$

where γ, $\beta \in R^{N \times 1}$ are trainable parameters. Although the normalization is performed globally, the rescaling and re-centering by γ and β are performed independently for each time step. Because gLN uses the information from the entire utterance, it can only be used for noncausal implementation. Batch normalization (BN) can also be applied along the time dimension. It is to be noted that the calculation of mean and variance during the training phase requires the entire utterance (i.e. noncausal), but during testing, BN can be used in both the causal and noncausal implementations since the mean and the variance are calculated during the training phase and are subsequently fixed during the test.

Figure 20:
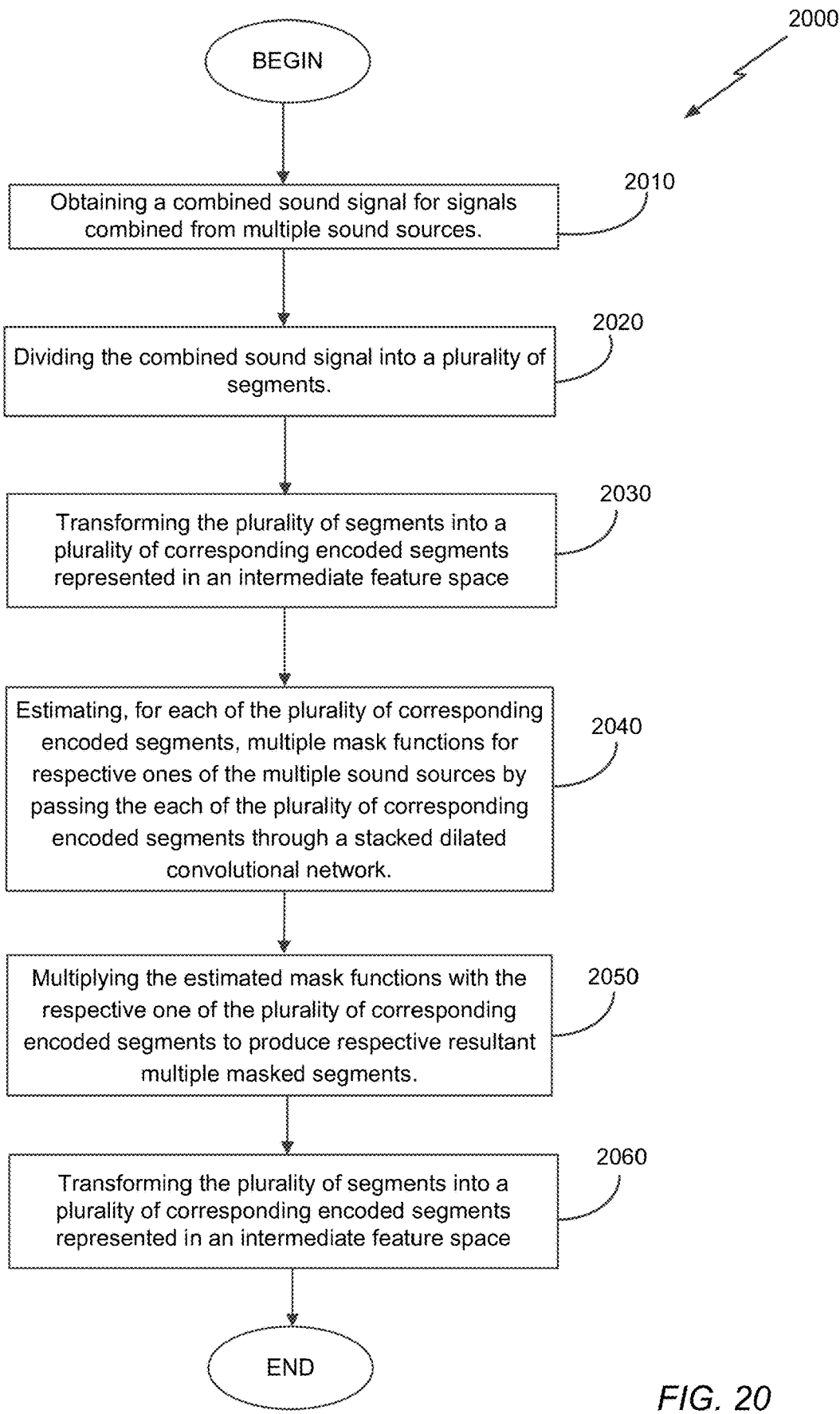
FIG. 20 is a flowchart of an example procedure to separate speech signals.

With reference next to FIG. 20, a flowchart of an example procedure 2000 to separate speech signals is shown. As noted, the procedure 2000 may be included as part of the procedure 300 to facilitate attentional selection based on neural signals measured for a user (e.g., the procedure 2000 may be implemented as the speech separation processing performed, for example, at the block 320 of the procedure 300), and may also be used for other types of applications such as virtual and augmented reality applications, surveillance applications, and so on.

The procedure 2000 includes obtaining 2010 a combined sound signal for signals combined from multiple sound sources. It should be noted that when used in conjunction with the procedure 300, the operation 2010, as well as other operations of the procedure 2000, may not need to be performed (i.e., the obtaining of the combined sound signal will generally have already been performed by an earlier operation of the procedure 300, and therefore would not have to be repeated by the procedure 2000). The procedure 2000 additionally includes dividing 2020 the combined sound signal into a plurality of segments, and transforming 2030 the plurality of segments into a plurality of corresponding encoded segments represented in an intermediate feature space (e.g., by the encoder 1710 of FIG. 17).

As further depicted in FIG. 20, the procedure 2000 further includes estimating 2040, for each of the plurality of corresponding encoded segments, multiple mask functions for respective ones of the multiple sound sources by passing the each of the plurality of corresponding encoded segments through a stacked dilated convolutional network. The estimating may be performed, for example, by the stacked dilated convolutional network 1840 of FIG. 18A. In some embodiments, estimating the multiple mask function may include performing, at each block of the stacked dilated convolution network, a 1×1 convolution operation followed by a depthwise separable convolution operation (S-conv). In such embodiments, the procedure 2000 may additionally include performing another 1×1 convolution operation, at the each block of the stacked dilated convolutional network, following the S-conv operation, with a non-linear activation function (PReLU) and a normalization process added between each two convolution operations in the each block of the stacked dilated convolutional network.

With continued reference to FIG. 20, the procedure 2000 also includes multiplying 2050 the estimated mask functions with the respective one of the plurality of corresponding encoded segments to produce respective resultant multiple masked segments, and generating 2060 separated estimates of the signals from the multiple sound sources based on the respective resultant multiple masked segments.

Testing and evaluations were performed for some of the implementations described herein for the Conv-TasNet approach. An example system implementation was evaluated for a two-speaker speech separation problem using the WSJ0-2mix and WSJ0-3mix datasets. Thirty hours of training and 10 hours of validation data were generated from speakers in si_tr_s from the datasets. The speech mixtures were generated by randomly selecting utterances from different speakers in the Wall Street Journal dataset (WSJ0) and mixing them at random signal-to-noise ratios (SNR) between −2.5 dB and 2.5 dB. A five-hour evaluation set was generated in the same way using utterances from 16 unseen speakers in si_dt_05 and si_et_05. All the waveforms were resampled at 8 kHz.

The networks were trained for 100 epochs on 4-second long segments. The initial learning rate was set to $1e^{-2}$ or $1e^{-3}$, depending on the model configuration, and is halved if the accuracy of validation set is not improved in 3 consecutive epochs. The stochastic optimization "Adam" was used as the optimization process. A 50% stride size was used in the convolutional autoencoder (i.e. 50% overlap between consecutive frames). The hyperparameters of the network are shown in Table 5 below.

TABLE 5

| Symbol | Description |
| --- | --- |
| N | Number of filters in autoencoder |
| L | Length of the filters (in samples) |
| B | Number of channels in bottleneck 1 × 1-conv block |
| H | Number of channels in convolutional blocks |
| P | Kernel size in convolutional blocks |
| X | Number of convolutional blocks in each repeat |
| R | Number of repeats |

Figure 21:
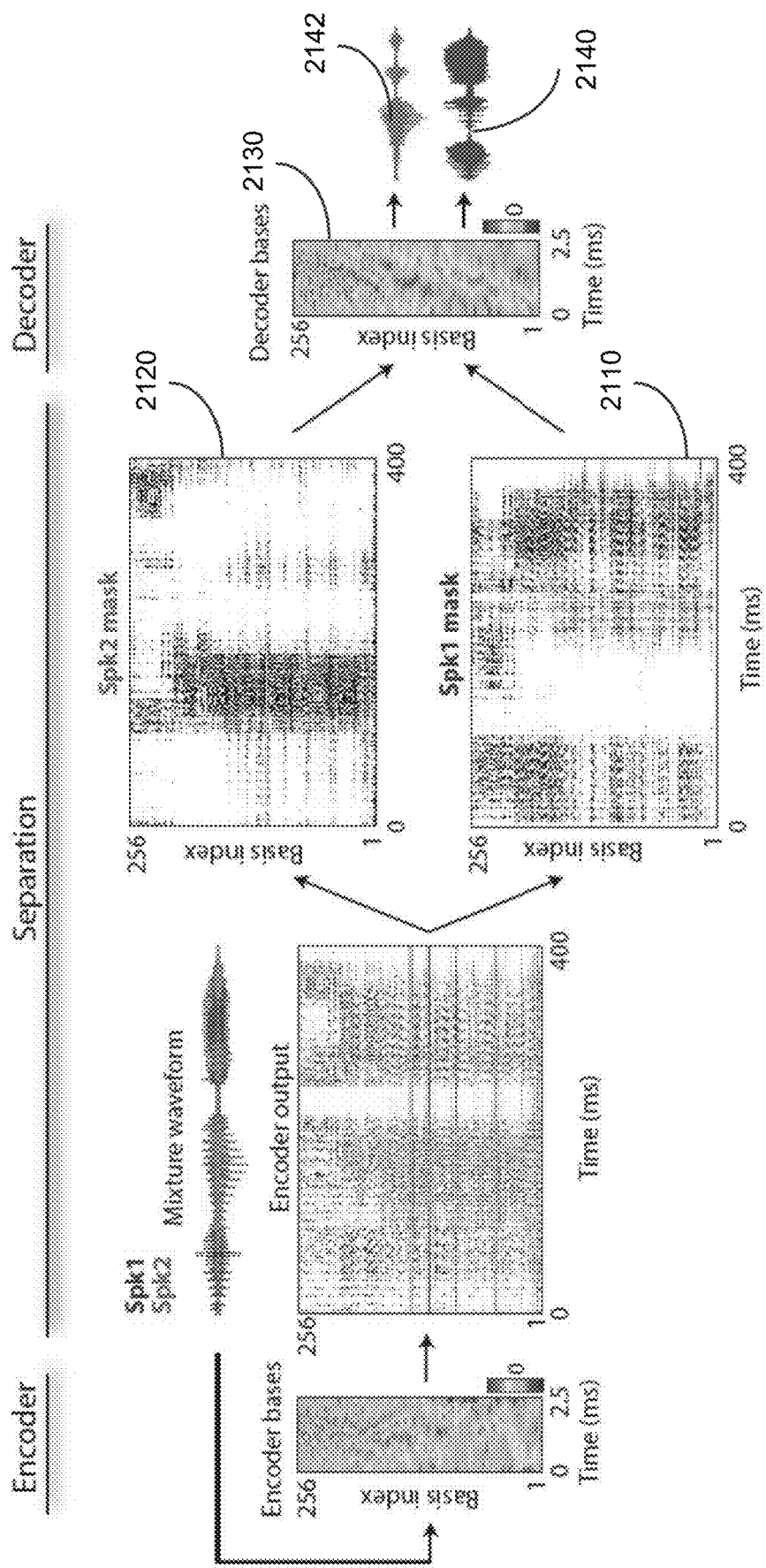
FIG. 21 is a diagram visualizing the encoder and decoder basis functions, encoder representation, and source masks for a sample 2-speaker mixture.

FIG. 21 visualizes the internal variables of the Conv-TasNet implementation for one example mixture sound with two overlapping speakers. The encoder and decoder basis functions were sorted based on the Euclidian similarity, which was found using an unsupervised clustering procedure. The basis functions show a diversity of frequency and phase tuning. The representation of the encoder is shaded according to the power of each speaker at the corresponding basis output at each time point, demonstrating the sparsity of the encoder representation. As can be seen in FIG. 21, the estimated masks, 2110 and 2120 for each of the two speakers highly resemble their encoder representations, which allows for the suppression of the encoder outputs that correspond to the interfering speaker and the extraction of the target speaker in each mask. The separated waveforms for the two speakers were estimated by the linear decoder, whose basis functions 2130 are also depicted in FIG. 21. The separated waveforms are shown as waveforms 2140 and 2142.

Figure 22:
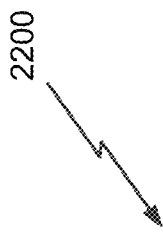
FIG. 22 includes a table providing data representative of the effect of different configurations on the performance of a Conv-TasNet implementation.

The performance of Conv-TasNet was first evaluated on two speaker separation tasks as a function of different network parameters. FIG. 22 includes a table 2200 providing data representative of the effect of different configurations (controlled using the parameters of Table 5 above) on the performance of the Conv-TasNet implementation. The results captured by the table 2200 of FIG. 22 lead to the following observations.

(i) With the same configuration of the autoencoder and the channels in the linear 1×1-conv bottleneck layer B, more channels in the convolutional blocks H leads to better performance, indicating the importance of a separation module with sufficient computational capacity.

(ii) With the same configuration of the autoencoder and the convolutional blocks, more channels in the linear 1×1-conv bottleneck layer B leads to better performance, confirming again the notion that the separation module should have high modeling capacity.

(iii) With the same configuration of the separation module, more filters in the autoencoder N leads to minor improvement. This result suggests an upper bound for the utility of an overcomplete encoder representation, beyond which the separation does not improve.

(iv) With the same configuration of the autoencoder and channels in the separation module (B and H), a larger temporal receptive field leads to better performance, emphasizing the importance of long-range temporal dependencies of speech for separation.

(v) With the same configuration of the autoencoder, channels in the separation module (B and H) and size of the receptive field, more convolutional blocks leads to better performance. This result suggests that stacking more convolutional blocks with smaller dilation factors is superior to fewer blocks with larger dilation factors having the same receptive field size.

(vi) With the same number of filters N and separation module configuration, a smaller filter length L leads to better performance. Note that the best Conv-TasNet system uses a filter length of 2.5 ms ($L/f_s=20/8000=0.0025$ s), which makes it more difficult to train an LSTM separation module with the same L due to the large number of time steps in the encoder output.

(vii) With the same configuration of the entire network except for the type of normalization in the convolutional blocks, gLN has the best performance in the noncausal implementation, while BN has the best performance in the causal implementation. This result shows the importance of the normalization scheme and the difference between the causal and noncausal implementations.

Figure 23:
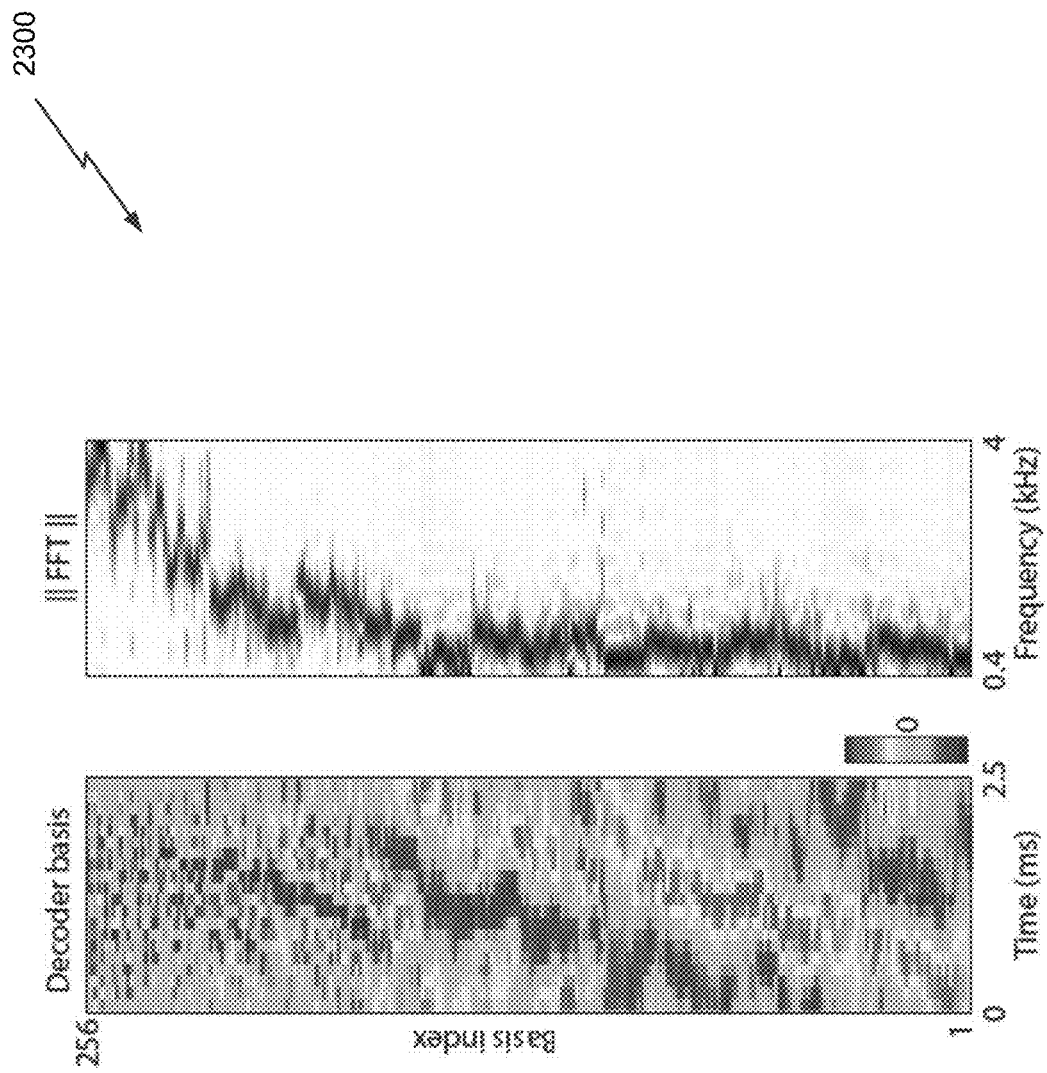
FIG. 23 is a graphical representation of example basis functions of a linear decoder and the magnitudes of their FFTs.

One of the motivations for replacing the STFT representation of the mixture signal with the convolutional encoder in TasNet was to construct a representation of the audio that is optimized for speech separation. To shed light on the properties of the encoder representation, the basis functions of the decoder were examined, as they form a linear transform back to the sound waveform. A graphical representation of the basis functions is shown in FIG. 23 for a causal Conv-TasNet (L=2:5 ms), sorted by the similarity of the Euclidian distance of the basis functions. The magnitudes of the FFTs for each filter are also shown in the same order. As seen in the figure, the majority of the filters are tuned to lower frequencies. In addition, FIG. 23 shows that filters with the same frequency tuning express all possible phase values for that frequency. This result suggests an important role for low frequency features of speech such as pitch as well as explicit encoding of the phase information to achieve superior speech separation performance.

Thus, discussed herein is a fully-convolutional time-domain audio separation network (Conv-TasNet). TasNet is proposed to address the shortcomings of some separation procedure that rely on STFT-based representation, namely the decoupling of phase and magnitude, the suboptimal representation of the mixture audio for separation, and the high minimum latency of some STFT-based speech separation systems. This improvement is accomplished by replacing the STFT with a convolutional autoencoder. The separation is done using a temporal convolutional network (TCN) architecture together with a depthwise separable convolution operation. The evaluations performed showed that Conv-TasNet can outperform STFT speech separation systems even when the ideal time-frequency mask for the target speakers is used. In addition, TasNet has a smaller model size and a shorter minimum latency, which makes it suitable for low-resource, low latency applications. Unlike STFT, which has a well-defined inverse transform that can perfectly reconstruct the input, a convolutional autoencoder does not guarantee that the input can be perfectly reconstructed. The main reason is that the convolution and deconvolution operations of the autoencoder are not required to be exact inverse operations, unlike STFT and iSTFT operations. In addition, the ReLU nonlinearity of the encoder further prevents or inhibits it from achieving perfect reconstruction. This rectification is necessary, however, for imposing a nonnegativity constraint on the encoder output, which is crucial for estimating the separation masks. If no constraint is imposed, the encoder output could be unbounded in which case a bounded mask cannot be properly defined. On the other hand, the ReLU activation used in the encoder implicitly enforces sparsity on the encoder output. Therefore, a larger number of basis functions is required to achieve an acceptable reconstruction accuracy compared with the linear STFT operation. This approach resembles an overcomplete dictionary in a sparse coding framework where each dictionary entry corresponds to a row in the decoder matrix V. The analysis of the encoder-decoder basis functions in revealed several interesting properties. One, most of the filters are tuned to low acoustic frequencies (more than 60% tuned to frequencies below 1 kHz). This pattern of frequency roughly resembles the well-known mel frequency scale as well as the tonotopic organization of the frequencies in the mammalian auditory system. In addition, the overexpression of lower frequencies may indicate the importance of accurate pitch tracking in speech separation, similar to what has been reported in human multitalker perception studies. In addition, it was found that filters with the same frequency tuning explicitly express all the possible phase variations. In contrast, this information is implicit in the STFT operations, where the real and imaginary parts only represent symmetric (cosine) and asymmetric (sine) phases, respectively. This explicit encoding of signal phase values may be the key reason for the strong performance of TasNet.

The combination of high accuracy, short latency, and small model size makes Conv-TasNet a suitable choice for both offline and real-time, low-latency speech processing applications such as embedded systems and wearable hearing and telecommunication devices. Conv-TasNet can also serve as a front-end module for tandem systems in other audio processing tasks, such as multitalker speech recognition and speaker identification.

Speaker Independent Speech Separation Using Online Deep Attractor Networks (ODAN)

Yet another speech separation that may be employed (e.g., to facilitate attentional selection processing, or for other objective of purpose) is a speaker independent speech separation using online deep attractor networks (ODAN). ODAN-based processing is configured to automatically separate speakers in mixed audio without any need for prior training on the speakers. The separated speakers are compared to evoked neural responses in the auditory cortex of the listener to determine and amplify the attended speaker. Testing and evaluation results for some of ODAN-based implementations show that auditory attention decoding with automatically separated speakers is as accurate and fast as using clean speech sounds. Moreover, the proposed implementations significantly improves both the subjective and objective quality of the attended speaker. By combining the latest advances in speech processing technologies and brain-computer interfaces, a major obstacle in actualization of auditory attention decoding is addressed that can assist individuals with hearing impairment and reduce the listening effort for normal hearing subjects in adverse acoustic environments.

Thus, in some of the implementations described herein, a causal, speaker-independent automatic speech separation approach is proposed that can be generalized to unseen speakers, meaning that the separation of speakers can be performed without any prior training on target speakers. As discussed earlier, one approach to speech separation is based on deep attractor networks (DAN, also discussed herein with respect to FIGS. 10-13), which performs source separation by projecting the time-frequency (spectrogram) representation of a mixed audio signal into a high-dimensional space in which the representation of the speakers becomes more separable. Compared to some alternative speaker independent approaches, DAN is advantageous in that it preforms an end-to-end separation, meaning the entire process of speaker separation is learned together. However, in some situations, DAN-based implementations perform noncausal speech separation, meaning that the procedures require an entire utterance to perform the separation. In real-time applications, such as in a hearing device, a causal, low-latency procedure is desirable to prevent or inhibit perceivable distortion of the signal. Thus, in some embodiments, the problem of speaker-independent AAD may be handled without clean sources by using an online implementation of DAN (online deep attractor network, ODAN) to automatically separate unseen sources. The proposed AAD framework enhances the subjective and objective quality of perceiving the attended speaker in a multitalker mixture.

Figure 24:
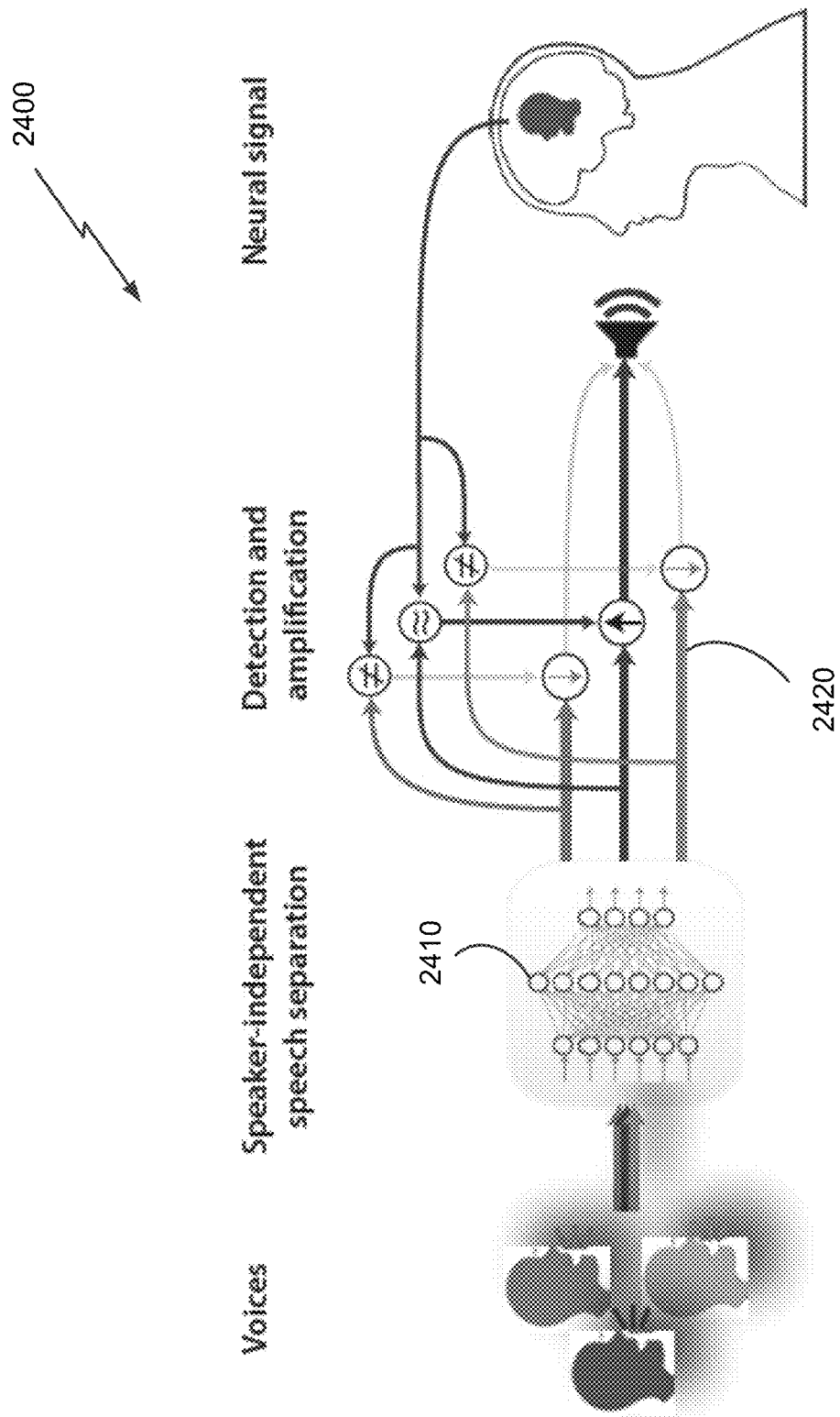
FIG. 24 is a schematic diagram of another example platform to process (e.g., separate) combined sound signals for attentional selection applications.

For ease of reference, FIG. 24 is a schematic diagram of another example platform 2400 to process (e.g., separate) combined sound signals for attentional selection applications. The platform includes a speaker-independent speech separation stage 2410, followed by a detection and amplification stage 2420 that enhances (including, in some embodiments, reconstructing) one or more separated signals based on detected neural signals observed or measured from an individual. As shown in FIG. 24, a speaker separation procedure (implemented in the speech separation stage 2410) first separates speakers in multitalker mixed audio. Next, the spectrograms of separated speakers are compared to the spectrogram that is reconstructed from evoked neural responses in the auditory cortex of the listener to determine the attended speaker. Then, the attended speaker is amplified relative to other speakers in the mixture before it is delivered to the listener. Each of the processing stages depicted in FIG. 24 will be discussed in greater detail below.

The problem of speech separation is formulated as estimating C sources, $s_1(t), \ldots, s_c(t) \in R^{1 \times T}$ from the mixture waveform $x(t) \in R^{1 \times T}$:

$$x(t) = \sum_{i=1}^{C} s_i(t)$$

Taking the short-time Fourier transform (STFT) of both sides formulates the source separation problem in the time-frequency (T-F) domain where the complex mixture spectrogram is the sum of the complex source spectrograms:

$$X(f, t) = \sum_{i=1}^{C} S_i(f, t)$$

where $X(f,t)$ and $S_i(f,t) \in C^{F \times T}$. One common approach for recovering the individual sources, $S_i$, is to estimate a real-valued time-frequency mask for each source, $M_i \in R^{F \times T}$ such that $$|\hat{S}_i(f,t)| = |X(f,t)| M_i(f,t)$$

The waveforms of the separated sources are then approximated using the inverse STFT of $|\hat{S}_i(f,t)|$ using the phase of the mixture audio:

$$\hat{s}_i(t) = \text{IFFT}(|\hat{S}_{i(f,t)}| \angle X(f,t))$$

The mask for each source needs to be estimated directly from the mixture spectrogram:

$$M_i = H(|X(f,t)|; \theta|)$$

where $H(\cdot)$ is the separation model defined by parameter $\theta$.

Figure 25A:
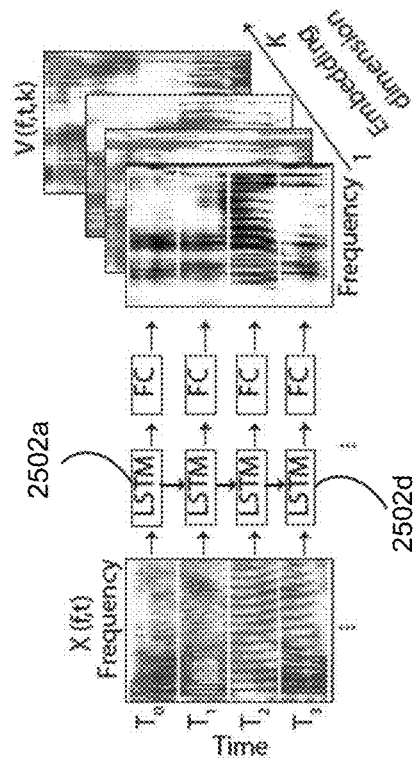
FIG. 25A is a diagram illustrating the projection of a time-frequency signal representation into an embedding space of time-frequency bins.

In some real-world scenarios, the identity of speakers in a mixture is unknown in advance. Therefore, training separation models using data from target speakers is not possible in such situations. DAN, for example, aims to directly maximize the reconstruction accuracy of the sources, therefore allowing for end-to-end training of the model. Here, an online extension of DAN, ODAN, is proposed that can be implemented in real time. In this framework, source separation is performed by first projecting the mixture spectrogram onto a high-dimensional space where T-F bins belonging to the same source are placed closer together to facilitate their assignment to the corresponding sources. This procedure is performed in multiple steps. First, the mixture magnitude spectrogram, |X(f,t)|, is projected onto a tensor, V(f,t,k), where each time-frequency bin is represented by a vector of length K (as shown in FIG. 25A, showing a high-dimensional embedding of the time-frequency bins):

$$V(f,t,k)=H(|X(f,t)|;\theta)$$

where the separation model, H(•), is implemented, in some examples, using a deep neural network with parameters $\theta$. This representation is referred to as the embedding space. The neural network that embeds the spectrogram includes of four stacked long short-term memory (LSTM) layers 2502*a-d* followed by a fully connected network.

In an example implementation, the four unidirectional LSTM layers included 600 units in each layer. The embedding dimension was set to 20 based on the observations reported in, which results in a fully connected layer of 2580 hidden units (20 embedding dimensions times 129 frequency channels) after the LSTM layers. The number of anchors was set, for the example implementation, to 6. The models were trained using curriculum training in which the models were first trained on 100-frame-long input segments (0.8 seconds) and continued to be trained thereafter on 400-frame input segments (3.2 seconds). The batch size was set to 128, and the "Adam" process was used as the optimizer with an initial learning rate of $1e^{-4}$, which is halved if validation error does not decrease after 3 epochs. The total number of epochs was set to 150, and early stopping was applied if validation error did not decreased after 10 consecutive epochs. All models were initialized using a pretrained LSTM-DAN model. A gradient clip with a maximum norm of 0.5 was applied to accelerate training. The neural network models used in the example implementation that was tested and evaluated were trained by mixing speech utterances from the Wall Street Journal corpus, specifically the WSJ0-2mix and WSJ0-3mix datasets, which contain 30 hours of training, 10 hours of validation, and 5 hours of test data. The test set contained 3000 mixtures generated by combining utterances from 16 unseen speakers from the si_dt_05 and si_et_05 subsets. All sounds were resampled to 8 KHz to simplify the models and reduce computational costs. The input feature was the log magnitude spectrogram computed using a STFT with 32-ms window length (256 samples), 8-ms hop size (64 samples), and weighted by the square root of a hamming window. Wiener-filter-like masks (WFM) were used as the training objective.

Figure 25B:
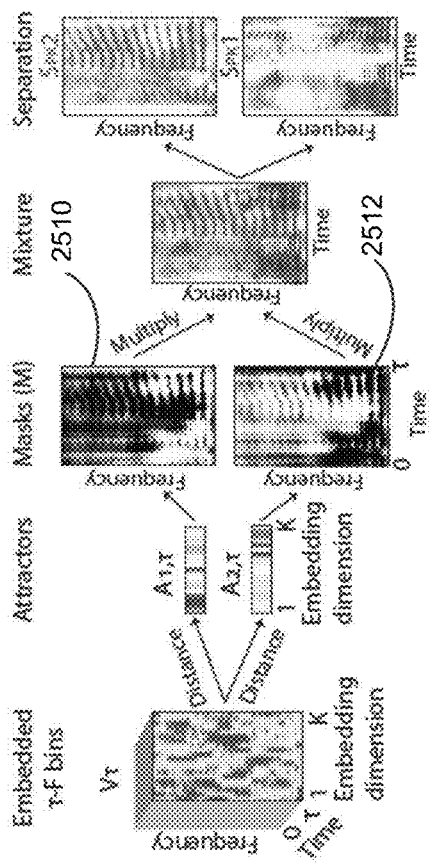
FIG. 25B is a diagram depicting a process of estimating time-frequency masks and separating speakers.

To assign each embedded T-F bin to one of the speakers in the mixture, the centroid of the speakers is tracked in the embedding space. The centroids of a source i and at time step $\tau$ are referred to as the attractor points, $A_{\tau,i}(k)$, because they pull together and attract all the embedded T-F bins that belong to the same source. Therefore, the distance (defined as the dot product) between the embedded T-F bins to each of the attractor points determines the source assignment for that T-F bin, which is then used to construct a mask (e.g., masks 2510 and 2512 in FIG. 25B, which depicts a process of estimating the time-frequency masks and separating speakers) to recover that source.

$$M_{\tau,i}(f)=\text{Softmax}(A_{\tau,i}(k)V_\tau(f,k))$$

The Softmax function. In the above relationship, is defined as:

$$\text{Soft max}(x_i) = \frac{e^{x_i}}{\sum_{i=1}^{C} e^{x_i}}$$

The masks subsequently multiply the mixture magnitude spectrogram to estimate the magnitude spectrograms of each source. All the parameters of the ODAN are found jointly during the training phase by maximizing the source reconstruction accuracy, l:

$$l=\Sigma_{f,t,i}|||S_i(f,t)-|X(f,t)|M_i(f,t)|||_2^2$$

Figure 25C:
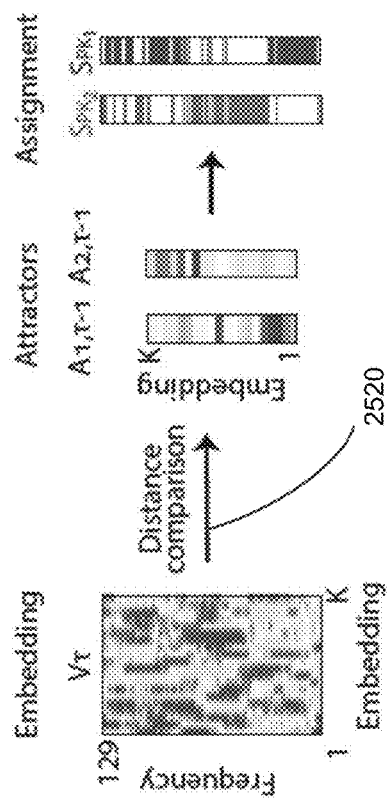
FIG. 25C is a diagram depicting a process to perform speaker assignment for a current frame of speech data at a time step τ.

The initial location of attractor points in the embedding space (at $\tau=0$) is chosen from a fixed, pretrained set of points in the embedding space (methods). Updating the attractor points in each time step is performed using a one-step generalized expectation maximization (EM) algorithm. At time step $\tau$, the source assignment vectors for each speaker, $Y_{\tau,i}(f)$, are computed from the embedded frequency channels $V_\tau(f, k)$ by comparing (see operation 2520 of FIG. 25C, which shows speaker assignment for each frequency at time step $\tau$) the distance of each embedded T-F bin to each attractor from the previous time step $A_{\tau-1}(k)$ according to:

$$Y_{\tau,i}(i)=\text{Softmax}(A_{\tau-1}(i,k)V_{\tau,i}(k))$$

A Softmax function is applied to enhance the source assignment contrast.

Figure 25D:
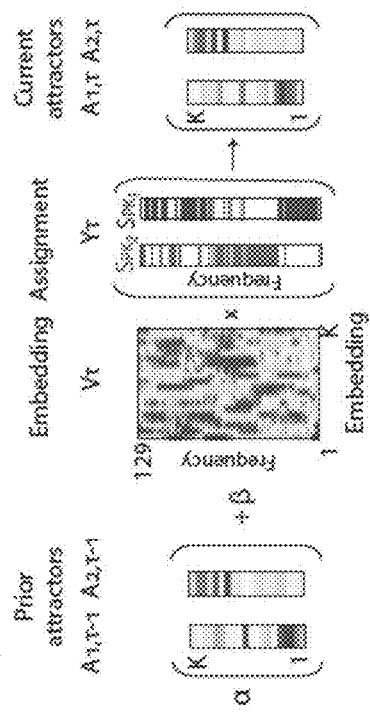
FIG. 25D is a diagram depicting a process to update locations of attractors at the time step τ.

Next, the location of the attractors is updated based on the centroid of the current frame, the previous location of the attractors, and the current input (as illustrated in FIG. 25D, showing the updating of the locations of attractors at time step $\tau$). Particularly, the location of the attractors at each time step is updated based on their previous position, the centroid of the embeddings for the current frame, and the current input frame, according to:

$$A_{\tau,i}(k) = (1-\alpha_\tau)A_{\tau-1,i}(k) + \alpha\tau C_{\tau,i}(k)$$

$$C_{\tau,i}(k) = \frac{V_\tau(f,k)Y_{\tau,i}(f)}{\Sigma_f Y_{\tau,i}(f)}$$

where $C_{\tau,i}(k)$ is the centroid of the embeddings of source i at time step $\tau$, and parameter $\alpha$ determines the rate of the update at time $\tau$ by controlling the tradeoff between the previous location of the attractors and the centroid of the sources in the current frame. If $\alpha$ is too small, the attractor changes position too quickly from one frame to the next, which may result in a noisy estimate and unstable separation. If $\alpha$ is too large, the attractor will be too slow to track the changes in the mixture condition, which could be problematic if the speakers in the mixture change over time.

To optimally estimate $\alpha$, a dynamic weighting function is computed to control the relative weight of previous and current estimates using two parameters, f and g, for each source i at time step $\tau$, according to:

$$f_{\tau,i}=\sigma(h_{\tau-1}W_f+X_\tau(f)U_f+A_{\tau-1,i}(k)J_f+b_f)$$

$$g_{\tau,i}=\sigma(h_{\tau-1}W_g+X_\tau(f)U_g+A_{\tau-1,i}(k)J_g+b_g)$$

where σ(•) is the sigmoid activation function; $h_{\tau-1}$ is the previous output of the last LSTM layer; $X_\tau$ is the current mixture feature; and W, U, J, and b are parameters that are jointly learned during the training of the network. Given f and g, the update parameter α is estimated using the following equation:

$$\alpha_{\tau,i} = \frac{(g_{\tau,i}\Sigma_f Y_{\tau,i}(f))}{\left(f_{\tau,i}\sum_{t=0}^{\tau-1}\Sigma_f Y_{\tau,i}(f) + g_{\tau,i}\Sigma_f Y_{\tau,i}(f)\right)}$$

where f determines the contribution of previous attractor estimates, and g determines the contribution of the current frame. Once the attractors for the current frame are updated, the masks for separating the current frame are derived using the similarity of T-F embeddings and each attractor.

Figure 26:
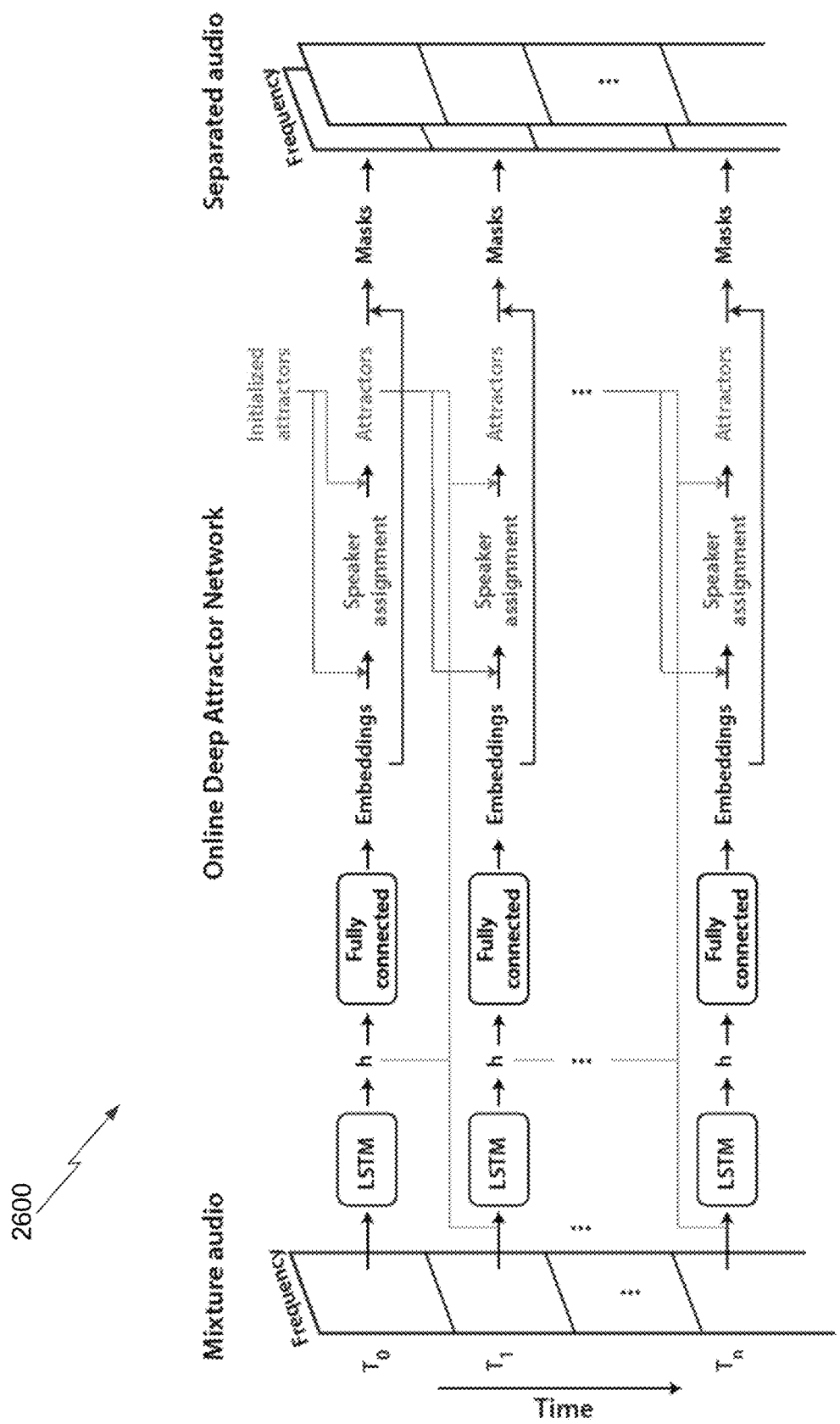
FIG. 26 is a schematic diagram showing implementation of the Online Deep Attractor Network (ODAN) process.

FIG. 26 is a schematic diagram 2600 showing implementation of the ODAN process. As shown, at each time step, the mixture spectrogram is projected into an embedding space in which the separation of the speakers is performed. The attractor points from the previous time step are used to first assign each embedding point of the current frame to a speaker to accomplish this goal. Next, the assignments are used to update the location of the attractor points. The distance of the embedded points to the new attractors is used to create a time-frequency mask for each of the speakers in the mixture, which multiplies the mixture spectrogram to extract the speakers.

Figure 27A:
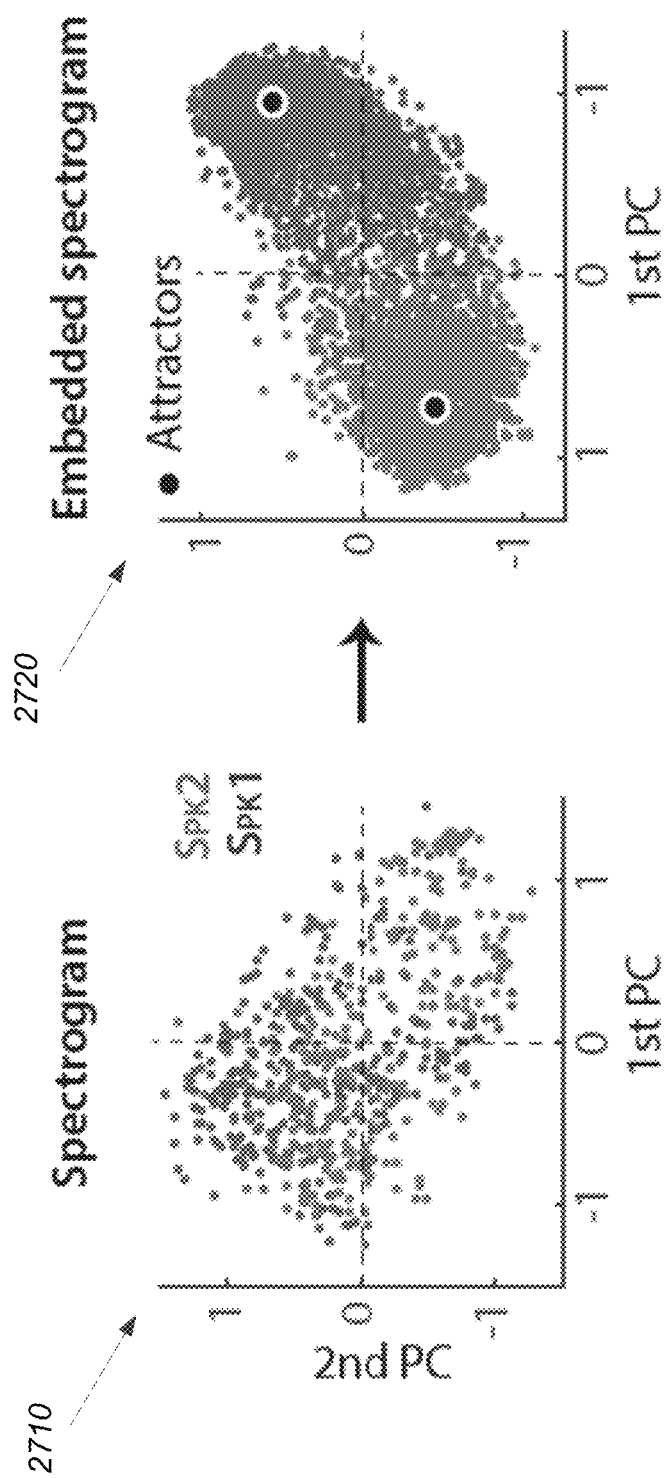
FIG. 27A are spectrograms providing visual representations of the improved separation in the embedding space relative to the initial time-frequency space.

As discussed herein, an ODAN-based implementation projects T-F bins into a high-dimensional embedding space that is optimal for source separation, meaning that T-F bins belonging to the same source should be placed closer to each other in the embedding space. To confirm that this situation is the case, the representation of two speakers were projected in both the spectrogram domain and embedding domain onto a 2-D space using principal component analysis to allow visualization. This improved separability of speakers is shown in FIG. 27A, where the representations are visualized using the first two principal components of the spectrogram (in graph 2710) and the embedding space (in graph 2720). The improved separation in the embedding space is evident from the decreased overlap in the embedding space. Each dot represents one T-F bin (in the left graph 2710) or one embedded T-F bin (the right graph 2720).

The ODAN model was evaluated on a single-channel, two-speaker and three-speaker separation tasks. The WSJ0-2mix and WSJ0-3mix dataset generated from the Wall Street Journal (WSJ0) dataset was used because it is commonly used for comparison with state-of-the-art speaker separation systems. This dataset contains 30 hours of training data, 10 hours of validation data, and 5 hours of test data. The mixed sounds were generated by randomly selecting utterances from different speakers in the WSJ0 training set and mixing them at various signal-to-noise ratios (SNR), randomly chosen between −2.5 dB and 2.5 dB. Tables 2810 and 2820 provided in FIG. 28 show the comparison of the ODAN method with other speaker-independent speech separation methods on 2-speaker and 3-speaker mixtures. The evaluation was conducted using the signal-to-distortion ratio (SDR), scale-invariant signal-to-noise ratio (SI-SNR), and PESQ score. As seen in Table 2810 of FIG. 28, the ODAN method performs well in separating speakers in the mixture and even performs on par with the noncausal DAN method, which computes the separation from the entire utterance using a global clustering of the embeddings.

Figure 27B:
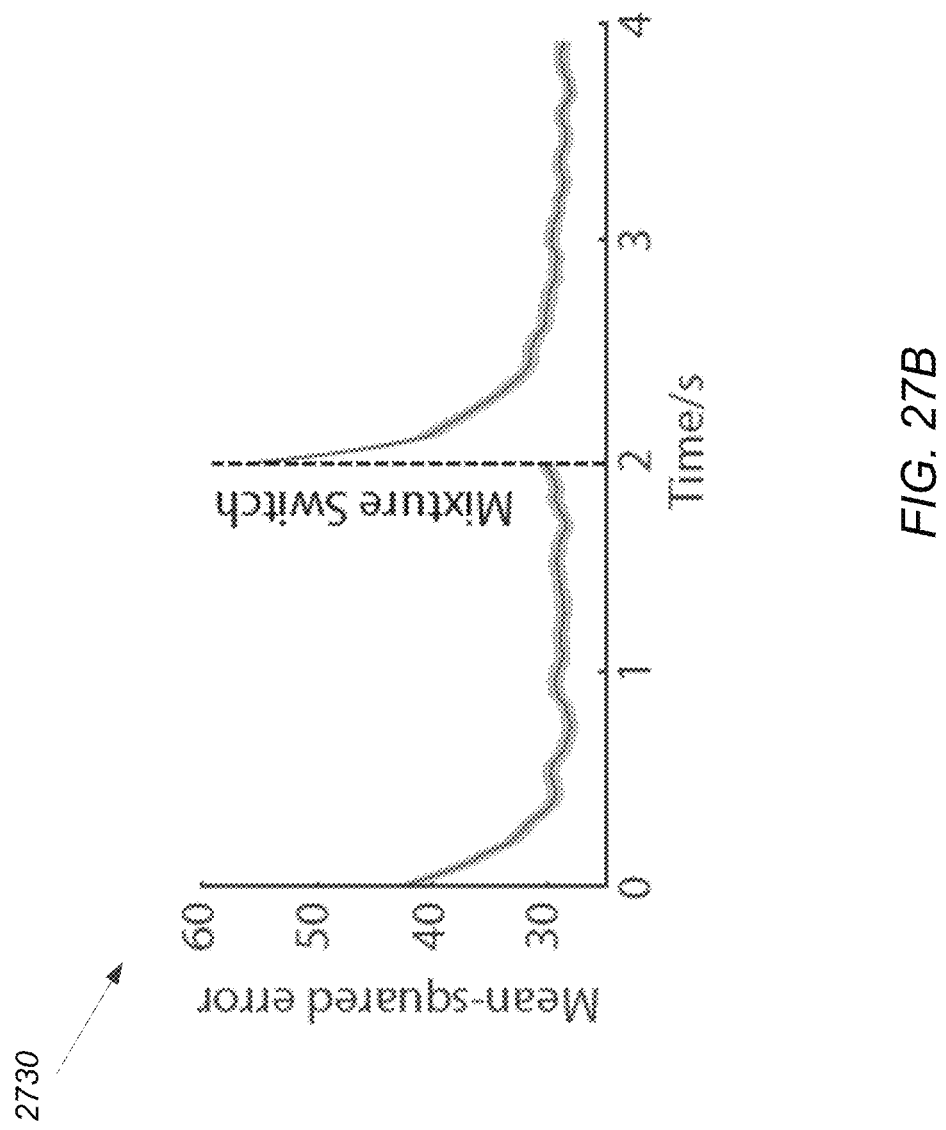
FIG. 27B includes a graph showing the mean-squared error (MSE) between the separated speech and actual speaker spectrograms over time.

In addition, an evaluation was conducted to determine whether ODAN can adapt and perform separation even when speakers in the mixture change over time, which frequently occurs in real-world situations. Mixtures of different speakers were concatenated where the speakers in the mixture change every 2 seconds. FIG. 27B provides a graph 2730 showing the mean-squared error (MSE) between the separated speech and actual speaker spectrograms over time where the line at 2 seconds indicates the time of speaker change. As seen in FIG. 27B, ODAN converges to new mixtures in less than 1.2 seconds (t-test, $p<0.05$) by adapting to new speakers to correctly separate them. This ability to track the speakers is important and enables it to work in real world acoustic scenarios.

To test the feasibility of using the ODAN speech separation network in a cognitively controlled hearing device, invasive electrophysiology was used to measure neural activity from three neurosurgical patients undergoing treatment for epilepsy. Two subjects (subjects 1 and 2) were implanted with high density subdural electrocorticography (ECoG) arrays over their language dominant temporal lobe, providing coverage of the superior temporal gyms (STG), which selectively represents attended speech. A third subject was implanted with bilateral stereotactic EEG (sEEG) with depth electrodes in Heschl's gyms (HG; containing primary auditory cortex) and STG. This implantation resulted in varying amounts of coverage over the left and right auditory cortices of each subject. All subjects had self-reported normal hearing and consented to participate in the experiment.

Each subject participated in the following experiments for this study: single-talker (S-T) and multitalker (M-T) experiments. In the S-T experiment, each subject listened to four continuous speech stories (each story was 3 minutes long) for a total of 12 minutes of speech material. The stories were uttered once by a female and once by a male speaker (hereafter referred to as Spk1 and Spk2, respectively). For the M-T experiment, subjects were presented with a mixture of the same speech stories as those in the S-T experiment where both speakers were combined at a 0 dB target-to-masker ratio. The M-T experiment was divided into 4 behavioral blocks, each containing a mixture of 2 different stories spoken by Spk1 and Spk2. Before each experimental block, subjects were instructed to focus their attention on one speaker and to ignore the other. All subjects began the experiment by attending to the male speaker and switched their attention to the alternate speaker on each subsequent block. To ensure that subjects were engaged in the task, the stories intermittently paused and subjects were asked to repeat the last sentence of the attended speaker before the pause. All subjects performed the task with high behavioral accuracy (subject 1: 94%, 2: 87.5%, and 3: 90%). Speech sounds were presented using a single loud speaker placed in front of the subject at comfortable hearing level, with no spatial separation between competing speakers. Data was recorded using Tucker Davis Technologies (TDT®) hardware and sampled at 2441 Hz. The data was resampled to 500 Hz. A $1^{st}$-order Butterworth high-pass filter with a cut-off frequency at 1 396 Hz was used to remove DC drift. Data was subsequently referenced using a local scheme whereby the average voltage from the nearest neighbors was subtracted from each electrode. Line noise at 60 Hz and its harmonics (up to 240 Hz) were removed using $2^{nd}$ order IIR notch filters with a bandwidth of 1 Hz. A period of silence was recorded before each experiment, and the corresponding data were normalized by subtracting the mean and dividing by the standard deviation of this pre-stimulus period. Data were filtered into the high-gamma band (70-150 Hz); the power of this band is modulated by auditory stimuli. To obtain the power of this broad band, the data was filtered into 8 frequency bands between 70 and 150 Hz with increasing bandwidth using Chebyshev Type 2 filters. Then, the power (analytic amplitude) of each band was obtained using 404 a Hilbert transform. The average of all 8 frequency bands was taken as the total power of the high-gamma band.

The reconstructed spectrogram from the auditory cortical responses of a listener in a multitalker speech perception task is more similar to the spectrogram of the attended speaker than that of the unattended speaker. Therefore, the comparison of the neurally reconstructed spectrogram with the spectrograms of individual speakers in a mixture can determine the attentional focus of the listener. A linear reconstruction method was used to convert neural responses back to the spectrogram of the sound. This method computed a linear mapping between the response of a population of neurons to the time-frequency representation of the stimulus. This mapping is performed by assigning a spatiotemporal filter to the set of electrodes, which is estimated by minimizing the MSE between the original and reconstructed spectrograms. The reconstruction filters were estimated using only the neural responses to speech in the S-T experiment. Then, we the filters were fixed and used to reconstruct the spectrogram in the M-T experiments under different attention focuses.

To determine the similarity of reconstructed spectrograms from neural responses to the spectrograms of attended and unattended speakers, the correlation coefficient (Pearson's r) between reconstructed spectrograms with both ODAN and the actual clean spectrograms of the two speakers was measured. The correlation values were estimated over the entire duration of the M-T experiment. The correlation between reconstructed and clean spectrograms was significantly higher for the attended speaker than for the unattended speaker (paired t-test, $p<<0.001$; Cohen's $D=0.8$). This observation shows the expected attentional modulation of the auditory cortical responses. Comparison of the correlation values of ODAN and actual clean spectrograms shows a similar difference value between attended and unattended spectrograms (average correlation difference for clean=0.125, and for ODAN=0.128), suggesting that ODAN spectrograms can be equally effective for attention decoding. The results also showed a small but significant decrease in the correlation values of reconstructed spectrograms with ODAN compared to those of the actual clean spectrograms. This decrease is caused by the imperfect speech separation performed by the ODAN process. Nevertheless, this difference is small and equally present for both attended and unattended speakers. Therefore, this difference did not significantly affect the decoding accuracy.

To study how the observed reconstruction accuracy with attended and unattended speakers translates into attention decoding accuracy, a simple classification scheme was used in which the correlation between the reconstructed spectrograms was computed with both clean attended and unattended speaker spectrograms over a specified duration. Next, the attended speaker was determined as the speaker with a higher correlation value. The duration of the signal used for the calculation of the correlation is an important parameter and impacts both the decoding accuracy and speed. Longer durations increase the reliability of the correlation values, hence improving the decoding accuracy. No significant difference in decoding accuracy with ODAN or clean spectrograms was found when different time windows were used (Wilcoxon rank sum test; $p=0.9$). This finding confirms that automatically separated sources by the ODAN process result in attention decoding accuracy similar to that with the actual clean spectrograms. As expected, increasing the correlation window resulted in improved decoding accuracy for both ODAN and actual clean sources.

Figure 29:
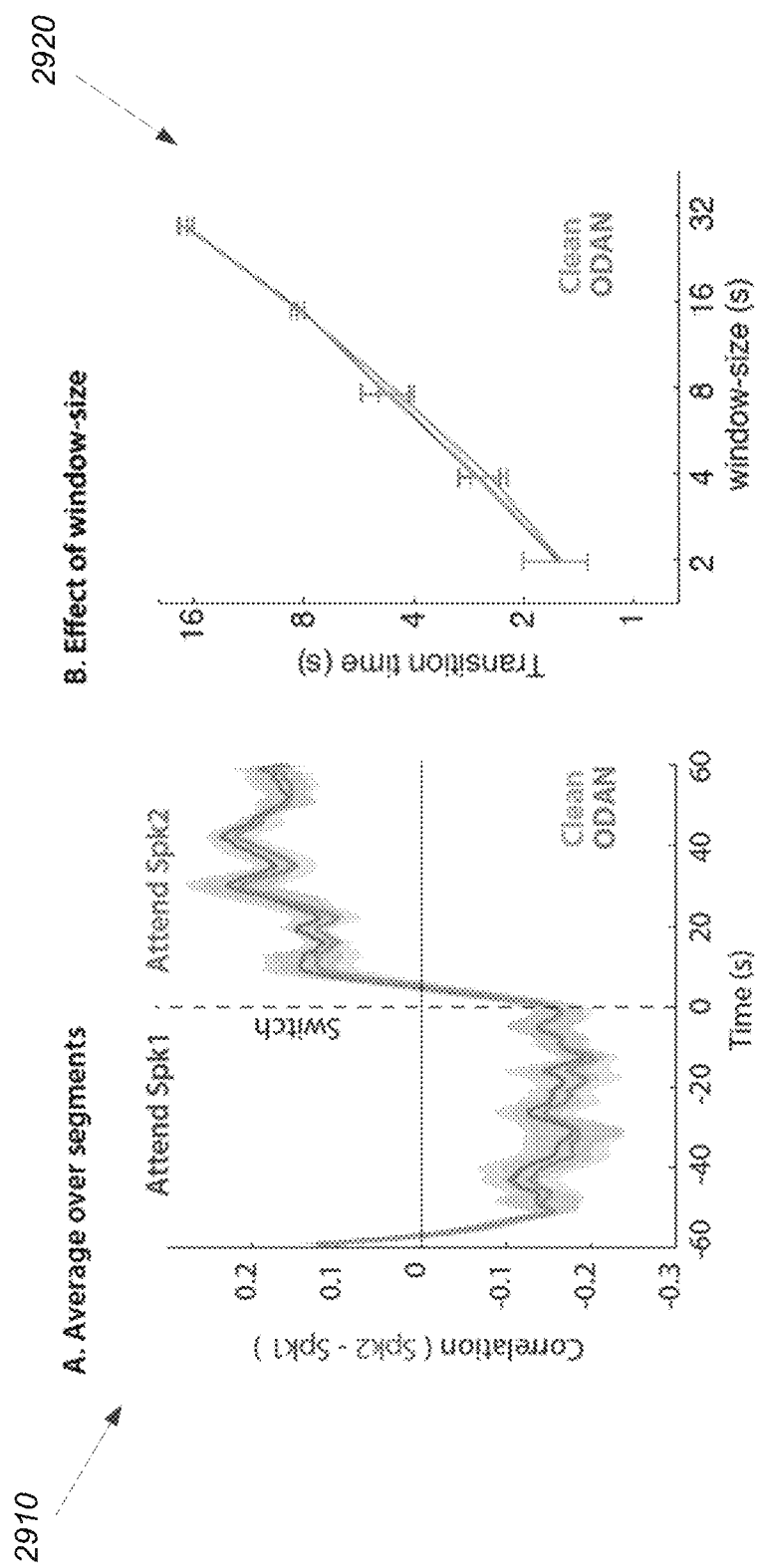
FIG. 29 includes a graph showing the average correlation for one example subject over all the segments, and another graph showing the average transition times for the three subjects for 5 different sliding window durations.

Next, the temporal properties of attention decoding were examined when ODAN and actual clean spectrograms were used. A dynamic switching of attention was simulated where the neural responses were concatenated from different attention experiment blocks such that the neural data alternated between attending to the two speakers. To accomplish this, the neural data was divided in each experiment block into 60-second segments (total of 12 segments) and interleaved segments from the two attention conditions. The correlation values between the reconstructed spectrograms were compared with both ODAN and actual clean spectrograms using a sliding window of 4 seconds. Then, the correlation values were averaged over the segments by aligning them according to the time of the attention switch. FIG. 29 includes a graph 2910 showing the average correlation for one example subject over all the segments where the subject was attending to Spk1 in the first 60 seconds and switched to Spk2 afterward. The overlap between the correlation plots calculated from ODAN and actual clean spectrograms shows that the temporal properties of attention decoding are the same in both cases; hence, ODAN outputs can replace clean spectrograms without any significant decrease in decoding speed. The decoding speed was quantified using the transition time, which is the time it takes to detect a switch in the listener's attention. Transition times were calculated as the time at which the average correlation crossed the zero line. FIG. 29 also includes a graph 2920 showing the average transition times for the three subjects for 5 different sliding window durations. As expected, the transition times increase for longer window lengths but there were no significant differences between ODAN and clean spectrograms (paired t-test, $p>>0.05$).

To test if the difficulty of attending to the target speaker is reduced using the ODAN-AAD system, a psychoacoustic experiment was performed comparing both the original mixture and sounds in which the decoded target speaker was amplified by 12 dB. Subjects were asked to rate the difficulty of attending to the target speaker in three conditions when listening to the following: 1) the raw mixture, 2) enhanced target speech using the output of ODAN-AAD, and 3) enhanced target speech using the output of the Clean-AAD system. Twenty listeners with normal hearing participated in the psychoacoustic experiment where they each heard 20 sentences in each of the three experimental conditions in random order. Subjects were instructed to attend to one of the speakers and report the difficulty of focusing on that speaker. Subjects were asked to rate the difficulty on a scale from 1 to 5 using the mean opinion score (MOS). The average subjective score for ODAN-AAD showed a significant improvement over the mixture (100% improvement, paired t-test, $p<<0.001$), demonstrating that the listeners had a stronger preference for the modified audio than for the original mixture. The results also showed a small but significant difference between the average MOS score with actual clean sources and that with ODAN separated sources (118% vs. 100% improvement over the mixture). The MOS values using the clean sources shows the upper bound of AAD improvement if the speaker separation process was perfect. Therefore, this analysis illustrates the maximum extra gain that can be achieved by improving the accuracy of the speech separation process (18% over the current system). A similar analysis was performed when an objective perceptual speech quality measure was used (perceptual evaluation of speech quality: PESQ), showing a result similar to what was observed in the subjective tests. The results demonstrate the benefit of using the ODAN-AAD system in improving the perceived quality of the target speaker.

Thus, presented herein is a framework for AAD that addresses the lack of access to clean speech sources in real world applications. The methodology implemented uses a novel, real-time speaker-independent speech separation process that uses deep-learning methods to separate the speakers from a single channel of audio. Then, the separated sources are compared to the reconstructed spectrogram from the auditory cortical responses of the listener to determine and amplify the attended source. The system was tested on two unseen speakers and showed improved subjective and objective perception of the attended speaker when using the ODAN-AAD framework. An advantage of this framework is the ability to generalize to unseen speakers, which allows a user to communicate more easily with new speakers. Nonetheless, generalization to various noisy, reverberant acoustic conditions is a more challenging problem and requires training on a large amount of data recorded from as many noisy environments as possible. Similar speech processing approaches, such as automatic speech recognition, have seen great benefit from large-scale training whenever possible. Therefore, speech separation is also expected to obtain a similar benefit in robustness to adverse acoustic conditions. In addition to increasing the amount of training data and training conditions, separation accuracy can be improved when more than one microphone can be used to record mixed audio. The advantage of enhancing speech with multiple microphones has been previously demonstrated, particularly in severely noisy environments or when the number of competing speakers is large (e.g., more than three). The multichannel extension of ODAN can be performed either by incorporating a beamformer with the separation network or by including the spatial dimension as an extra dimension of the embedding space.

A possible limitation in advanced signal processing approaches for hearing technologies is the limited computation and power resources that are available in wearable devices. Nevertheless, designing specialized hardware that can efficiently implement deep neural network models is an active research area that has recently seen substantial progress. Specialized hardware also significantly reduces the power consumption needed for computation. In addition, hearing aid devices can perform off-board computation by interfacing with a remote device, such as a mobile phone, which provides another possibility for extending the computational power of such devices.

Although the testing and evaluations performed used invasive neural recordings to test our system, previous studies have already shown that attention decoding is also possible with noninvasive neural recordings, including scalp EEG, around the ear EEG electrodes, and in-ear EEG recordings. The signal-to-noise ratio of these recordings is not as high as that of invasive methods, but they can provide enough information needed to decode the attentional focus, which may come at the expense of reducing the decoding speed of the AAD. Alternatively, several recent studies have examined the efficacy of minimally invasive neural recording techniques where the electrodes are placed under the skin without penetrating the bone. Further advances in noninvasive neural recording from the human brain can further increase the fidelity of the neural recording to improve both the accuracy and speed of attention decoding.

In parallel, decoding accuracy also critically depends on the decoding procedure being used. For example, the accuracy and speed of decoding can be improved when stochastic models are used to estimate the attention focus using a state-space model instead of the simple moving average.

Figure 30:
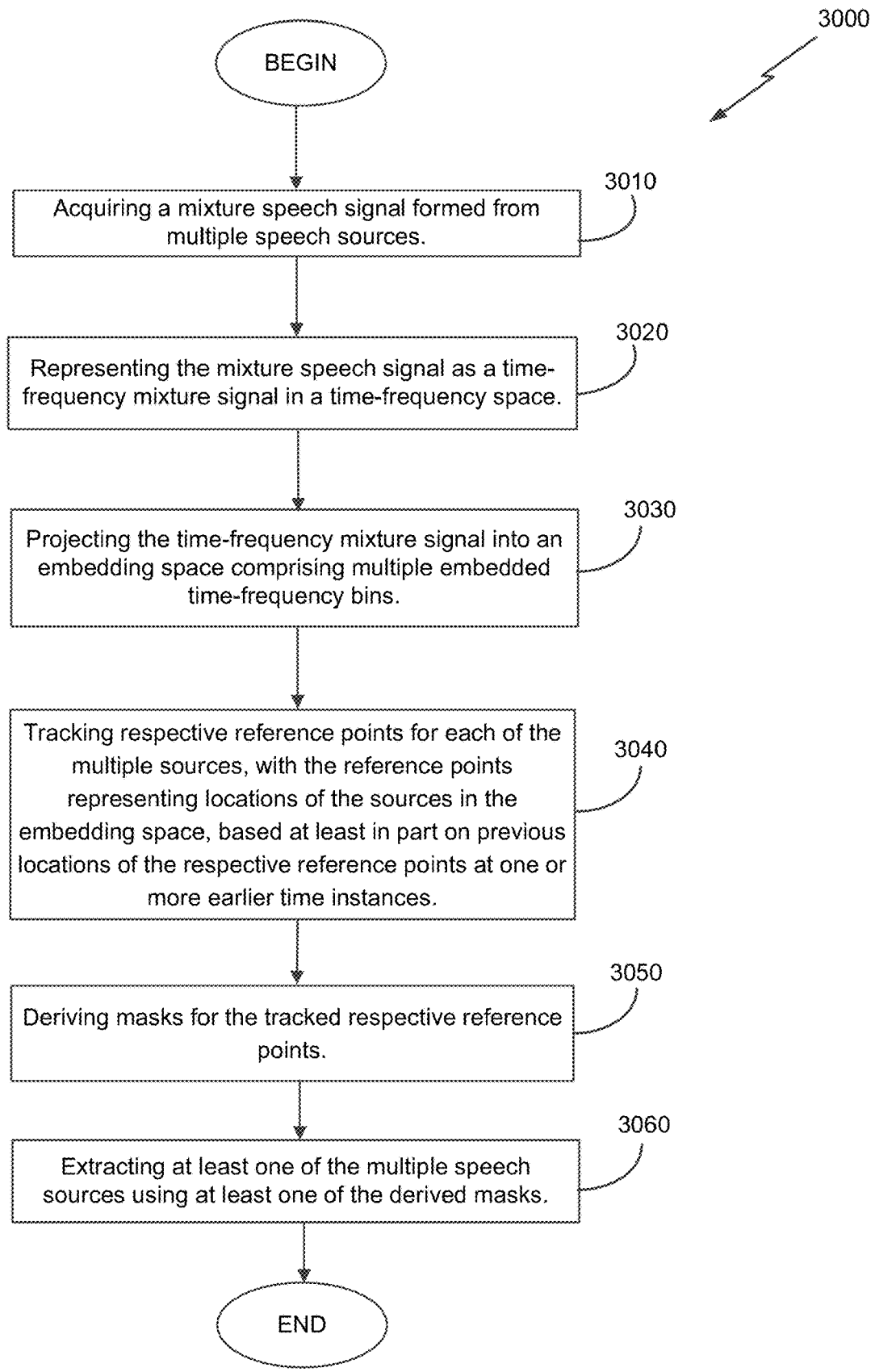
FIG. 30 is a flowchart of an example online deep attractor network (ODAN) speech separation procedure.

With reference now to FIG. 30, a flowchart of an example speech separation procedure 3000 (namely, the online deep attractor network, or ODAN, signal separation procedure) is shown. As noted, the procedure may be used in conjunction with an auditory attention decoding process (e.g., to select one of the separated speech sources according to neural signals obtained for an individual), or as part of some other application or procedure such as surveillance applications (to separate and record speech from a combined sound signal corresponding to different speakers), virtual reality applications (reconstructing speaking objects from a pre-recorded source, and rendering the separated speech signals into a virtual audio, or audio-visual, scene), noise cancellation application, etc.

The procedure 3000 includes acquiring 3010 a mixture speech signal formed from multiple speech sources. As discussed herein, the mixture signal may be the combined sounds signal of the procedure 300, which includes multiple sounds signals from multiple sounds sources. The mixture speech signal may be obtained using a single audio sensor, such as a microphone, or using multiple audio sensors. Having obtained the mixture speech signal, the procedure 3000 further includes representing the mixture speech signal as a time-frequency mixture signal in a time-frequency space. For example, in some embodiments, representing the mixture speech signal as the time-frequency mixture signal in the time-frequency space may include transforming the mixture signal into a time-frequency spectrogram representation. Other types of representations and/or signal transformation may be used.

The procedure 3000 additionally includes projecting 3030 the time-frequency mixture signal into an embedding space comprising multiple embedded time-frequency bins. As discussed herein, and as illustrated in FIGS. 25A and 26, projecting the time-frequency mixture signal into the embedding space may include processing the time-frequency mixture signal with a neural network comprising a plurality of stacked long short-term memory (LSTM) layers, coupled to a fully connected network.

The procedure 3000 further includes tracking 3040 respective reference points for each of the multiple sources, with the reference points representing locations of the sources in the embedding space, based at least in part on previous locations of the respective reference points at one or more earlier time instances. The reference points may include, for example, attractor points in the embedding space. Tracking the respective reference points may include computing distances of current embedded time-frequency bins to previous locations of the respective reference points at an earlier time instance, and assigning the each of the current embedded time-frequency bins to respective ones of the multiple sources based on the computed distances. In such embodiments, the procedure 3000 may also include updating current locations of the reference points based, at least in part, on assignments of the each of the current embedded time-frequency bins to the respective ones of the multiple sources.

The procedure 3000 also includes deriving 3050 masks for the tracked respective reference points, and extracting 3060 at least one of the multiple speech sources using at least one of the derived masks. Deriving masks for the tracked reference points may include generating the masks based, at least in part, on the updated current locations of the references points.

Other Embodiments

Figure 31:
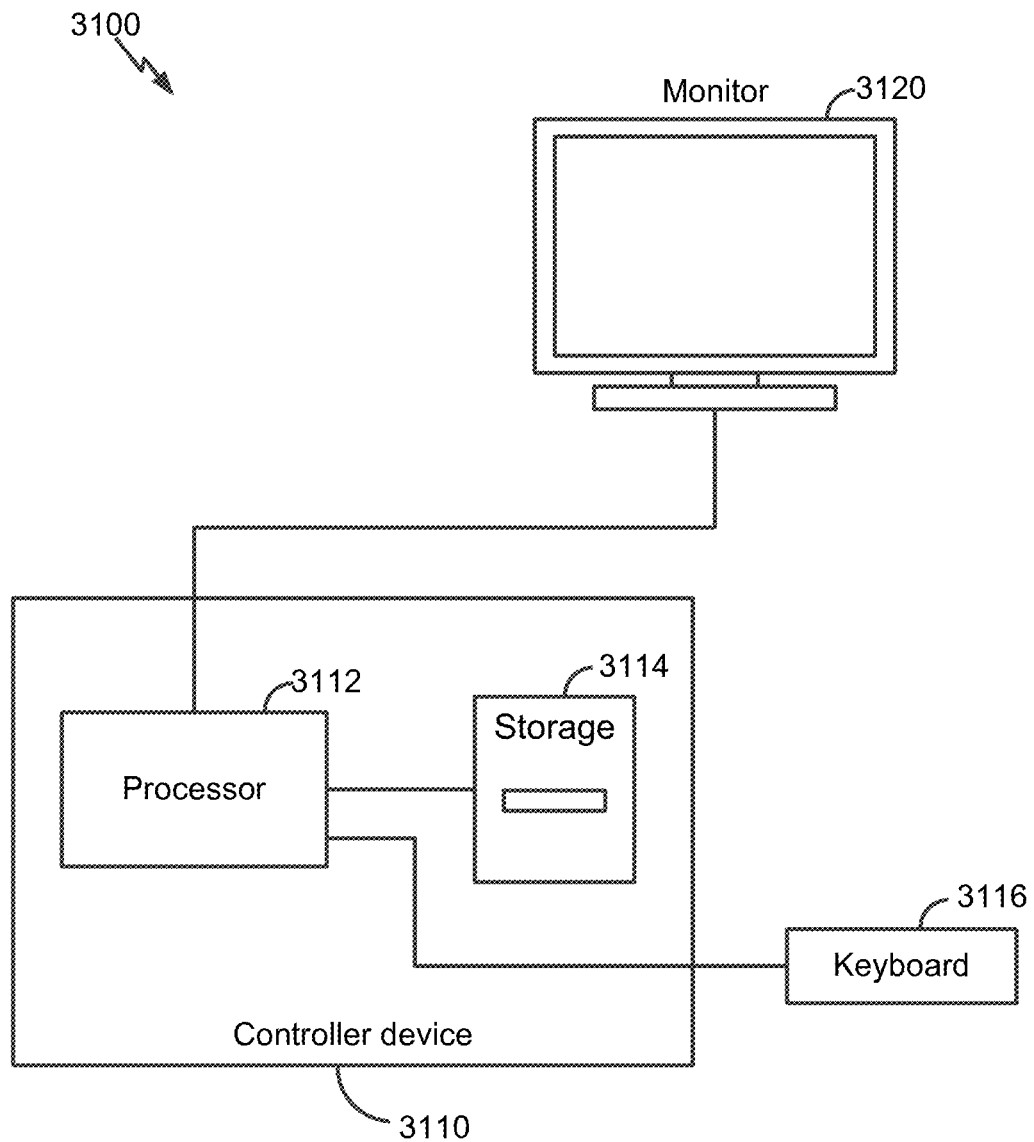
FIG. 31 is a schematic diagram of a controller system.

Performing the various procedures, processes, and operations described herein may be facilitated by a controller system (e.g., a processor-based controller system, a state machine, etc.) Particularly, at least some of the various devices/systems (e.g., hearing devices, or other types of hearing augmentation devices) described herein may be implemented, at least in part, using one or more controllers such as the one shown in FIG. 31, illustrating an example computing or controller system 3100. The computing system 3100 includes a computing-based device 3110 such as a personal computer, a specialized computing device, a controller circuit (implemented on a chip), and so forth, that typically includes a central controller 3112 (which may a programmable processor, such as a CPU). In addition to the central controller 3112, the system includes main memory, cache memory and bus interface circuits (not shown in FIG. 31). The computing/controller-based device 3110 may include a mass storage element 3114, such as a hard drive or flash drive associated with the computer system. The computing/controller system 3100 may further include a keyboard 3116, or keypad, or some other user input interface, and a monitor 3120, e.g., an LCD (liquid crystal display) monitor, that may be placed where a user can access them. The computing system 3100 may be incorporated within a system such as the various devices described herein.

The computing-based device 3110 is configured to facilitate, for example, the implementation of operations for neural decoding of attentional selection in multi-speaker environments, as well as for speech separation processing (including one or more of deep attractor networks, online deep attractor networks, time-domain audio separation using a deep long-short term memory network (LSTM), convolutional encoder approach for time-domain audio Separation network, etc.) The storage device 3114 may thus include a computer program product that when executed on the computing/controller-based device 3110 causes the computing-based device to perform operations to facilitate the implementation of procedures and operations described herein. The computing/controller-based device may further include peripheral devices to enable input/output functionality. Such peripheral devices may include, for example, a CD-ROM drive and/or flash drive (e.g., a removable flash drive), or a network connection (e.g., implemented using a USB port and/or a wireless transceiver), for downloading related content to the connected system. Such peripheral devices may also be used for downloading software containing computer instructions to allow general operation of the respective system/device. Alternatively and/or additionally, in some embodiments, special purpose logic circuitry, e.g., an FPGA (field programmable gate array), an ASIC (application-specific integrated circuit), a DSP processor, etc., may be used in the implementation of the system 3100. Other modules that may be included with the computing-based device 3110 are speakers, a sound card, a pointing device, e.g., a mouse or a trackball, by which the user can provide input to the computing system 3100. The computing/controller-based device 3110 may include an operating system, e.g., Windows XP® Microsoft Corporation operating system, Ubuntu operating system, etc.

Computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a non-transitory machine-readable medium that receives machine instructions as a machine-readable signal.

In some embodiments, any suitable computer readable media can be used for storing instructions for performing the processes/operations/procedures described herein. For example, in some embodiments computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as flash memory, electrically programmable read only memory (EPROM), electrically erasable programmable read only Memory (EEPROM), etc.), any suitable media that is not fleeting or not devoid of any semblance of permanence during transmission, and/or any suitable tangible media. As another example, transitory computer readable media can include signals on networks, in wires, conductors, optical fibers, circuits, any suitable media that is fleeting and devoid of any semblance of permanence during transmission, and/or any suitable intangible media.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate in the context of the systems, devices, circuits, methods, and other implementations described herein.

As used herein, including in the claims, "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition.

Although particular embodiments have been disclosed herein in detail, this has been done by way of example for purposes of illustration only, and is not intended to be limiting with respect to the scope of the appended claims, which follow. Features of the disclosed embodiments can be combined, rearranged, etc., within the scope of the invention to produce more embodiments. Some other aspects, advantages, and modifications are considered to be within the scope of the claims provided below. The claims presented are representative of at least some of the embodiments and features disclosed herein. Other unclaimed embodiments and features are also contemplated.

What is claimed is:

1. A method comprising:
   obtaining, by a device, a combined sound signal for signals combined from multiple sound sources in an area in which a person is located;
   applying, by the device, a neural-network-based speech-separation processing to the combined sound signal from the multiple sound sources to derive a plurality of separated signals that each contains signals corresponding to different groups of the multiple sound sources, wherein applying the speech-separation processing comprises:
      transforming the combined signal into an embedding space;
      determining respective reference points in the embedding space for each of the multiple sound sources, with the reference points representing locations of the sound sources in the embedding space for the combined sound signal;
      deriving masks for the determined reference points; and
      extracting at least one of the multiple sound sources using at least one of the derived masks;
   obtaining, by the device, neural signals for the person, the neural signals being indicative of one or more of the multiple sound sources the person is attentive to; and
   selecting one of the plurality of separated signals based on the obtained neural signals for the person.

2. The method of claim 1, wherein obtaining the neural signals for the person comprises:
   obtaining one or more of: electrocorticography (ECoG) signals for the person, neural measurements via a non-invasive scalp, or in-ear EEG recordings.

3. The method of claim 1, further comprising:
   processing the selected one of the plurality of separated sound signals, including performing one or more of: amplifying the selected one of the plurality of separated signals, or attenuating at least one non-selected signal from the plurality of separated signals.

4. The method of claim 1, wherein obtaining the combined sound signal for the multiple sound sources comprises:
   receiving the combined sound signal for the multiple sound sources at a single microphone coupled to the device.

5. The method of claim 1, wherein applying the neural-network-based speech-separation processing to the combined sound signal from the multiple sound sources comprises:
   providing the combined sound signal from the multiple sound sources to a deep neural network (DNN) configured to identify individual sound sources from the combined sound signal.

6. The method of claim 1, wherein determining the respective reference points comprises:
   determining the respective reference points using a deep neural network.

7. The method of claim 1, wherein deriving the masks comprises:
   computing similarity between embedded points within the embedding space and the determined respective reference points.

8. The method of claim 1, wherein the reference points comprise attractor points in the embedding space.

9. A method comprising:
   obtaining, by a device, a combined sound signal for signals combined from multiple sound sources in an area in which a person is located;
   applying, by the device, a neural-network-based speech-separation processing to the combined sound signal from the multiple sound sources to derive a plurality of separated signals that each contains signals corresponding to different groups of the multiple sound sources, wherein applying the neural-network-based speech-separation processing comprises:
      dividing the combined sound signal into non-overlapping segments;
      transforming the non-overlapping segments into respective weighted sums of a learnable overcomplete basis of signals, wherein weight coefficients for the respective weighted sums are non-negative;
      performing neural-network-based processing on the respective weighted sums of the learnable overcomplete basis of signals to derive a plurality of mask matrices corresponding to different groups of the multiple sound sources; and
      estimating a plurality of reconstructed sounds signals from the derived plurality of mask matrices corresponding to the different groups of the multiple sound sources;
   obtaining, by the device, neural signals for the person, the neural signals being indicative of one or more of the multiple sound sources the person is attentive to; and
   selecting one of the plurality of separated signals based on the obtained neural signals for the person.

10. The method of claim 9, wherein transforming the non-overlapping segments into the respective weighted sums comprises:
    estimating the respective weighted sums of the learnable overcomplete basis of signals using a gated 1-D convolution layer according to:

$$w_k = \text{ReLU}(x_k * U) \odot \sigma(x_k * V), k=1,2,\ldots,K$$

where $U \in R^{N \times L}$ and $V \in R^{N \times L}$ are N vectors with length L, $w_k \in R^{1 \times N}$ is a mixture weight vector for segment k, $\sigma$ denotes a Sigmoid activation function, and * denotes a convolution operator.

11. The method of claim 9, wherein performing neural-network-based processing on the respective weighted sums to derive the plurality of mask matrices comprises:
    inputting the respective weighted sums of the learnable overcomplete basis of signals to a deep long-short term network (LSTM) followed by a fully connected layer with Softmax activation function for mask generation.

12. The method of claim 9, wherein estimating the plurality of reconstructed sounds signals comprises:
    computing a source weight matrix, $D_i$, according to $D_i = W \odot M_i$, where $D_i = [d_{i,1}, \ldots, d_{i,K}] \in R^{K \times N}$ is the weight matrix for source i; and
    synthesizing a time-domain synthesis of the sources by multiplying the weight matrix $D_i$ with basis signals $B \in R^{N \times L}$.

13. A method comprising:
    obtaining, by a device, a combined sound signal for signals combined from multiple sound sources in an area in which a person is located;
    applying, by the device, a neural-network-based speech-separation processing to the combined sound signal from the multiple sound sources to derive a plurality of separated signals that each contains signals corresponding to different groups of the multiple sound sources, wherein applying the speech-separation processing comprises:
  representing the combined sound signal as a time-frequency mixture signal in a time-frequency space;
  projecting the time-frequency mixture signal into an embedding space comprising multiple embedded time-frequency bins;
  tracking respective reference points for each of the multiple sound sources, with the reference points representing locations of the multiple sound sources in the embedding space, based at least in part on previous locations of the respective reference points at one or more earlier time instances;
  deriving masks for the tracked respective reference points; and
  extracting at least one of the multiple sound sources using at least one of the derived masks;
obtaining, by the device, neural signals for the person, the neural signals being indicative of one or more of the multiple sound sources the person is attentive to; and
selecting one of the plurality of separated signals based on the obtained neural signals for the person.

14. The method of claim 13, wherein projecting the time-frequency mixture signal into the embedding space comprises:
  processing the time-frequency mixture signal with a neural network comprising a plurality of stacked long short-term memory (LSTM) layers, coupled to a fully connected network.

15. The method of claim 13, wherein the reference points comprise attractor points in the embedding space.

16. The method of claim 13, wherein tracking the respective reference points comprises:
  computing distances of current embedded time-frequency bins to previous locations of the respective reference points at an earlier time instance; and
  assigning the each of the current embedded time-frequency bins to respective ones of the multiple sources based on the computed distances.

17. The method of claim 16, further comprising updating current locations of the reference points based, at least in part, on assignments of the each of the current embedded time-frequency bins to the respective ones of the multiple sources;
  and wherein deriving masks for the tracked reference points comprises generating the masks based, at least in part, on the updated current locations of the references points.

18. A method comprising:
  obtaining, by a device, a combined sound signal for signals combined from multiple sound sources in an area in which a person is located;
  applying, by the device, a neural-network-based speech-separation processing to the combined sound signal from the multiple sound sources to derive a plurality of separated signals that each contains signals corresponding to different groups of the multiple sound sources, wherein applying the speech-separation processing comprises:
    dividing the combined sound signal into a plurality of segments;
    transforming the plurality of segments into a plurality of corresponding encoded segments represented in an intermediate feature space;
    estimating, for each of the plurality of corresponding encoded segments, multiple mask functions for respective ones of the multiple sound sources by passing the each of the plurality of corresponding encoded segments through a stacked dilated convolutional network;
    multiplying the estimated mask functions with the respective one of the plurality of corresponding encoded segments to produce respective resultant multiple masked segments; and
    generating separated estimates of the signals from the multiple sound sources based on the respective resultant multiple masked segments;
  obtaining, by the device, neural signals for the person, the neural signals being indicative of one or more of the multiple sound sources the person is attentive to; and
  selecting one of the plurality of separated signals based on the obtained neural signals for the person.

19. A system comprising:
  at least one microphone to obtain a combined sound signal for signals combined from multiple sound sources in an area in which a person is located;
  one or more neural sensors to obtain neural signals for the person, the neural signals being indicative of one or more of the multiple sound sources the person is attentive to; and
  a controller coupled to the at least one microphone and the one or more neural sensors, the controller configured to:
    apply a neural-network-based speech-separation processing to the combined sound signal from the multiple sound sources to derive a plurality of separated signals that each contains signals corresponding to different groups of the multiple sound sources, wherein the controller configured to apply the speech-separation processing is configured to:
      transform the combined signal into an embedding space;
      determine respective reference points in the embedding space for each of the multiple sound sources, with the reference points representing locations of the sound sources in the embedding space for the combined sound signal;
      derive masks for the determined reference points; and
      extract at least one of the multiple sound sources using at least one of the derived masks; and
    select one of the plurality of separated signals based on the obtained neural signals for the person.

20. A system comprising:
  at least one microphone to obtain a combined sound signal for signals combined from multiple sound sources in an area in which a person is located;
  one or more neural sensors to obtain neural signals for the person, the neural signals being indicative of one or more of the multiple sound sources the person is attentive to; and
  a controller coupled to the at least one microphone and the one or more neural sensors, the controller configured to:
    apply a neural-network-based speech-separation processing to the combined sound signal from the multiple sound sources to derive a plurality of separated signals that each contains signals corresponding to different groups of the multiple sound sources, wherein the controller configured to apply the speech-separation processing is configured to:
      divide the combined sound signal into non-overlapping segments;

transform the non-overlapping segments into respective weighted sums of a learnable overcomplete basis of signals, wherein weight coefficients for the respective weighted sums are non-negative;

perform neural-network-based processing on the respective weighted sums of the learnable overcomplete basis of signals to derive a plurality of mask matrices corresponding to different groups of the multiple sound sources; and estimate a plurality of reconstructed sounds signals from the derived plurality of mask matrices corresponding to the different groups of the multiple sound sources; and select one of the plurality of separated signals based on the obtained neural signals for the person.

21. The system of claim 20, wherein the controller configured to perform the neural-network-based processing on the respective weighted sums to derive the plurality of mask matrices is configured to:

input the respective weighted sums of the learnable overcomplete basis of signals to a deep long-short term network (LSTM) followed by a fully connected layer with Softmax activation function for mask generation.

22. A system comprising:

at least one microphone to obtain a combined sound signal for signals combined from multiple sound sources in an area in which a person is located;

one or more neural sensors to obtain neural signals for the person, the neural signals being indicative of one or more of the multiple sound sources the person is attentive to; and a controller coupled to the at least one microphone and the one or more neural sensors, the controller configured to:

apply a neural-network-based speech-separation processing to the combined sound signal from the multiple sound sources to derive a plurality of separated signals that each contains signals corresponding to different groups of the multiple sound sources, wherein the controller configured to apply the speech-separation processing is configured to:

represent the combined sound signal as a time-frequency mixture signal in a time-frequency space;

project the time-frequency mixture signal into an embedding space comprising multiple embedded time-frequency bins using a neural network comprising a plurality of stacked long short-term memory (LSTM) layers, coupled to a fully connected network;

track respective reference points for each of the multiple sound sources, with the reference points representing locations of the multiple sound sources in the embedding space, based at least in part on previous locations of the respective reference points at one or more earlier time instances;

derive masks for the tracked respective reference points; and extract at least one of the multiple sound sources using at least one of the derived masks; and select one of the plurality of separated signals based on the obtained neural signals for the person.

23. A non-transitory computer readable media programmed with instructions, executable on a processor, to:

obtain, by a device comprising the processor, a combined sound signal for signals combined from multiple sound sources in an area in which a person is located;

apply, by the device, a neural-network-based speech-separation processing to the combined sound signal from the multiple sound sources to derive a plurality of separated signals that each contains signals corresponding to different groups of the multiple sound sources, wherein the instructions to apply the speech-separation processing include one or more instructions to:

transform the combined signal into an embedding space;

determine respective reference points in the embedding space for each of the multiple sound sources, with the reference points representing locations of the sound sources in the embedding space for the combined sound signal;

derive masks for the determined reference points; and extract at least one of the multiple sound sources using at least one of the derived masks;

obtain, by the device, neural signals for the person, the neural signals being indicative of one or more of the multiple sound sources the person is attentive to; and select one of the plurality of separated signals based on the obtained neural signals for the person.

24. The system of claim 19, wherein the one or more neural sensors configured to obtain the neural signals for the person are configured to:

obtain one or more of: electrocorticography (ECoG) signals for the person, neural measurements via a non-invasive scalp sensor, or in-ear EEG recordings.

25. The system of claim 19, wherein the controller is further configured to:

process the selected one of the plurality of separated sound signals, including to perform one or more of: amplify the selected one of the plurality of separated signals, or attenuate at least one non-selected signal from the plurality of separated signals.

26. The system of claim 19, wherein the at least one microphone configured to obtain the combined sound signal for the multiple sound sources includes a single microphone to receive the combined sound signal for the multiple sound sources.

27. The system of claim 19, wherein the controller configured to determine the respective reference points is configured to:

determine the respective reference points using a deep neural network.

28. The system of claim 19, wherein the controller configured to derive the masks is configured to:

compute similarity between embedded points within the embedding space and the determined respective reference points.

29. The system of claim 19, wherein the reference points comprise attractor points in the embedding space.

30. The system of claim 20, wherein the controller configured to transform the non-overlapping segments into the respective weighted sums is configured to:

estimate the respective weighted sums of the learnable overcomplete basis of signals using a gated 1-D convolution layer according to:

$$w_k = \text{ReLU}(x_k * U) \odot \sigma(x_k * V), k=1,2,\ldots,K,$$

where $U \in R^{N \times L}$ and $V \in R^{N \times L}$ are N vectors with length L, $w_k \in R^{1 \times N}$ is a mixture weight vector for segment k, $\sigma$ denotes a Sigmoid activation function, and * denotes a convolution operator.

31. The system of claim 20, wherein the controller configured to perform neural-network-based processing on the respective weighted sums to derive the plurality of mask matrices is configured to:
  input the respective weighted sums of the learnable overcomplete basis of signals to a deep long-short term network (LSTM) followed by a fully connected layer with Softmax activation function for mask generation.

32. The system of claim 20, wherein the controller configured to estimate the plurality of reconstructed sounds signals is configured:
  compute a source weight matrix, $D_i$, according to $D_i = W \odot M_i$, where $D_i = [d_{i,1}, \ldots, d_{i,K}] \in R^{K \times N}$ is the weight matrix for source i; and
  synthesize a time-domain synthesis of the sources by multiplying the weight matrix $D_i$ with basis signals $B \in R^{N \times L}$.

33. The system of claim 20, wherein the one or more neural sensors configured to obtain the neural signals for the person are configured to:
  obtain one or more of: electrocorticography (ECoG) signals for the person, neural measurements via a non-invasive scalp sensor, or in-ear EEG recordings.

34. The system of claim 22, wherein the controller configured to track the respective reference points is configured to:
  compute distances of current embedded time-frequency bins to previous locations of the respective reference points at an earlier time instance; and
  assign the each of the current embedded time-frequency bins to respective ones of the multiple sources based on the computed distances.

35. The system of claim 22, wherein the controller is further configured to:
  update current locations of the reference points based, at least in part, on assignments of the each of the current embedded time-frequency bins to the respective ones of the multiple sources;
  and wherein the controller configured to derive masks for the tracked reference points is configured to generate the masks based, at least in part, on the updated current locations of the references points.

36. The system of claim 22, wherein the one or more neural sensors configured to obtain the neural signals for the person are configured to:
  obtain one or more of: electrocorticography (ECoG) signals for the person, neural measurements via a non-invasive scalp sensor, or in-ear EEG recordings.

37. The system of claim 22, wherein the reference points comprise attractor points in the embedding space.

38. The method of claim 18, wherein obtaining the neural signals for the person comprises:
  obtaining one or more of: electrocorticography (ECoG) signals for the person, neural measurements via a non-invasive scalp, or in-ear EEG recordings.

39. The method of claim 18, further comprising:
  processing the selected one of the plurality of separated sound signals, including performing one or more of: amplifying the selected one of the plurality of separated signals, or attenuating at least one non-selected signal from the plurality of separated signals.

* * * * *